US010280221B2

(12) United States Patent
Hamblin et al.

(10) Patent No.: US 10,280,221 B2
(45) Date of Patent: *May 7, 2019

(54) ANTI-LAG-3 BINDING PROTEINS

(71) Applicant: GLAXOSMITHKLINE INTELLECTUAL PROPERTY DEVELOPMENT LIMITED, Middlesex (GB)

(72) Inventors: Paul Andrew Hamblin, Stevenage (GB); Alan Peter Lewis, Stevenage (GB); Thomas Matthew Webb, Brentford (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 404 days.

This patent is subject to a terminal disclaimer.

(21) Appl. No.: 14/774,728

(22) PCT Filed: Mar. 13, 2014

(86) PCT No.: PCT/EP2014/054967

§ 371 (c)(1), (2) Date: Sep. 11, 2015

(87) PCT Pub. No.: WO2014/140180

PCT Pub. Date: Sep. 18, 2014

(65) Prior Publication Data

US 2016/0017037 A1 Jan. 21, 2016

Related U.S. Application Data

(60) Provisional application No. 61/789,325, filed on Mar. 15, 2013.

(51) Int. Cl.
*C07K 16/28* (2006.01)
*A61K 39/395* (2006.01)

(52) U.S. Cl.
CPC .... *C07K 16/2803* (2013.01); *A61K 39/39541* (2013.01); *A61K 39/39558* (2013.01); *C07K 2317/24* (2013.01); *C07K 2317/56* (2013.01); *C07K 2317/565* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,703,039 A | 10/1987 | Hawiger et al. | |
| 4,873,316 A | 10/1989 | Meade et al. | |
| 5,739,277 A | 4/1998 | Presta et al. | |
| 5,747,035 A | 5/1998 | Presta et al. | |
| 5,869,046 A | 2/1999 | Presta et al. | |
| 5,976,877 A | 11/1999 | Hercend et al. | |
| 6,197,524 B1 | 3/2001 | Romagnani | |
| 6,946,292 B2 | 9/2005 | Kanda et al. | |
| 7,214,775 B2 | 5/2007 | Hanai et al. | |
| 9,244,059 B2 | 1/2016 | Triebel et al. | |
| 2005/0053973 A1 | 3/2005 | Kolkman et al. | |
| 2005/0089932 A1 | 4/2005 | Kolkman et al. | |
| 2005/0164301 A1 | 7/2005 | Kolkman et al. | |
| 2007/0148165 A1 | 6/2007 | Shitara et al. | |
| 2010/0233183 A1 | 9/2010 | Triebel et al. | |
| 2011/0027295 A1* | 2/2011 | Powell | A61K 39/39558 424/174.1 |
| 2011/0070238 A1 | 3/2011 | Triebel et al. | |
| 2011/0150892 A1 | 6/2011 | Thudium et al. | |
| 2014/0286935 A1 | 9/2014 | Hamblin et al. | |
| 2016/0176965 A1 | 6/2016 | Haudebourg et al. | |

FOREIGN PATENT DOCUMENTS

| | | |
|---|---|---|
| EP | 0054951 | 6/1981 |
| EP | 0054951 A1 | 6/1982 |
| EP | 0239400 | 9/1987 |
| EP | 0239400 A2 | 9/1987 |
| EP | 1158004 | 11/2001 |
| EP | 1158004 A2 | 11/2001 |
| EP | 1229125 | 8/2002 |
| EP | 1229125 A1 | 8/2002 |
| EP | 1374902 | 1/2004 |
| EP | 1374902 A1 | 1/2004 |
| EP | 1987839 | 11/2008 |
| EP | 1987839 A1 | 11/2008 |
| WO | 91/14438 A1 | 10/1991 |
| WO | 1991/14438 | 10/1991 |
| WO | 96/16990 A1 | 6/1996 |
| WO | 1996/16990 | 6/1996 |
| WO | 96/32478 A1 | 10/1996 |
| WO | 1996/32478 | 10/1996 |
| WO | 97/03695 | 2/1997 |

(Continued)

OTHER PUBLICATIONS

Poirier et al. (Clinical and Experimental Immunology, 164: 265-274, 2011) (Year: 2011).*
Bettini et al. (J Immunol 2011; 187:3493-3498, 2011). (Year: 2011).*
Herwijnen et al. (Proc Natl Acad Sci U S A. Aug. 28, 2012;109(35):14134-9, 2012) (Year: 2012).*
Andre, et al., CD40L stabilizes arterial thrombi by a β3 integrin-dependent mechanism, Nature Medicine 8(3): 247-252 (2002).
Andreae, et al., Maturation and Activation of Dendritic Cells Induced by Lymphocyte Activation Gene-3 (CD223)1, J Immunol 168: 3874-3880 (2002).
Andreae, et al., MHC class II signal transduction in human dendritic cells induced by a natural ligand, the LAG-3 protein (CD223), Blood 102(6): 2130-2137 (2003).

(Continued)

*Primary Examiner* — Zachary S Skelding
(74) *Attorney, Agent, or Firm* — Natalie A. Lissy; Duke M. Fitch; Edward R. Gimmi

(57) ABSTRACT

Antigen binding proteins that bind Lymphocyte Activation Gene 3 (LAG-3), and more particularly to antigen binding proteins that cause depletion of LAG-3+ activated T cells.

11 Claims, 5 Drawing Sheets

Specification includes a Sequence Listing.

(56) References Cited

FOREIGN PATENT DOCUMENTS

| WO | 97/03695 A1 | 2/1997 |
|---|---|---|
| WO | 97/35614 A1 | 10/1997 |
| WO | 97/43316 A1 | 11/1997 |
| WO | 1997/43316 | 11/1997 |
| WO | 99/15553 | 4/1999 |
| WO | 99/15553 A2 | 4/1999 |
| WO | 99/43713 A1 | 9/1999 |
| WO | 1999/43713 | 9/1999 |
| WO | 99/58679 A1 | 11/1999 |
| WO | 1999/58679 | 11/1999 |
| WO | 00/09560 | 2/2000 |
| WO | 00/09560 A2 | 2/2000 |
| WO | 00/42072 | 7/2000 |
| WO | 00/42072 A2 | 7/2000 |
| WO | 00/61739 | 10/2000 |
| WO | 00/61739 A1 | 10/2000 |
| WO | 02/31240 | 4/2002 |
| WO | 02/31240 A2 | 4/2002 |
| WO | 02/060919 | 8/2002 |
| WO | 02/060919 A2 | 8/2002 |
| WO | 03/011878 | 2/2003 |
| WO | 03/011878 A2 | 2/2003 |
| WO | 03/076567 | 9/2003 |
| WO | 03/076567 A2 | 9/2003 |
| WO | 2004/078928 | 9/2004 |
| WO | 2004/078928 A2 | 9/2004 |
| WO | 2004/081026 | 9/2004 |
| WO | 2004/081026 A2 | 9/2004 |
| WO | 2005/077042 | 8/2005 |
| WO | 2005/077042 A2 | 8/2005 |
| WO | 2005/103086 | 11/2005 |
| WO | 2005/103086 A1 | 11/2005 |
| WO | 2006/012508 A2 | 2/2006 |
| WO | 2006/014679 | 2/2006 |
| WO | 2006/014679 A1 | 2/2006 |
| WO | 2007/011041 | 1/2007 |
| WO | 2007/011041 A1 | 1/2007 |
| WO | 2008/096158 | 8/2008 |
| WO | 2008/096158 A2 | 8/2008 |
| WO | 2008/132601 A1 | 11/2008 |
| WO | WO 2008/132601 | 11/2008 |
| WO | 2010/019570 A2 | 2/2010 |
| WO | WO 2010/019570 | 2/2010 |
| WO | 2014/008218 A1 | 1/2014 |
| WO | WO 2014/008218 | 1/2014 |

OTHER PUBLICATIONS

Annunziato, et al., Expression and release of LAG-3-encoded protein by human CD4+ T cells are associated with IFN-y production, The FASEB Journal 10: 769-776 (1996).

Avice, et al., Lymphocyte Activation Gene-3, a MHC Class II Ligand Expressed on Activated T Cells, Stimulates TNF-α and IL-12 Production by Monocytes and Dendritic Cells1, J Immunol 162: 2748-2753 (1999).

Baixeras, et al., "Characterization of the Lymphocyte Activation Gene 3-Encoded Protein. A New Ligand for Human Leukocyte Antigen Class II Antigens", J Exp Med 176: 327-337 (1992).

Bayry, et al., Rescuing CD4+CD25+ regulatory T-cell functions in rheumatoid arthritis by cytokine-targeted monoclonal antibody therapy, (2007) Drug Disc Today 12(13/14): 548-552.

Bindon, et al., Importance of antigen specificity for complement mediated lysis by monoclonal antibodies, (1988) Eur J Immunol 18: 1507-1514.

Bostrom, et al.,"Improving Antibody Binding Affinity and Specificity for Therapeutic Development", Methods in Molecular Biology 525: 353-376 (2009).

Boyd, et al., The Effect of the Removal of Sialic Acid, Galactose and Total Carbohydrate on the Functional Activity of Campath-1H, Molecular Immunol, 32(17/18): 1311-1318 (1996).

Brignone, et al., "A Soluble Form of Lymphocyte Activation Gene-3 (IMP321) Induces Activation of a Large Range of Human Effector Cytotoxic Cells", J Immunol 179: 4202-4211 (2007).

Bruniquel, et al., "Regulation of expression of the human lymphocyte activation gene-3 (LAG-3) molecule, a ligand for MHC class II", Immunogenetics 48: 116-124 (1998).

Camisaschi, et al., "LAG-3 Expression Defines a Subset of CD4+ CD25highFox3+ Regulatory T Cells That are Expanded at Tumour Sites", J Immunol 184: 6545-6551 (2010).

Campbell, et al., Collagen-induced arthritis in C57BL/6 (H-2b) mice: new insights into an important disease model of rheumatoid arthritis, (2000) Eur J Immunol 30(6): 1568-1575.

Chan, et al., Variable region domain exchange in human IgGs promotes antibody complex formation with accompanying structural changes and altered effector functions, (2004) Molecular Immunol 41: 527-538.

Chappel, et al., Identification of a Secondary FcyRI Binding Site within a Genetically Engineered Human IgG Antibody, (1993) J Biological Chem 268(33): 25124-25131.

Chothia, et al., Conformations of immunoglobulin hypervariable regions, (1989) Nature 342(21/28): 877-883.

Cole, et al., The Ebv-Hybridoma Technique and its Application to Human Lung Cancer, (1985) Monoclonal Antibodies and Cancer Therapy, Alan R. Liss, Inc., 77-96.

Coles, et al., "Alemtuzumab vs. Interferon Beta-1a in Early Multiple Sclerosis—The CAMMS223 Trial Investigators", N Engl J Med 359: 1786-1801 (2008).

Dall' Acqua, et al., "Increasing the Affinity of a Human IgG1 for the Neonatal Fc Receptor: Biological Consequences", J Immunol 169: 5171-5180 (2002).

Dall' Acqua, et al., "Modulation of the Effector Functions of a Human IgG1 through Engineering of its Hinge Region", J Immunol 177: 1129-1138 (2006).

Davis, B.G., "Synthesis of Glycoproteins", Chem Rev 102(2): 579-601 (2002).

Definition of auto immune, http://dictionary.cambridge.org/dictionary/british/auto-immune?=auto-immune, 1-page, Monday Jul. 30, 2012.

De Groot and Martin, "Reducing Risk, Improving Outcomes: Bioengineering Less Immunogenic Protein Therapeutics", Clin Immunol 131: 189-201 (2009).

De Pascalis, et al., Grafting of 'Abbreviated' Complementarity-Determining Regions Containing Specificity-Determining Residues Essential for Ligand Contact to Engineer a Less Immunogenic Humanized Monoclonal Antibody, (2002) J Immunol 169: 3076-3084.

Drake, et al., Blocking the regulatory T-cell molecule LAG-3 augments in vivo anti-tumor immunity in an autochthonous model of prostate cancer, (2006) J Clin Oncol 24(18): 2573.

Ewert, et al., "Stability improvement of antibodies for extracellular and intracellular applications: CDR grafting to stable frameworks and structure-based framework engineering", Methods 34: 184-199 (2004).

Galli, et al., Unequivocal Delayed Hypersensitivity in Mast Cell-Deficient and Beige Mice, (1984) Science 226: 710-713.

Ghetie, et al., "Increasing the serum persistence of an IgG fragment by random mutagenesis", Nature Biotechnol 15: 637-640 (1997).

Ghetie and Ward, "Multiple Roles for the Major Histocompatibility Complex Class I-Related Receptor FcRn" Ann Rev Immunol 18: 739-766 (2000).

Hang and Bertozzi, "Chemoselective Approaches to Glycoprotein Assembly", Acc Chem Res 34: 727-736 (2001).

Hannier, et al., "CD3/TCR Complex-Associated Lymphocyte Activation Gene-3 molecules Inhibit CD3/TCR Signaling", J Immunol 161: 4058-4065 (1998).

Hargreaves, et al., "Selective depletion of activated T-cells: the CD40L-specific antibody experience", Trends in Mol Med 10(3): 130-135 (2004).

Hinton, et al., Engineered Human IgG Antibodies with Longer Serum Half-lives in Primates, J Biological Chem 279(8): 6213-6216 (2004).

Hodgson, John, "Making Monoclonals in Microbes", Bio/Technol 9: 421-425 (1991).

Holliger and Hudson, "Engineered Antibody Fragments and the Rise of Single Domains", Nature Biotechnol 23(9): 1126-1136 (2005).

(56) References Cited

OTHER PUBLICATIONS

Huang, et al., Role of LAG-3 in Regulatory T Cells, (2004) Immunity 21: 503-513.
Huard, et al., "Cellular expression and tissue distribution of the human LAG-3-encoded protein, an MHC class II ligand", Immunogenetics 39: 213-217 (1994).
Huard, et al., Lymphocyte-activation gene 3/major histocompatibility complex class II interaction modulates the antigenic response of CD4+ T lymphocytes, (1994) Eur J Immunol 24: 3216-3221.
Huard, et al., "Characterization of the major histocompatibility complex class II binding site on LAG-3 protein", Proc Natl Acad Sci USA 94: 5744-5749 (1997).
Huard, et al., LAG-3 does not defne a specific mode of killing in human, (1998) Immunol Ltrs 61: 109-112.
Inglis, et al., Collagen-induced arthritis in C57BL/6 mice is associated with a robust and sustained T-cell response to type II collagen, (2007) Arthritis Research and Therapy, 9: R113.
Issacs,J.D., "From bench to bedside: discovering rules for antibody design, and improving serotherapy with monoclonal antibodies", Rheumatology 40: 724-738 (2001).
Iwai, et al., "Involvement of Inducible Costimulator B7 Homologous Protein Costimulatory Pathway in Murine Lupus Nephritis1", J Immunol 171: 2848-2854 (2003).
Jones, et al., Chapter 21: Deimmumization of Monoclonal Antibodies; Antony Dimitrov (Ed),Therapeutic Antibodies: Methods and Protocols 525: 405-423 (2009).
Junghans, R.P., Finally! The Brambell Receptor (FcRB), Mediator of Transmission of Immunity and Protection from Catabolism for IgG, Immunol Res 16(1): 29-57 (1997).
Kim, et al., Antibody Engineering for the Development of Therapeutic Antibodies, (2005) Mol Cells 20(1): 17-29.
Kisielow, et al., "Expression of lymphocyte activation gene 3 (LAG-3) on B cells is induced by T cells", Eur J Immunol 35: 2081-2088 (2005).
Kohler, et al., "Continuous cultures of fused cells secreting antibody of predefined specificity", Nature 256: 495-497 (1975).
Kontermann, Therapeutic Proteins: Strategies to Modulate Their Plasma Half-Lives Edited by Roland, Wiley-Blackwell, ISBN: 978-3-527-32849-9, Chapter 4, pp. 63-80; Chapter 9, pp. 157-188; Chapter 12, pp. 223-247; Chapter 14, pp. 269-283 and Chapter 15, pp. 285-296 (2012).
U.S. Appl. No. 12/598,128, filed Mar. 19, 2010, cited above as U.S. Patent Application Serial No. 2010-0233183 published Sep. 16, 2010.
U.S. Appl. No. 12/823,795, filed Jun. 25, 2010, cited above as U.S. Pat. No. 9,244,059 issued Jan. 26, 2106.
U.S. Appl. No. 14/208,684, filed Mar. 13, 2014, cited above as U.S. Patent Application Serial No. 2014/0286935 published Sep. 25, 2014.
U.S. Appl. No. 14/970,926, filed Dec. 16, 2015, cited above as U.S. Patent Application Serial No. 2016/0176965 published Jun. 23, 2016.
Kunstfeld, et al., "Induction of cutaneous delayed-type hypersensitivity reactions in VEGF-A transgenic mice results in chronic skin inflammation associated with persistent lymphatic hyperplasia", Blood 104: 1048-1057 (2004).
Lamminmaki, et al., "Crystal Structure of a Recombinant Anti-estradiol Fab Fragment in Complex with 17b- Estradiol", J Biological Chem 276(39): 36687-36694 (2001).
Lange-Asschenfeldt, et al., "Increased and prolonged inflammation and angiogenesis in delayed-type hypersensitivity reactions elicited in the skin of thrombospondin-2-deficient mice", Blood 99: 538-545 (2002).
Lazar, et al., "Engineered antibody Fc variants with enhanced effector function", PNAS 103(11): 4005-4010 (2006).
Lienhardt, et al., "Active tuberculosis in Africa is associated with reduced Th1 and increased Th2 activity in vivo" Eur J Immunol 32: 1605-1613 (2002).
MacCallum, et al., Antibody-antigen interactions: contact analysis and binding site topography, (1996) J Mol Biol 262:732-745.
Macon-Lemaître and Triebel, "The negative regulatory function of the lymphocyte-activation gene-3 co-receptor (CD223) on human T cells", Immunology 115(2): 170-178 (2005).
Mages, et al., "Molecular cloning and characterization of murine ICOS and identification of B7h as ICOS ligand", Eur J Immunol 30: 1040-1047 (2000).
Miller, et al., "An Insect Baculovirus Host-Vector System for High-Level Expression of Foreign Genes", Genetic Engineering: Principles and Methods 8: 277-298, Plenum Press (1986).
Monk, et al., "Fc-dependent depletion of activated T cells occurs through CD40L-specific antibody rather than costimulation blockade", Nature Medicine 9(10): 1275-1280 (2003).
Nechansky, et al., "Compensation of endogenous IgG mediated inhibition of antibody-dependent cellular cytotoxicity by glyco-engineering of therapeutic antibodies", Molecular Immunol 44: 1815-1817 (2007).
Nishida, et al., Novel humanized anti-CD20 monoclonal antibodies with unique germline VH and VL gene recruitment and potent effector functions, (2008) Int'l J Oncology 32: 1263-1274.
Nobel-Jamieson, et al., "Auto-immune cholangiopathy in a juvenile patient with systemic lupus erythematosus", Acta Paediatrica, Foundation Acta Paediatrica, 101: e262-e264 (2012).
Ono, et al., "Improved technique of heart transplantation in rats", Journal of Thoracic and Cardiovascular Surgery 57 (2): 225-229 (1969).
Ozkaynak, et al., "Importance of ICOS-B7RP-1 costimulation in acute and chronic allograft rejection", Nature Immunology 2(7): 591-596 (2001).
Patel and Boyd, "An improved assay for antibody dependent cellular cytotoxicity based on time resolved fluorometry", J Immunol Meth 184:29-38 (1995).
Plückthun, Andreaus, Mono- and Bivalent Antibody Fragments Produced in *Escherichia coli*: Engineering, Folding and Antigen Binding, Immunol Rev, 130: 151-188 (1992).
Queen, et al., "A humanized antibody that binds to the interleukin 2 receptor", Proc Natl Acad Sci USA, 86: 10029-10032 (1989).
Raju, et al., "Glycoengineering of Therapeutic Glycoproteins: In Vitro Galactosylation and Sialylation of Glycoproteins with Terminal N-Acetylglucosamine and Galactose Residues", Biochem 40: 8868-8876 (2001).
Rothe, et al., "Ribosome display for improved biotherapeutic molecules", Expert Opinion on Biological Therapy 6(2): 177-187 (2006).
Saito, et al., "A Tumor Necrosis Factor Receptor Loop Peptide Mimic Inhibits Bone Destruction to the Same Extent as Anti-Tumor Necrosis Factor Monoclonal Antibody in Murine Collagen-Induced Arthritis", Arthritis & Rheumatism 56 (4): 1164-1174 (2007).
Sakamoto, et al., "AILIM/ICOS: Its Expression and Functional Analysis with Monoclonal Antibodies", Hybridoma and Hybridomics 20(5): 293-303 (2001).
Sears and Wong, "Toward Automated Synthesis of Oligosaccharides and Glycoproteins", Science 291: 2344-2350 (2001).
Shields, et al., "High Resolution Mapping of the Binding Site on Human IgG1 for FcyRI, FcyRII, FcyRIII, and FcRn and Design of IgG1 Variants with Improved Binding to the FcyR", J Biol Chem 276(9): 6591-6604 (2001).
Siawaya, et al., "Immune parameters as markers of tuberculosis extent of disease and early prediction of anti-tuberculosis chemotherapy response", J Infect 56: 340-347 (2008).
Sierro, et al., "The CD4-like molecule LAG-3, biology and therapeutic applications" Expert Opinion on Therapeutic Targets 15(1): 91-101 (2011).
Song, et al., Rat and Human Natural Killers Exhibit Contrasting Immunoglobulin G Subclass Specifications in Antibody-Dependent Cellular Cytotoxicity Reflecting Differences in Their Fc Receptors (FcyR), (1990) Journal of Leukocyte Biology 48: 524-530.
Sporici, et al., ICOS Ligand Costimulation is Required for T-Cell Encephalitogenicity, (2001) Clinical Immunology 100(3): 277-288.
Stasiuk, et al., Collagen-Induced Arthritis in DBA/1 Mice: Cytokine Gene Activation Following Immunization with Type II Collagen, (1996) Cellular Immunology 173: 269-275.

(56) References Cited

OTHER PUBLICATIONS

Steplewski. et al., Biological activity of human-mouse IgG1, IgG2, IgG3, and IgG4 chimeric monoclonal antibodies with antitumor specificity , (1988) Proc Nat'l Acad Sci 85:4852-4856.
Teeling, et al., "The Biological Activity of Human CD2O Monoclonal Antibodies is Linked to Unique Epitopes on CD201", Journal of Immunology 177: 362-371 (2006).
Thie, et al., Chapter 16: "Affinity Maturation by Phage Display", Antony Dimitrov (Ed), Therapeutic Antibodies: Methods and Protocols 525: 309-322 (2009) [Methods Mol Bio].
Totsuka, et al., "Ameliorating Effect of Anti-Inducible Costimulator Monoclonal Antibody in a Murine Model of Chronic Colitis", Gastroenterology 124: 410-421 (2003).
Triebel, et al., "LAG-3: a regulator of T-cell and DC responses and its use in therapeutic vaccination ", Trends in Immunology 24(12): 619-622 (2003).
Triebel, et al., "A soluble lymphocyte activation gene-3 (sLAG-3) protein as a prognostic factor in human breast cancer expressing estrogen or progesterone receptors", Cancer Letters 235: 147-153 (2006).
Virella, et al., "Biosynthesis, Metabolism, and Biological Properties", Introduction to Medical Immunology, Chapter 6, 4th Edition, pp. 99-100 (1998).
Wacker, et al., N-Linked Glycosylation in Campylobacter jejuni and its Functional Transfer into *E. coli*, Science 298: 1790-1793 (2002).
Waldmann, Herman, "The new immunosuppression: just kill the T cell", Nature Medicine 9(10): 1259-1260 (2003).
Woo, et al., "Differential subcellular localization of the regulatory T-cell protein LAG-3 and the coreceptor CD4" Eur J Immunol 40:1768-1777 (2010).
Wörn and Plückthun, "Stability Engineering of Antibody Single-chain Fv Fragments", J Mol Biol 305: 989-1010 (2001).
Yousaf, et al., "Targeting behavior of rat monoclonal IgG antibodies in vivo: role of antibody isotype, specificity and the target cell antigen density", Eur J Immunol 21: 943-950 (1991).
Zhang, et al, "A New Strategy for the Synthesis of Glycoproteins", Science 303: 371-373 (2004).
Haudebourg, et al., "Depletion of LAG-3 positive cells in cardiac allograft reveals their role in rejection and tolerance", Transplantation, 84(11):1500-1506 (2007).
Poirier, et al., "Antibody-mediated depletion of lymphocyte-activation gene-3 (LAG-3+)-activated T lymphocytes prevents delayed-type hypersensitivity in non-human primates", Clinical and Experimental Immunology, 164(2):265-274 (2011).
Workman, et al., "The CD4-related molecule, LAG-3 (CD223), regulates the expansion of activated T cells", European Journal of Immunology, 33(4):970-979 (2003).
Belson, et al., Characterisation of the clinical and activated T cell response to repeat delayed-type hypersensitivity skin challenges in human subjects, with KLH and PPD, as potential model to test T-cell targeted therapies, Inflamm Res 65:389-404 (2016).
Buckner, Jane Hoyt, Mechanisms of impaired regulation by CD4+ CD25+FOXP3+ regulatory T cells in human autoimmune diseases, Nature Rev 10:849-859 (2010).
Chavele and Ehrenstein, Regulatory T-cells in systemic lupus erythematosus and rheumatoid arthritis, FEBS Letters 585:3603-3610 (2011).
Ehrenstein, et al., Compromised Function of Regulatory T Cells in Rheumatoid Arthritis and Reversal by Anti-TNF Therapy, J Exp Med 200(3):277-285 (2004).
Kitade, et al., Early Presence of Regulatory Cells in Transplanted Rats Rendered Tolerant by Donor-Specific Blood Transfusion, J Immunol 75:4963-4970 (2005).
Thomson, et al., FK506: a novel immunosuppressant for treatment of autoimmune disease: Rationale and preliminary clinical experience at the University of Pittsburgh, Springer Semin Immunopathol 14(4): 323-344 (1993).
Cole, et al., The Ebv-Hybridoma Technique and its Application to Human Lung Cancer, Monoclonal Antibodies and Cancer Therapy, Proceedings of the Roche-UCLA Sumposium Held in Park City, Utah, Jan. 26-Feb. 2, 1985, Ralph A. Reisfeld and Stewart Sell, Editors, Alan R. Liss, Inc., New York, pp. 77-96 [Previously submitted].
Definition of auto immune (Definition of auto-immune adjective from the Cambridge Advanced Learner's Dictionary & Thesaurus © Cambridge University Press) http://dictionary.cambridge.org/dictionary/british/auto-immune?q=auto-immune Monday, Jul. 30, 2012, 1 page [Previously submitted].
Jones, et al., Chapter 21: Deimmumization of Monoclonal Antibodies; Antony Dimitrov (Ed), Therapeutic Antibodies: Methods and Protocols 525: 405-423 (2009) © Humana Press, a part of Springer Science+Business Media, LLC [Previously submitted].
Yamane-Ohnuki, et al., Establishment of FUT8 knockout Chinese hamster ovary cells: an ideal host cell line for producing completely defucosylated antibodies with enhanced antibody-dependent cellular cytotoxity, Biotechnology and Bioengineering (2004) 87(5): 614-622.
Yasuda, et al. Humanization of Murine Antibodies by CDR-Grafting. Japanese Journal of Thrombosis and Hemostasis, 4(3): 193-200 (1993). (Translation attached).
Sugimura, et al. Dojin News, 109: 1-7 (Jan. 23, 2004). (Translation attached).
Hashiguchi, et al. The Journal of Japanese Biochemical Society, 82(8): 710-726 (2010). (Translation attached).
Saldanha, Jose W. Molecular Engineering I: Humanization—found in Chapter 6, pp. 119-144 of the Handbook of Therapeutic Antibodies, edited by Stephan Dubel, Jan. 1, 2007. Wiley-VCH, Weinheim, XP007913671, ISBN: 978-3-527-31453-9.
Definition of autoimmune (Definition of autoimmune, adjective from the Cambridge Advanced Learner's Dictionary & Thesaurus © Cambridge University Press) https://dictionary.cambridge.org/dictionary/english/autoimmune Accessed Jul. 19, 2018, 6 pages for Definition of auto immune (Definition of auto-immune adjective from the Cambridge Advanced Learner's Dictionary & Thesaurus © Cambridge University Press) http://dictionary.cambridge.org/dictionary/british/auto-immune?q=auto-immune Monday, Jul. 30, 2012, 1 page (previously submitted).
U.S. Appl. No. 12/598,128, filed Mar. 19, 2010, cited previously as U.S. Publication No. 2010-0233183 published Sep. 16, 2010; Title: Cytotoxic Anti-LAG-3 Monoclonal Antibody and its Use in the Treatment or Prevention or Organ Transplant Rejection and Autoimmune Disease; Inventors Frederic Triebel, Bernard Vanhove and Thomas Haudebourg; 21 pages.
U.S. Appl. No. 12/823,795, filed Jun. 25, 2010, cited previously as U.S. Pat. No. 9,244,059 issued Jan. 26, 2016; Title:Cytotoxic Anti-LAG-3 Monoclonal Antibody and its Use in the Treatment for Prevention of Organ Transplant Rejection and Autoimmune Disease; Inventors Frederic Triebel, Bernard Vanhove and Thomas Haudebourg; 40 pages.
U.S. Appl. No. 14/970,926, filed Dec. 16, 2015, cited previously as U.S. Patent Application Serial No. 2016/0176965 published Jun. 23, 2016; Title: Cytotoxic Anti-LAG-3 Monoclonal Antibody and its Use in the Treatment or Prevention of Organ Transplant Rejection and Autoimmune Disease; Inventors Thomas Haudebourg, Frederic Triebel and Bernard Vanhove, 40 pages.
Kisielow et al: "Expression of lymphocyte activation gene 3 (LAG-3) on B cells is induced by T cells", European Journal of Immunology, vol. 35, No. 7, Jul. 1, 2005 (Jul. 1, 2005 ), pp. 2081-2088, XP055162755, ISSN: 0014-2980, DOI: 10.1002/eji.200526090.
Velders M P et al: "The Impact of Antigen Density and Antibody Affinity on Antibody-Dependent Cellular Cytotoxicity: Relevance for Immunotherapy of Carcinomas", British Journal of Cancer, Nature Publishing Group, GB, vol. 78, No. 4, Aug. 1, 1998 (Aug. 1, 1998 ), pp. 478-483, XP009027871, ISSN: 0007-0920.
Jamali et al: "Kinetics of Anti-CD4-Induced T Helper Cell Depletion and Inhibition of Function Activation of T Cells by the CD3 Pathway Inhibits Anti-CD4-Mediated T Cell Elimination and Down-Regulation of Cell Surface CD4", The Journal of Immunology, vol. 148, No. 6, Mar. 15, 1992 (Mar. 15, 1992), pp. 1613-1619, XP055213914, ISSN: 0022-1767.

(56) References Cited

OTHER PUBLICATIONS

Uchida J et al: "The innate mononuclear phagocyte network depletes B lymphocytes through Fe receptor-dependent mechanisms during antiCD20 antibody immunotherapy", The Journal of Experimental Medicine, Rockefeller University Press, US, vol. 199, No. 12, Jun. 21, 2004 (Jun. 21, 2004 ), pp. 1659-1669, XP003002436, ISSN: 0022-1007, DOI: 10.1084/JEM.20040119.

* cited by examiner

A

| | IMP731 | H5L7BW | H5L7 |
|---|---|---|---|
| IC50 | 13.04 | 16.88 | 14.22 |

B

| | IMP731 | H5L7 | H5L7BW | Synagis |
|---|---|---|---|---|
| IC50 | 2.141 | 3.061 | 3.073 | ~ 3.597e+010 |

A

B

ANTI-LAG-3 BINDING PROTEINS

This application is the US National Stage of International Application No. PCT/EP2014/054967, filed 13 Mar. 2014 which claims benefit of the filing date of U.S. Provisional Application No. 61/789,325, filed 15 Mar. 2013, both of which are incorporated herein by reference in their entireties.

FIELD OF THE INVENTION

The present invention is directed to antigen binding proteins, particularly antibodies that bind Lymphocyte Activation Gene (LAG-3) and cause depletion of activated T cells expressing LAG-3, polynucleotides encoding such antigen binding proteins, pharmaceutical compositions containing said antigen binding proteins, and to the use of said antigen binding proteins in the treatment and/or prevention of diseases associated with the involvement of pathogenic T cells.

BACKGROUND TO THE INVENTION

Lymphocyte Activation Gene-3 (LAG-3) is a negative co-stimulatory receptor that modulates T cell homeostasis, proliferation and activation (Sierro S et al; Expert Opin. Ther. Targets (2010) 15: 91-101). An immunoglobulin superfamily member, LAG-3 is a CD4-like protein which, like CD4, binds to MHC class II molecules, but with two-fold higher affinity and at a distinct site from CD4 (Huard B et al., (1997) Proc Natl Acad Sci USA 94: 5744-9). In addition to exerting very distinct functions (CD4 is a positive co-stimulatory molecule) the two receptors are also differentially regulated. CD4 is constitutively expressed on the surface of all mature CD4+ T cells, with only a small fraction residing intracellularly, whereas a large proportion of LAG-3 molecules are retained in the cell close to the microtubule-organizing centre, and only induced following antigen specific T cell activation (Woo S R et al., (2010) Eur J Immunol 40: 1768-77). The role of LAG-3 as a negative regulator of T cell responses is based on studies with LAG-3 knockout mice and use of blocking anti-LAG-3 antibodies in model in vitro and in vivo systems (Sierro S et al., Expert Opin. Ther. Targets (2010) 15: 91-101; Hannier S et al (1998), J Immunol 161: 4058-65; Macon-Lemaitre L et al (2005), Immunology 115: 170-8; Workman C J et al (2003), Eur J Immunol 33:970-9).

At the cell surface, LAG-3 is expressed as a dimer, which is required for formation of stable MHC class II binding sites (Huard B et al. (1997) Proc Natl Acad Sci USA 94: 5744-9). LAG-3, in soluble form, also occurs in serum of healthy donors and patients with tuberculosis and cancer (Lienhardt C et al. (2002), Eur J Immunol 32: 1605-13; Triebel F et al (2006). Cancer Lett 235: 147-53), and this form may correlate with the number of LAG-3+ T cells (Siawaya J et al. (2008). J of Infection 56: 340-7). The key attribute of LAG-3 as a target antigen for an enhanced lymphocyte depletion agent is its relatively selective expression profile when compared with other agents currently in the clinic, i.e. Campath™ (T/B cells), Amevive (most CD45RO+ T-cells) or Rituxan (B-cells). Few molecules have been identified as sustained markers of in vivo T cell activation in humans. These include LAG-3, OX40, MHC class II, CD69, CD38, ICOS and CD40L. However, apart from LAG-3 and OX40 the majority of these molecules are also constitutively expressed on human natural T regs or on other cell types. LAG-3 is expressed on a small proportion of T-cells in healthy humans (ca. 1-4%), and in a similar proportion of NK cells (Baixeras E et al. (1992), J Exp Med 176: 327-37; Huard B et al (1994), Immunogenetics 39: 213-7). Upon activation with anti-CD3 ca. 30-80% of both CD4+ and CD8+ T cells express LAG-3 within 24 to 48 h; this percentage is increased in presence of IL2, IL7 and IL12 (Sierro S et al, Expert Opin. Ther. Targets (2010) 15: 91-101; Bruniquel D et al (1998), Immunogenetics 48: 116-24). Following antigen-specific stimulation with recall antigen (i.e. CMV or Tetanus toxoid) the majority of activated T cells are LAG-3+. In addition, in humans, LAG-3 is expressed on a sub-population (1-10%) of CD4+ CD25+ FoxP3+ T regs in healthy human blood. This population appears to be functionally suppressive in vitro by cell contact and IL10 dependent mechanisms and therefore may represent a population of recently activated natural or induced T regs [Camisaschi C, Casati C, Rini F et al. (2010). LAG-3 expression defines a subset of CD4+ CD25highFox3P+regulatory T cells that are expanded at tumour sites. J. Immunol 184: 6545-51). LAG-3 has been detected on other cell types of hematopoietic lineage, such as plasmacytoid dendritic cells, B-cells, and NKT-cells, but only in the mouse, and mostly following activation (Sierro S, Romero P & Speiser D; Expert Opin. Ther. Targets (2010) 15: 91-101).

Depletion of LAG-3+ T cells may be used to treat or prevent T cell driven immuno-inflammatory disorders. In auto-immune diseases where the majority of auto-reactive cells are chronically activated by self antigens at the disease site and/or re-circulate in the periphery, a short course of a depleting antigen binding protein may selectively deplete this auto-immune T cell repertoire providing long term remission. The precedence for this approach has been demonstrated with the pan-lymphocyte depleting antibody Campath™, in which a single 12 mg injection reduced the rate of relapse by 74% compared to standard treatment in a multiple sclerosis trial (The CAMMS223 Trial Investigators (2008), N Engl J Med. 359:1786-801). Due to the more selective expression of LAG-3 compared with CD52, the target for Campath™, the impact on the naïve and resting memory T cell and natural T regs repertoire should be reduced. This is expected to lead to an improved therapeutic index, maintaining efficacy, but with reduced risk of infection and malignancy as well as onset of auto-immunity associated with Campath™. Additionally, in a baboon tuberculin skin challenge model, the LAG-3 targeting chimeric antibody IMP731 mediated depletion of LAG-3+ T-cells, both in the periphery and at the skin challenge site, resulting in a reduction in the tuberculin skin challenge response (Poirier N et al. (2011), Clin Exp Immunol 164: 265-74). In a further study, a LAG-3 polyclonal antibody depleted LAG-3+ infiltrating T-cells from a rat cardiac allograft and prolonged the survival of these grafts (Haudebourg T et al. (2007), Transplantation 84: 1500-1506).

There exists a need in the art for antigen binding proteins, particularly humanised antibodies, that bind LAG-3 and cause deletion of LAG-3+ activated T cells, and which may have use in the treatment of auto-immune diseases, such as psoriasis, Crohn's disease, rheumatoid arthritis, primary biliary cirrhosis, systemic lupus erythematosus (SLE), Sjögren's syndrome, multiple sclerosis, ulcerative colitis and autoimmune hepatitis; infectious diseases, allergic diseases and cancer.

SUMMARY OF THE INVENTION

The present invention is broadly directed to antigen binding proteins, such as humanised antibodies, which bind Lymphocyte Activation Gene 3 (LAG-3) and which may be able to cause depletion of LAG-3+ activated T cells. More particularly, antigen binding proteins of the present invention may comprise CDRL1, CDRL2 and CDRL3 of SEQ ID No. 5.

Antigen binding proteins described herein may have use in the treatment or prevention of diseases associated with the involvement of pathogenic T cells, for example auto-immune diseases, such as psoriasis, Crohn's disease, rheumatoid arthritis, primary biliary cirrhosis, systemic lupus erythematosus (SLE), Sjögren's syndrome, multiple sclerosis, ulcerative colitis and autoimmune hepatitis; infectious diseases, allergic diseases and cancer. Accordingly, the invention is further directed to pharmaceutical compositions comprising an antigen binding protein according to the invention and optionally one or more pharmaceutically acceptable excipients and/or carriers.

DETAILED DESCRIPTION OF THE INVENTION

Figure 1:
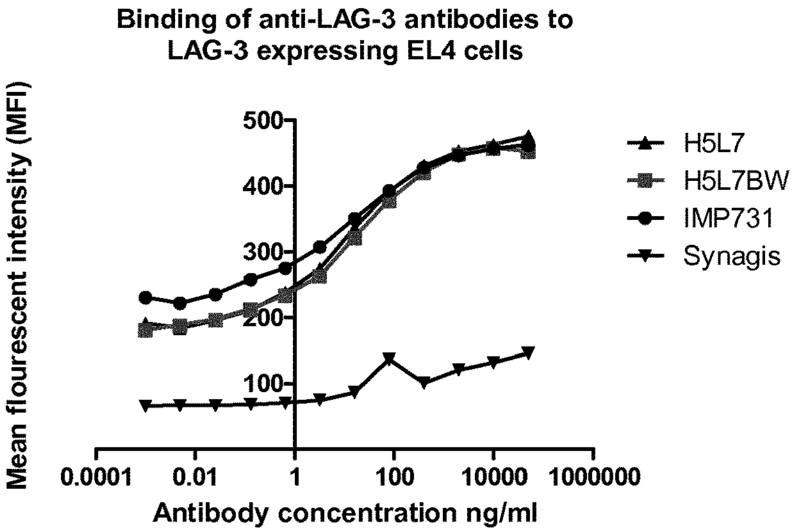
FIG. 1: Antibody binding to LAG-3 expressing EL4 (A) and activated human CD3+ T cells (B). Synagis, a monoclonal antibody against an unrelated target, was used as negative control.
Figure 1:
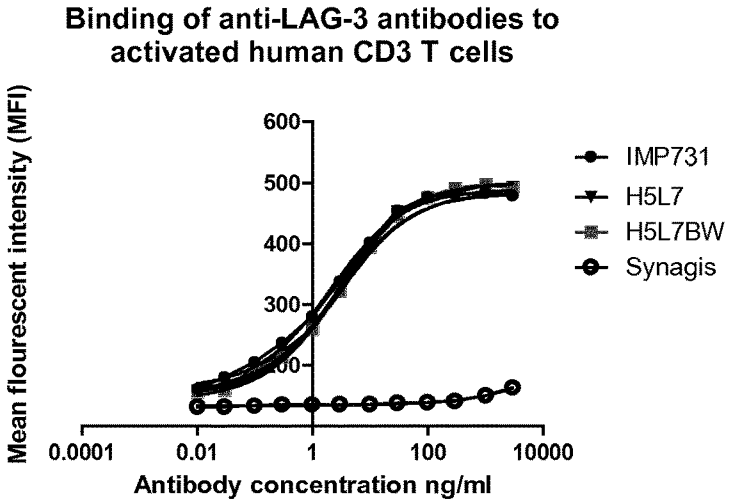

The present invention is broadly directed to antigen binding proteins that bind Lymphocyte Activation Gene 3 (LAG-3), and more particularly to antigen binding proteins that may cause depletion of LAG-3+ activated T cells.

The term "antigen binding protein" as used herein refers to antibodies and fragments thereof which are capable of binding to LAG-3. Unless otherwise specified, the term "LAG-3" as used herein refers to Lymphocyte Activation Gene 3. The term "LAG-3" includes within its scope, but is not limited to LAG-3 expressed as a dimer on the surface of, for example, activated T cells, NK cells and B cells (also known in the art as, for example, CD223) and a soluble form of LAG-3 found, for example, in human serum, referred to herein as "sLAG-3". Unless otherwise specified, references herein to "sLAG-3" and "LAG-3" are to human polypeptides. In a particular embodiment, the present invention provides antigen binding proteins capable of binding the form of LAG-3 expressed as a dimer on the surface of, for example, activated T cells, NK cells and B cells (also known in the art as, for example, CD223). More particularly, the present invention is directed to antigen binding proteins that are capable of binding LAG-3 expressed on activated T-cells and are able to cause depletion of said activated T cells.

In one aspect, the present invention provides an antigen binding protein capable of binding LAG-3 and which comprises CDRL1 from SEQ ID No. 5, wherein position 27E is proline.

In a further aspect, the present invention provides an antigen binding protein, which comprises CDRL1 of SEQ ID NO. 1.

In a further aspect, the present invention provides an antigen binding protein which is capable of binding LAG-3 and which comprises CDRL1 from SEQ ID NO. 5, wherein the antigen binding protein further comprises CDRL2 and/or CDRL3 from SEQ ID NO. 5, or a CDR variant thereof.

In a further aspect, the present invention provides an antigen binding protein further comprising CDRL2 of SEQ ID NO. 2 and/or CDRL3 of SEQ ID NO. 3 or a CDR variant thereof.

In a further aspect, the present invention provides an antigen binding protein which is capable of binding LAG-3 and which comprises CDRL1, CDRL2 and CDRL3 from SEQ ID NO. 5.

In a further aspect, the present invention provides an antigen binding protein comprising one or more of CDRH1, CDRH2 and CDRH3, or a CDR variant thereof, from SEQ ID NO 10.

In another aspect, the invention provides an antigen binding protein comprising a CDRL1, CDRL2 and CDRL3 from SEQ ID NO:5, and CDRH1, CDRH2 and CDRH3 from SEQ ID NO:10.

In a further aspect, the present invention provides an antigen binding protein comprising one or more CDRs, or a CDR variant thereof, selected from the group comprising CDRH1 of SEQ ID NO. 6, CDRH2 of SEQ ID NO. 7 and CDRH3 of SEQ ID NO. 8.

In a further aspect, the present invention provides an antigen binding protein comprising the following CDRs:

CDRL1: SEQ ID NO. 1
CDRL2: SEQ ID NO. 2
CDRL3: SEQ ID NO. 3
CDRH1: SEQ ID NO. 6
CDRH2: SEQ ID NO. 7
CDRH3: SEQ ID NO. 8.

In another aspect, the invention provides an antigen binding protein comprising a variable light chain comprising CDRL1, CDRL2 and CDRL3 from SEQ ID NO:5, and a variable heavy chain comprising CDRH1, CDRH2 and CDRH3 from SEQ ID NO:10.

In a particular aspect, the antigen binding protein is a humanised antibody, optionally an IgG.

The term "CDR" as used herein, refers to the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin.

It will be apparent to those skilled in the art that there are various numbering conventions for CDR sequences; Chothia (Chothia et al. (1989) Nature 342: 877-883), Kabat (Kabat et al., Sequences of Proteins of Immunological Interest, 4th Ed., U.S. Department of Health and Human Services, National Institutes of Health (1987)), AbM (University of Bath) and Contact (University College London). The minimum overlapping region using at least two of the Kabat, Chothia, AbM and contact methods can be determined to provide the "minimum binding unit". The minimum binding unit may be a sub-portion of a CDR. The structure and protein folding of the antibody may mean that other residues are considered part of the CDR sequence and would be understood to be so by a skilled person.

Unless otherwise stated and/or in absence of a specifically identified sequence, references herein to "CDR", "CDRL1", "CDRL2", "CDRL3", "CDRH1", "CDRH2", "CDRH3" refer to amino acid sequences numbered according to any of the known conventions identified in Table 1. In a particular embodiment, the numbering convention utilised is the Kabat convention. References herein to "position 27E" are to the amino acid present at position 27E in the light chain variable domain defined using the Kabat numbering convention. The skilled person will understand that this position has an equivalent under other known conventions, such as, for example, Chothia where position 27E is equivalent to position 30B.

Table 1 below represents one definition using each numbering convention for each CDR or binding unit. It should be noted that some of the CDR definitions may vary depending on the individual publication used.

TABLE 1

| | Kabat CDR | Chothia CDR | AbM CDR | Contact CDR | Minimum binding unit |
|---|---|---|---|---|---|
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

The term "CDR variant" as used herein, refers to a CDR that has been modified by at least one, for example 1, 2 or 3, amino acid substitution(s), deletion(s) or addition(s), wherein the modified antigen binding protein comprising the CDR variant substantially retains the biological characteristics of the antigen binding protein pre-modification. It will be appreciated that each CDR that can be modified may be modified alone or in combination with another CDR. In one aspect, the modification is a substitution, particularly a conservative substitution, for example as shown in Table 2.

TABLE 2

| Side chain | Members |
|---|---|
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

For example, in a variant CDR, the amino acid residues of the minimum binding unit may remain the same, but the flanking residues that comprise the CDR as part of the Kabat or Chothia definition(s) may be substituted with a conservative amino acid residue.

Such antigen binding proteins comprising modified CDRs or minimum binding units as described above may be referred to herein as "functional CDR variants" or "functional binding unit variants".

Antigen binding proteins of the present invention may be capable of binding sLAG-3. In one aspect, the equilibrium dissociation constant (KD) of the antigen binding protein-sLAG-3 interaction is 10 nM or less, such as 1 nM or less, for example between 1 pM and 300, 400, 500 pM or between 500 pM and 1 nM. A skilled person will appreciate that the smaller the KD numerical value, the stronger the binding. The reciprocal of KD (i.e. 1/KD) is the equilibrium association constant (KA) having units $M^{-1}$. A skilled person will appreciate that the larger the KA numerical value, the stronger the binding.

In one aspect, the present invention provides antigen binding proteins that are capable of binding recombinant LAG-3 with a KD of less than 1 nM, for example between 1 pM and 300 pM, when determined by Biacore™ surface Plasmon resonance analysis using recombinant human, or cynomolgus macaque LAG-3 extracellular domains (ECDs) of SEQ ID NOs: 51 and 52, respectively.

Furthermore, antigen binging proteins of the present invention may also be capable of binding LAG-3 expressed on, for example, EL4 cells or activated human CD3+ T cells.

Antigen binding proteins of the present invention may also be capable of depleting LAG-3+ activated T cells, in particular, CD4+LAG-3+ and CD8+LAG-3+ T cells. Depletion of LAG-3+ T cells may occur by, for example, antibody dependent cell mediated cytotoxic activity (ADCC) and/or complement-dependent cytotoxic activity (CDC).

In one aspect, the present invention provides antigen binding proteins that are capable of causing greater than 40% depletion of antigen specific CD4 and/or CD8 LAG-$3^+$ human T cells by ADCC in an in-vitro assay using primary human T cells.

In a further aspect, the present invention provides antigen binding proteins that, at a concentration of 0.1 μg/mL, are capable of causing greater than 50% depletion in an in vitro ADCC assay using europium-labelled LAG-3 expressing EL4 cells as target cells and human PBMCs as effector cells, wherein the effector: target ratio is no greater than 50:1 and the assay is run for a period of 2 hours. % cell lysis is calculated based on europium release from LAG-3 expressing EL4 cells.

The interaction between the constant region of an antigen binding protein and various Fc receptors (FcR) including FcγRI (CD64), FcγRII (CD32) and FcγRIII (CD16) is believed to mediate the effector functions, such as ADCC and CDC, of the antigen binding protein. Significant biological effects can be a consequence of effector functionality. Usually, the ability to mediate effector function requires binding of the antigen binding protein to an antigen and not all antigen binding proteins will mediate every effector function.

Effector function can be measured in a number of ways including for example via binding of the antigen binding protein, for example antibody, of the present invention via FcγRIII to Natural Killer cells or via FcγRI to monocytes/macrophages to measure for ADCC effector function. For example an antigen binding protein of the present invention can be assessed for ADCC effector function in a Natural Killer cell assay. Examples of such assays can be found in Shields et al, 2001 The Journal of Biological Chemistry, Vol. 276, p 6591-6604; Chappel et al, 1993 The Journal of Biological Chemistry, Vol 268, p 25124-25131; Lazar et al, 2006 PNAS, 103; 4005-4010.

Examples of assays to determine CDC function include those described in 1995 J Imm Meth 184:29-38.

In one aspect of the present invention, the antigen binding protein is an antibody.

The term "antibody" as used herein refers to molecules with an immunoglobulin-like domain and includes monoclonal (for example IgG, IgM, IgA, IgD or IgE), recombinant, polyclonal, chimeric, humanised, bispecific and heteroconjugate antibodies; a single variable domain (e.g., VL), a domain antibody (dAb®), antigen binding fragments, immunologically effective fragments, Fab, $F(ab')_2$, Fv, disulphide linked Fv, single chain Fv, closed conformation multispecific antibody, disulphide-linked scFv, diabodies, TANDABS™, etc. and modified versions of any of the foregoing (for a summary of alternative "antibody" formats see Holliger and Hudson, Nature Biotechnology, 2005, Vol 23, No. 9, 1126-1136). Alternative antibody formats include alternative scaffolds in which the one or more CDRs of any molecules in accordance with the disclosure can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain.

In a further aspect, the antigen binding protein is a humanised antibody.

A "humanised antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951.

In yet a further aspect, the humanised antibody has a human antibody constant region that is an IgG1, for example, the heavy chain constant region of SEQ ID No. 46.

It will be understood that the present invention further provides humanised antibodies which comprise a) a light chain sequence of SEQ ID NO. 5 or a light chain sequence with at least 75%, 80%, 85%, 90%, 95%, 96%, 97%, 98% or 99% identity to any of SEQ ID NO. 5 and b) a heavy chain sequence of SEQ ID NO. 10 or a heavy chain sequence with at least 75%, 80%, 85%, 90%, 95%, 96%, 97%, 98% or 99% identity to any of SEQ ID NO. 10.

In a further aspect, the present invention provides a humanised antibody, which comprises a) a light chain sequence with at least 90% identity to SEQ ID NO. 5, and b) a heavy chain sequence with at least 90% identity to SEQ ID NO. 10.

In a further aspect, the present invention provides a humanised antibody, which comprises a) a light chain sequence with at least 95% identity to SEQ ID NO. 5, and b) a heavy chain sequence with at least 95% identity to SEQ ID NO. 10.

In yet a further aspect, the present invention provides a humanised antibody, which comprises a) a light chain sequence with at least 97% identity to SEQ ID NO. 5, and b) a heavy chain sequence with at least 97% identity to SEQ ID NO. 10.

In yet a further aspect, the present invention provides a humanised antibody, which comprises a) a light chain sequence of SEQ ID NO. 5, and b) a heavy chain sequence of SEQ ID NO. 10.

It will be understood that the present invention further provides humanised antibodies which comprise a) a light chain sequence of SEQ ID NO. 35 or a light chain sequence with at least 75%, 80%, 85%, 90%, 95%, 96%, 97%, 98% or 99% identity to any of SEQ ID NO. 35 and b) a heavy chain sequence of SEQ ID NO. 36 or a heavy chain sequence with at least 75%, 80%, 85%, 90%, 95%, 96%, 97%, 98% or 99% identity to any of SEQ ID NO. 36.

In a further aspect, the present invention provides antigen binding proteins comprising CDRL1-L3 and CDRH1-H3 of SEQ ID NO: 35 and 36, respectively.

For nucleotide and amino acid sequences, the term "identical" or "identity" indicates the degree of identity between two nucleic acid or two amino acid sequences when optimally aligned and compared with appropriate insertions or deletions.

The percent identity between two sequences is a function of the number of identical positions shared by the sequences (i.e., % identity=number of identical positions/total number of positions multiplied by 100), taking into account the number of gaps, and the length of each gap, which need to be introduced for optimal alignment of the two sequences. The comparison of sequences and determination of percent identity between two sequences can be accomplished using a mathematical algorithm, as described below.

Percent identity between a query nucleic acid sequence and a subject nucleic acid sequence is the "Identities" value, expressed as a percentage, which is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein.

Percent identity between a query amino acid sequence and a subject amino acid sequence is the "Identities" value, expressed as a percentage, which is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query amino acid sequence may be described by an amino acid sequence identified in one or more claims herein.

Production

The antigen binding proteins, for example antibodies, such as humanised antibodies of the present invention may be produced by transfection of a host cell with an expression vector comprising the coding sequence(s) for the antigen binding protein of the invention. An expression vector or recombinant plasmid is produced by placing these coding sequences for the antigen binding protein in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antigen binding protein light or heavy chain. In certain embodiments this second expression vector is identical to the first except insofar as the coding sequences and selectable markers are concerned, so to ensure as far as possible that each polypeptide chain is functionally expressed. Alternatively, the heavy and light chain coding sequences for the antigen binding protein may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antigen binding protein of the invention. The antigen binding protein which includes the association of both the recombinant heavy chain and/or light chain is screened from culture by appropriate assay, such as ELISA or RIA. Similar conventional techniques may be employed to construct other antigen binding proteins.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antigen binding proteins of the present invention. Host cells useful for the cloning and other manipulations of these cloning vectors are also conventional. However, cells from various strains of *E. coli* may be used for replication of the cloning vectors and other steps in the construction of antigen binding proteins of this invention.

Suitable host cells or cell lines for the expression of the antigen binding proteins of the invention include mammalian cells such as NS0, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs or other embodiments of the present invention (see, e.g., Plückthun, A., Immunol. Rev., 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host, or in alternative embodiments the molecule may express in the bacterial host and then be subsequently re-folded. For example, various strains of *E. coli* used for expression are well-known as host cells in the field of biotechnology. Various strains of *B. subtilis, Streptomyces*, other bacilli and the like may also be employed in this method.

Where desired, strains of yeast cells known to those skilled in the art are also available as host cells, as well as insect cells, e.g. *Drosophila* and *Lepidoptera* and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antigen binding protein of the invention from such host cell may all be conventional techniques. Typically, the culture method of the present invention is a serum-free culture method, usually by culturing cells serum-free in suspension. Likewise, once produced, the antigen binding proteins of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparations of altered antibodies are described in WO 99/58679 and WO 96/16990.

Yet another method of expression of the antigen binding proteins may utilize expression in a transgenic animal, such as described in U.S. Pat. No. 4,873,316. This relates to an expression system using the animals casein promoter which when transgenically incorporated into a mammal permits the female to produce the desired recombinant protein in its milk.

In a further aspect of the invention there is provided a method of producing an antigen binding protein (e.g. a humanised antibody) of the invention which method comprises the step of culturing a host cell transformed or transfected with a vector encoding the light and/or heavy chain of the antibody of the invention and recovering the antigen binding protein thereby produced.

In accordance with the present invention there is provided a method of producing an anti-LAG-3 antigen binding protein (e.g. a humanised antibody) of the present invention which binds to human LAG-3, which method comprises the steps of;

(a) providing a first vector encoding a heavy chain of the antibody;
(b) providing a second vector encoding a light chain of the antibody;
(c) transforming a mammalian host cell (e.g. CHO) with said first and second vectors;
(d) culturing the host cell of step (c) under conditions conducive to the secretion of the antibody from said host cell into said culture media;
(e) recovering the secreted antibody of step (d).

Once expressed by the desired method, the antigen binding protein may then be examined for in vitro activity by use of an appropriate assay, such as Biacore™ surface Plasmon resonance analysis, to assess binding of the antigen binding protein to LAG-3. Additionally, other in vitro and in vivo assays may also be used to determine an antigen binding protein's ability to cause depletion of cells expressing LAG-3, such as activated human T cell populations.

The skilled person will appreciate that, upon production of an antigen binding protein such as an antibody, in particular depending on the cell line used and particular amino acid sequence of the antigen binding protein, post-translational modifications may occur. For example, this may include the cleavage of certain leader sequences, the addition of various sugar moieties in various glycosylation and phosphorylation patterns, deamidation, oxidation, disulfide bond scrambling, isomerisation, C-terminal lysine clipping, and N-terminal glutamine cyclisation. The present invention encompasses the use of antigen binding proteins which have been subjected to, or have undergone, one or more post-translational modifications. Thus an "antigen binding protein" or "antibody" of the invention includes an "antigen binding protein" or "antibody", respectively, as defined earlier which has undergone a post-translational modification such as described herein.

Glycosylation of antibodies at conserved positions in their constant regions is known to have a profound effect on antibody function, particularly effector functioning, see for example, Boyd et al. (1996) Mol. Immunol. 32: 1311-1318. Glycosylation variants of the antigen binding proteins of the invention wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al. (2001) Biochemistry 40: 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms, see Zhang et al. (2004) Science 303: 371: Sears et al. (2001) Science 291: 2344; Wacker et al. (2002) Science 298: 1790; Davis et al. (2002) Chem. Rev. 102: 579; Hang et al. (2001) Acc. Chem. Res 34: 727. The antibodies (for example of the IgG isotype, e.g. IgG1) as herein described may comprise a defined number (e.g. 7 or less, for example 5 or less, such as two or a single) of glycoform(s).

Deamidation is an enzymatic reaction primarily converting asparagine (N) to iso-aspartic acid and aspartic acid (D) at approximately 3:1 ratio. To a much lesser degree, deamidation can occur with glutamine residues in a similar manner. Deamidation in a CDR results in a change in charge of the molecule, but typically does not result in a change in antigen binding, nor does it impact on PK/PD.

Oxidation can occur during production and storage (i.e. in the presence of oxidizing conditions) and results in a covalent modification of a protein, induced either directly by reactive oxygen species or indirectly by reaction with secondary by-products of oxidative stress. Oxidation happens primarily with methionine residues, but occasionally can occur at tryptophan and free cysteine residues.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

Isomerization typically occurs during production, purification, and storage (at acidic pH) and usually occurs when aspartic acid is converted to isoaspartic acid through a chemical process.

N-terminal glutamine in the heavy chain and/or light chain is likely to form pyroglutamate (pGlu). Most pGlu formation happens in the production bioreactor, but it can be formed non-enzymatically, depending on pH and temperature of processing and storage conditions. pGlu formation is considered as one of the principal degradation pathways for recombinant mAbs.

C-terminal lysine clipping is an enzymatic reaction catalyzed by carboxypeptidases, and is commonly observed in recombinant mAbs. Variants of this process include removal of lysine from one or both heavy chains. Lysine clipping does not appear to impact bioactivity and has no effect on mAb effector function.

Effector Function Enhancement

The interaction between the constant region of an antigen binding protein and various Fc receptors (FcR) including FcγRI (CD64), FcγRII (CD32) and FcγRIII (CD16) is believed to mediate the effector functions, such as ADCC and CDC, of the antigen binding protein.

The term "Effector Function" as used herein is meant to refer to one or more of Antibody dependant cell mediated cytotoxic activity (ADCC), Complement-dependant cytotoxic activity (CDC) mediated responses, Fc-mediated phagocytosis or antibody dependant cellular phagocytosis (ADCP) and antibody recycling via the FcRn receptor.

The ADCC or CDC properties of antigen binding proteins of the present invention may be enhanced in a number of ways.

Human IgG1 constant regions containing specific mutations or altered glycosylation on residue Asn297 have been shown to enhance binding to Fc receptors. In some cases these mutations have also been shown to enhance ADCC and CDC (Lazar et al. PNAS 2006, 103; 4005-4010; Shields et al. J Biol Chem 2001, 276; 6591-6604; Nechansky et al. Mol Immunol, 2007, 44; 1815-1817).

In one embodiment of the present invention, such mutations are in one or more of positions selected from 239, 332 and 330 (IgG1), or the equivalent positions in other IgG isotypes. Examples of suitable mutations are S239D and I332E and A330L. In one embodiment, the antigen binding protein of the invention herein described is mutated at positions 239 and 332, for example S239D and I332E or in a further embodiment it is mutated at three or more positions selected from 239 and 332 and 330, for example S239D and I332E and A330L. (EU index numbering).

In one embodiment of the present invention, there is provided an antigen binding protein comprising a chimeric heavy chain constant region for example an antigen binding protein comprising a chimeric heavy chain constant region with at least one CH2 domain from IgG3 such that the antigen binding protein has enhanced effector function, for example wherein it has enhanced ADCC or enhanced CDC, or enhanced ADCC and CDC functions. In one such embodiment, the antigen binding protein may comprise one CH2 domain from IgG3 or both CH2 domains may be from IgG3.

Also provided is a method of producing an antigen binding protein according to the invention comprising the steps of:

a) culturing a recombinant host cell comprising an expression vector comprising an isolated nucleic acid as described herein wherein the expression vector comprises a nucleic acid sequence encoding a Fc region containing domains derived from human germline IgG1 and IgG3 sequences; and b) recovering the antigen binding protein.

Such methods for the production of antigen binding proteins can be performed, for example, using the COMPLEGENT™ technology system available from BioWa, Inc. (La Jolla, Calif., USA) and Kyowa Hakko Kogyo (now, Kyowa Hakko Kirin Co., Ltd.) Co., Ltd. in which a recombinant host cell comprising an expression vector in which a nucleic acid sequence encoding a Fc region containing domains derived from human germline IgG1 and IgG3 sequences is expressed to produce an antigen binding protein having enhanced complement dependent cytotoxicity (CDC) activity that is increased relative to an otherwise identical antigen binding protein lacking such a chimeric Fc domain. Aspects of the COMPLEGENT™ technology system are described in WO2007011041 and US20070148165 each of which are incorporated herein by reference. In an alternative embodiment CDC activity may be increased by introducing sequence specific mutations into the Fc region of an IgG chain. Those of ordinary skill in the art will also recognize other appropriate systems.

In an alternative embodiment of the present invention, there is provided an antigen binding protein comprising a heavy chain constant region with an altered glycosylation profile such that the antigen binding protein has enhanced effector function. For example, wherein the antigen binding protein has enhanced ADCC or enhanced CDC or wherein it has both enhanced ADCC and CDC effector function. Examples of suitable methodologies to produce antigen binding proteins with an altered glycosylation profile are described in WO2003011878, WO2006014679 and EP1229125, all of which can be applied to the antigen binding proteins of the present invention.

The present invention also provides a method for the production of an antigen binding protein according to the invention comprising the steps of:

a) culturing a recombinant host cell comprising an expression vector comprising the isolated nucleic acid as described herein under conditions suitable to express the antigen binding protein, wherein the FUT8 gene encoding alpha-1,6-fucosyltransferase has been inactivated in the recombinant host cell; and b) isolating the antigen binding protein produced by the recombinant host cell.

The present invention also provides a method for the production of an antigen binding protein according to the invention comprising the steps of:

a) expressing an antigen binding protein according to the invention in a recombinant host cell, wherein the FUT8 gene encoding alpha-1,6-fucosyltransferase is been inactivated in the recombinant host cell; and b) isolating the antigen binding protein produced by the recombinant host cell.

Such methods for the production of antigen binding proteins can be performed, for example, using the POTELLIGENT™ technology system available from BioWa, Inc. (La Jolla, Calif., USA) in which CHOK1SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. No. 7,214,775, U.S. Pat. No. 6,946,292, WO0061739 and WO0231240 all of which are incorporated herein by reference. Those of ordinary skill in the art will also recognize other appropriate systems.

In a further aspect, the present invention provides non-fucosylated antibodies. References herein to "non-fucosylated" or "afucosylated" antibodies refer to antibodies that harbour a tri-mannosyl core structure of complex-type N-glycans of Fc without fucose residue. Non-fucosylated or afucosylated antibodies of the present invention do not comprise fucose on the core carbohydrate structure attached to Asn297. These glycoengineered antibodies that lack core fucose residue from the Fc N-glycans may exhibit stronger ADCC than fucosylated equivalents due to enhancement of FcγRIIIa binding capacity.

It will be apparent to those skilled in the art that such modifications may not only be used alone but may be used in combination with each other in order to further enhance effector function.

In one such embodiment of the present invention there is provided an antigen binding protein comprising a heavy chain constant region which comprises a mutated and chimeric heavy chain constant region. For example, wherein an antigen binding protein comprising at least one CH2 domain from human IgG3 and one CH2 domain from human IgG1, wherein the IgG1 CH2 domain has one or more mutations at positions selected from 239 and 332 and 330 (for example the mutations may be selected from S239D and I332E and A330L) such that the antigen binding protein has enhanced effector function. In this context, enhanced effector function may equate to, for example, having enhanced ADCC or enhanced CDC, for example wherein it has enhanced ADCC and enhanced CDC. In one embodiment the IgG1 CH2 domain has the mutations S239D and 1332E.

In an alternative embodiment of the present invention there is provided an antigen binding protein comprising a chimeric heavy chain constant region and which has an altered glycosylation profile. In one such embodiment the heavy chain constant region comprises at least one CH2 domain from IgG3 and one CH2 domain from IgG1 and has an altered glycosylation profile such that the ratio of fucose to mannose is 0.8:3 or less, for example wherein the antigen binding protein is defucosylated so that said antigen binding protein has an enhanced effector function in comparison with an equivalent antigen binding protein with an immunoglobulin heavy chain constant region lacking said mutations and altered glycosylation profile, for example wherein it has one or more of the following functions, enhanced ADCC or enhanced CDC, for example wherein it has enhanced ADCC and enhanced CDC.

In an alternative embodiment the antigen binding protein has at least one human IgG3 CH2 domain and at least one heavy chain constant domain from human IgG1 wherein both IgG CH2 domains are mutated in accordance with the limitations described herein.

In one aspect of the invention there is provided a method of producing an antigen binding protein according to the invention described herein comprising the steps of:

a) culturing a recombinant host cell containing an expression vector containing an isolated nucleic acid as described herein, said expression vector further comprising a Fc nucleic acid sequence encoding a Fc region containing domains derived from human germline IgG1 and IgG3 sequences, and wherein the FUT8 gene encoding alpha-1, 6-fucosyltransferase has been inactivated in the recombinant host cell; and b) recovering the antigen binding protein.

Such methods for the production of antigen binding proteins can be performed, for example, using the AccretaMab™ technology system available from BioWa, Inc. (La Jolla, Calif., USA) which combines the POTELLIGENT™ and COMPLEGENT™ technology systems to produce an antigen binding protein having both ADCC and CDC enhanced activity that is increased relative to an otherwise identical monoclonal antibody lacking a chimeric Fc domain and which has fucose on the oligosaccharide In yet another embodiment of the present invention there is provided an antigen binding protein comprising a mutated and chimeric heavy chain constant region wherein said antigen binding protein has an altered glycosylation profile such that the antigen binding protein has enhanced effector function, for example wherein it has one or more of the following functions, enhanced ADCC or enhanced CDC. In one embodiment the mutations are selected from positions 239 and 332 and 330, for example the mutations are selected from S239D and I332E and A330L. In a further embodiment the heavy chain constant region comprises at least one CH2 domain from human IgG3 and one Ch2 domain from human IgG1. In one embodiment the heavy chain constant region has an altered glycosylation profile such that the ratio of fucose to mannose is 0.8:3 or less for example the antigen binding protein is defucosylated, so that said antigen binding protein has an enhanced effector function in comparison with an equivalent non-chimeric antigen binding protein or with an immunoglobulin heavy chain constant region lacking said mutations and altered glycosylation profile.

Half-Life Extension

Increased half-life, or half-life extension, can be useful in in vivo applications of antigen binding proteins, especially antibodies and most especially antibody fragments of small size. Such fragments (Fvs, disulphide bonded Fvs, Fabs, scFvs, dAbs) are generally rapidly cleared from the body. Antigen binding proteins in accordance with the disclosure can be adapted or modified to provide increased serum half-life in vivo and consequently longer persistence, or residence, times of the functional activity of the antigen binding protein in the body. Suitably, such modified molecules have a decreased clearance and increased Mean Residence Time compared to the non-adapted molecule. Increased half-life can improve the pharmacokinetic and pharmacodynamic properties of a therapeutic molecule and can also be important for improved patient compliance.

The phrases, "half-life" ("$t_{1/2}$") and "serum half life", refer to the time taken for the serum (or plasma) concentration of an antigen binding protein in accordance with the disclosure to reduce by 50%, in vivo, for example due to degradation of the antigen binding protein and/or clearance or sequestration of the antigen binding protein by natural mechanisms.

The antigen binding proteins of the disclosure can be stabilized in vivo and their half-life increased by binding to molecules which resist degradation and/or clearance or sequestration ("half-life extending moiety" or "half-life extending molecule"). Half-life extension strategies are reviewed, for example, in "*Therapeutic Proteins: Strategies to Modulate Their Plasma Half-Lives*", Edited by Roland Kontermann, Wiley-Blackwell, 2012, ISBN: 978-3-527-32849-9. Suitable half-life extension strategies include: PEGylation, polysialylation, HESylation, recombinant PEG mimetics, N-glycosylation, O-glycosylation, Fc fusion, engineered Fc, IgG binding, albumin fusion, albumin binding, albumin coupling and nanoparticles.

In one embodiment, the half-life extending moiety or molecule is a polyethylene glycol moiety or a PEG mimetic. In one embodiment, the antigen binding protein comprises (optionally consists of) a single variable domain of the disclosure linked to a polyethylene glycol moiety (optionally, wherein said moiety has a size of about 20 to about 50 kDa, optionally about 40 kDa linear or branched PEG). Reference is made to WO04081026 for more detail on PEGylation of domain antibodies and binding moieties. In one embodiment, the antagonist consists of a domain antibody monomer linked to a PEG, wherein the domain antibody monomer is a single variable domain according to the disclosure. Suitable PEG mimetics are reviewed, for example in Chapter 4, pages 63-80, "*Therapeutic Proteins: Strategies to Modulate Their Plasma Half-Lives*" Edited by Roland Kontermann, Wiley-Blackwell, 2012, ISBN: 978-3-527-32849-9.

The interaction between the Fc region of an antibody and various Fc receptors (FcγR) is believed to mediate phagocytosis and half-life/clearance of an antibody or antibody fragment. The neonatal FcRn receptor is believed to be involved in both antibody clearance and the transcytosis across tissues (see Junghans (1997) Immunol. Res 16: 29-57; and Ghetie et al. (2000) Annu. Rev. Immunol. 18: 739-766). In one embodiment, the half-life extending moiety may be an Fc region from an antibody. Such an Fc region may incorporate various modifications depending on the desired property. For example, a salvage receptor binding epitope may be incorporated into the antibody to increase serum half life, see U.S. Pat. No. 5,739,277.

Human IgG1 residues determined to interact directly with human FcRn includes Ile253, Ser254, Lys288, Thr307, Gln311, Asn434 and His435. Accordingly, substitutions at any of the positions described in this section may enable increased serum half-life and/or altered effector properties of the antibodies.

Half-life extension by fusion to the Fc region is reviewed, for example, in Chapter 9, pages 157-188, *"Therapeutic Proteins: Strategies to Modulate Their Plasma Half-Lives"* Edited by Roland Kontermann, Wiley-Blackwell, 2012, ISBN: 978-3-527-32849-9.

Typically, a polypeptide that enhances serum half-life in vivo, i.e. a half-life extending molecule, is a polypeptide which occurs naturally in vivo and which resists degradation or removal by endogenous mechanisms which remove unwanted material from the organism (e.g., human). Typically, such molecules are naturally occurring proteins which themselves have a long half-life in vivo.

For example, a polypeptide that enhances serum half-life in vivo can be selected from proteins from the extracellular matrix, proteins found in blood, proteins found at the blood brain barrier or in neural tissue, proteins localized to the kidney, liver, muscle, lung, heart, skin or bone, stress proteins, disease-specific proteins, or proteins involved in Fc transport. Suitable polypeptides are described, for example, in WO2008/096158.

Such an approach can also be used for targeted delivery of an antigen binding protein, e.g. a single variable domain, in accordance with the disclosure to a tissue of interest. In one embodiment targeted delivery of a high affinity single variable domain in accordance with the disclosure is provided.

In one embodiment, an antigen binding protein, e.g. single variable domain, in accordance with the disclosure can be linked, i.e. conjugated or associated, to serum albumin, fragments and analogues thereof. Half-life extension by fusion to albumin is reviewed, for example in Chapter 12, pages 223-247, *"Therapeutic Proteins: Strategies to Modulate Their Plasma Half-Lives"* Edited by Roland Kontermann, Wiley-Blackwell, 2012, ISBN: 978-3-527-32849-9.

Examples of suitable albumin, albumin fragments or albumin variants are described, for example, in WO2005077042 and WO2003076567.

In another embodiment, a single variable domain, polypeptide or ligand in accordance with the disclosure can be linked, i.e. conjugated or associated, to transferrin, fragments and analogues thereof.

In one embodiment, half-life extension can be achieved by targeting an antigen or epitope that increases half-live in vivo. The hydrodynamic size of an antigen binding protein and its serum half-life may be increased by conjugating or associating an antigen binding protein of the disclosure to a binding domain that binds a naturally occurring molecule and increases half-live in vivo.

For example, the antigen binding protein in accordance with the invention can be conjugated or linked to an anti-serum albumin or anti-neonatal Fc receptor antibody or antibody fragment, e.g. an anti-SA or anti-neonatal Fc receptor dAb, Fab, Fab' or scFv, or to an anti-SA affibody or anti-neonatal Fc receptor Affibody or an anti-SA avimer, or an anti-SA binding domain which comprises a scaffold selected from, but not limited to, the group consisting of CTLA-4, lipocallin, SpA, an affibody, an avimer, GroEl and fibronectin (see WO2008096158 for disclosure of these binding domains). Conjugating refers to a composition comprising polypeptide, dAb or antagonist of the disclosure that is bonded (covalently or noncovalently) to a binding domain such as a binding domain that binds serum albumin.

In another embodiment, the binding domain may be a polypeptide domain such as an Albumin Binding Domain (ABD) or a small molecule which binds albumin (reviewed, for example in Chapter 14, pages 269-283 and Chapter 15, pages 285-296, *"Therapeutic Proteins: Strategies to Modulate Their Plasma Half-Lives"* Edited by Roland Kontermann, Wiley-Blackwell, 2012, ISBN: 978-3-527-32849-9).

In one embodiment, there is provided a fusion protein comprising an antigen binding protein in accordance with the invention and an anti-serum albumin or anti-neonatal Fc receptor antibody or antibody fragment.

The long half-life of IgG antibodies is reported to be dependent on its binding to FcRn. Therefore, substitutions that increase the binding affinity of IgG to FcRn at pH 6.0 while maintaining the pH dependence of the interaction by engineering the constant region have been extensively studied (Ghetie et al., Nature Biotech. 15: 637-640, 1997; Hinton et al., JBC 279: 6213-6216, 2004; Dall'Acqua et al., 10 J Immunol 117: 1129-1138, 2006). Another means of modifying antigen binding proteins of the present invention involves increasing the in-vivo half life of such proteins by modification of the immunoglobulin constant domain or FcRn (Fc receptor neonate) binding domain.

In adult mammals, FcRn, also known as the neonatal Fc receptor, plays a key role in maintaining serum antibody levels by acting as a protective receptor that binds and salvages antibodies of the IgG isotype from degradation. IgG molecules are endocytosed by endothelial cells, and if they bind to FcRn, are recycled out into circulation. In contrast, IgG molecules that do not bind to FcRn enter the cells and are targeted to the lysosomal pathway where they are degraded.

The neonatal FcRn receptor is believed to be involved in both antibody clearance and the transcytosis across tissues (see Junghans R. P (1997) Immunol. Res 16. 29-57 and Ghetie et al (2000) Annu. Rev. Immunol. 18, 739-766). Human IgG1 residues determined to interact directly with human FcRn includes Ile253, Ser254, Lys288, Thr307, Gln311, Asn434 and His435. Switches at any of these positions described in this section may enable increased serum half-life and/or altered effector properties of antigen binding proteins of the invention.

Antigen binding proteins of the present invention may have amino acid modifications that increase the affinity of the constant domain or fragment thereof for FcRn. Increasing the half-life of therapeutic and diagnostic IgG's and other bioactive molecules has many benefits including reducing the amount and/or frequency of dosing of these molecules. In one embodiment there is therefore provided an antigen binding according to the invention provided herein or a fusion protein comprising all or a portion (an FcRn binding portion) of an IgG constant domain having one or more of these amino acid modifications and a non-IgG protein or non-protein molecule conjugated to such a modified IgG constant domain, wherein the presence of the modified IgG constant domain increases the in vivo half life of the antigen binding protein.

PCT Publication No. WO 00/42072 discloses a polypeptide comprising a variant Fc region with altered FcRn binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386, 388, 400, 413, 415, 424, 433, 434, 435, 436, 439, and 447 of the Fc region, wherein the numbering of the residues in the Fc region is that of the EU index (Kabat et al).

PCT Publication No. WO 02/060919 A2 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more of positions 251, 253, 255, 285-290, 308-314, 385-389, and 428-435.

Shields et al. (2001, J Biol Chem; 276:6591-604) used alanine scanning mutagenesis to alter residues in the Fc region of a human IgG1 antibody and then assessed the binding to human FcRn. Positions that effectively abrogated binding to FcRn when changed to alanine include I253, S254, H435, and Y436. Other positions showed a less pronounced reduction in binding as follows: E233-G236, R255, K288, L309, S415, and H433. Several amino acid positions exhibited an improvement in FcRn binding when changed to alanine; notable among these are P238, T256, E272, V305, T307, Q311, D312, K317, D376, E380, E382, S424, and N434. Many other amino acid positions exhibited a slight improvement (D265, N286, V303, K360, Q362, and A378) or no change (S239, K246, K248, D249, M252, E258, T260, S267, H268, S269, D270, K274, N276, Y278, D280, V282, E283, H285, T289, K290, R292, E293, E294, Q295, Y296, N297, S298, R301, N315, E318, K320, K322, S324, K326, A327, P329, P331, E333, K334, T335, S337, K338, K340, Q342, R344, E345, Q345, Q347, R356, M358, T359, K360, N361, Y373, S375, S383, N384, Q386, E388, N389, N390, K392, L398, S400, D401, K414, R416, Q418, Q419, N421, V422, E430, T437, K439, S440, S442, S444, and K447) in FcRn binding.

The most pronounced effect was found for combination variants with improved binding to FcRn. At pH 6.0, the E380A/N434A variant showed over 8-fold better binding to FcRn, relative to native IgG1, compared with 2-fold for E380A and 3.5-fold for N434A. Adding T307A to this effected a 12-fold improvement in binding relative to native IgG1. In one embodiment the antigen binding protein of the invention comprises the E380A/N434A mutations and has increased binding to FcRn.

Dall'Acqua et al. (2002, J Immunol.; 169:5171-80) described random mutagenesis and screening of human IgG1 hinge-Fc fragment phage display libraries against mouse FcRn. They disclosed random mutagenesis of positions 251, 252, 254-256, 308, 309, 311, 312, 314, 385-387, 389, 428, 433, 434, and 436. The major improvements in IgG1-human FcRn complex stability occur in substituting residues located in a band across the Fc-FcRn interface (M252, S254, T256, H433, N434, and Y436) and to lesser extend substitutions of residues at the periphery like V308, L309, Q311, G385, Q386, P387, and N389. The variant with the highest affinity to human FcRn was obtained by combining the M252Y/S254T/T256E and H433K/N434F/Y436H mutations and exhibited a 57-fold increase in affinity relative to the wild-type IgG1. The in vivo behaviour of such a mutated human IgG1 exhibited a nearly 4-fold increase in serum half-life in cynomolgus monkey as compared to wild-type IgG1.

The present invention therefore provides a variant of an antigen binding protein with optimized binding to FcRn. In a preferred embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat.

In a further aspect of the invention the modifications are M252Y/S254T/T256E.

Additionally, various publications describe methods for obtaining physiologically active molecules whose half-lives are modified either by introducing an FcRn-binding polypeptide into the molecules (WO 97/43316; U.S. Pat. No. 5,869,046; U.S. Pat. No. 5,747,035; WO 96/32478; WO 91/14438) or by fusing the molecules with antibodies whose FcRn-binding affinities are preserved but affinities for other Fc receptors have been greatly reduced (WO 99/43713) or fusing with FcRn binding domains of antibodies (WO 00/09560; U.S. Pat. No. 4,703,039).

Although substitutions in the constant region are able to significantly improve the functions of therapeutic IgG antibodies, substitutions in the strictly conserved constant region have the risk of immunogenicity in human (Presta, supra, 2008; De Groot and Martin, Clin Immunol 131: 189-201, 2009) and substitution in the highly diverse variable region sequence might be less immunogenic. Reports concerned with the variable region include engineering the CDR residues to improve binding affinity to the antigen (Rothe et al., Expert Opin Biol Ther 6: 177-187, 2006; Bostrom et al., Methods Mol Bioi 525: 353-376, 2009; Thie et al., Methods Mol Biol 525: 309-322, 2009) and engineering the CDR and framework residues to improve stability (Worn and Pluckthun, J Mol Biol 305: 989-1010, 2001; Ewert et al., Methods 34: 184-199, 2004) and decrease immunogenicity risk (De Groot and Martin, supra, 2009; Jones et al., Methods Mol Biol 525: 405-423, xiv, 2009). As reported, improved affinity to the antigen can be achieved by affinity maturation using the phage or ribosome display of a randomized library.

Improved stability can be rationally obtained from sequence- and structure-based rational design. Decreased immunogenicity risk (deimmunization) can be accomplished by various humanization methodologies and the removal of T-cell epitopes, which can be predicted using in silico technologies or determined by in vitro assays. Additionally, variable regions have been engineered to lower pI. A longer half life was observed for these antibodies as compared to wild type antibodies despite comparable FcRn binding. Engineering or selecting antibodies with pH dependent antigen binding to modify antibody and/or antigen half life eg IgG2 antibody half life can be shortened if antigen-mediated clearance mechanisms normally degrade the antibody when bound to the antigen. Similarly, the antigen: antibody complex can impact the half-life of the antigen, either extending half-life by protecting the antigen from the typical degradation processes, or shortening the half-life via antibody-mediated degradation. One embodiment relates to antibodies with higher affinity for antigen at pH 7.4 as compared to endosomal pH (i.e., pH 5.5-6.0) such that the KD ratio at pH5.5/pH 7.4 or at pH 6.0/pH 7.4 is 2 or more. For example to enhance the pharmacokinetic (PK) and pharmacodynamic (PD) properties of the antibody, it is possible to engineer pH-sensitive binding to the antibody by introducing histidines into CDR residues.

Pharmaceutical Compositions

The antigen binding proteins of the present invention will normally, but not necessarily, be formulated into pharmaceutical compositions prior to administration to a patient. Accordingly, in another aspect of the invention there is provided a pharmaceutical composition comprising an antigen binding protein according to the invention and one or more pharmaceutically acceptable excipients and/or carriers.

Methods for the preparation of such pharmaceutical compositions are well known to those skilled in the art (e.g. Remingtons Pharmaceutical Sciences, 16th edition (1980) Mack Publishing Co and Pharmaceutical Biotechnology; Plenum publishing corporation; Volumes 2, 5 and 9).

The antigen binding proteins of the present invention may be formulated for administration in any convenient way. Pharmaceutical compositions may, for example, be administered by injection or continuous infusion (examples include, but are not limited to, intravenous, intraperitoneal, intradermal, subcutaneous, intramuscular and intraportal). In one embodiment, the composition is suitable for subcutaneous injection.

Pharmaceutical compositions may be suitable for topical administration (which includes, but is not limited to, epicutaneous, inhaled, intranasal or ocular administration) or enteral administration (which includes, but is not limited to, oral or rectal administration).

Pharmaceutical compositions may comprise between 0.0001 mg/kg to 10 mg/kg of antigen binding protein, for example between 0.1 mg/kg and 5 mg/kg of antigen binding protein. Alternatively, the composition may comprise between 1.0 mg/kg and 3.0 mg/kg.

Pharmaceutical compositions may comprise, in addition to an antigen binding protein of the present invention, one or more other therapeutic agents. Additional therapeutic agents that may be combined with an antigen binding protein of the present invention include, but are not limited to, anti-CTLA-4 (e.g. ipilimumab and tremelimumab), anti-TIM-3, anti-OX40, anti-OX40L, anti-PD1 (e.g nivolumab, lambrolizumab), anti-PD1L, anti-GITR, anti-IL-5 (e.g. mepolizumab), anti-B-Lymphocyte cell activating (BLyS) factor (e.g. belimumab), anti-GITRL, anti-IL-7, anti-IL-7R, anti-CD20, anti-CCL20, anti-TNFα, anti-OSM and anti-IL-6 antibodies, as well as inhibitors of JAK, CCR9, RIP kinases, BET proteins, RORγ1 and thiopurines.

The antigen binding proteins of the present invention and one or more other therapeutic agents for combination therapy may be formulated together in the same composition or presented in separate compositions. Separately presented compositions may be administered simultaneously or sequentially.

Methods of Use

The antigen binding proteins described herein may have use in therapy. Antigen binding proteins of the present invention that bind Lymphocyte Activation Gene 3 (LAG-3) and cause depletion of LAG-3+ activated T cells may have use in the treatment or prevention of diseases associated with the involvement of pathogenic T cells, such as autoimmune diseases, infectious diseases, allergic diseases and cancer.

Examples of disease states in which the antigen binding proteins have potentially beneficial effects include autoimmune diseases including, but not limited to psoriasis, inflammatory bowel disease (for example Crohn's disease and/or ulcerative colitis), rheumatoid arthritis, primary biliary cirrhosis, systemic lupus erythematosus (SLE), Sjögren's syndrome, multiple sclerosis, autoimmune hepatitis, uveitis, type I diabetes ankylosing spondylitis, psoriatic arthritis, Grave's disease, graft versus host disease, treatment and/or prevention of organ transplant rejection, e.g. renal or liver transplant rejection, primary sclerosing cholangitis, sarcoidosis, vasculitis, nephritis, autoimmune thrombocytopenic purpura, systemic sclerosis, celiac disease, anti-phospholipid antibody syndrome, alopecia areata and myasthenia gravis; infectious diseases including, but not limited to, hepatitis C, hepatitis B, HIV, tuberculosis and malaria; and allergic diseases including, but not limited to, asthma, atopic dermatitis and COPD.

The antigen binding proteins of the present invention may also have use in the treatment of cancer, including, but not limited to ovarian cancer, melanoma (e.g. metastatic malignant melanoma), prostate cancer, bowel cancer (e.g. colon cancer and cancer of the small intestine), stomach cancer, oesophageal cancer, breast cancer, lung cancer, renal cancer (e.g. clear cell carcinoma), pancreatic cancer, uterine cancer, liver cancer, bladder cancer, cervical cancer, oral cancer, brain cancer, testicular cancer, skin cancer, thyroid cancer, and haematological malignancies including myelomas and chronic and acute leukaemias.

It will be appreciated by those skilled in the art that references herein to "treatment" or "therapy" may, depending on the condition, extend to prophylaxis in addition to the treatment of an established condition.

There is thus provided as a further aspect of the invention an antigen binding protein of the present invention for use in therapy.

There is also therefore provided an antigen binding protein of the present invention for use in the treatment of psoriasis, Crohn's disease, rheumatoid arthritis, primary biliary cirrhosis, SLE, Sjögren's syndrome, multiple sclerosis, ulcerative colitis or autoimmune hepatitis.

In a further embodiment, there is provided an antigen binding protein of the present invention for use in the treatment of psoriasis.

In a further embodiment, there is provided an antigen binding protein of the present invention for use in the treatment of Crohn's disease.

In a further embodiment, there is provided an antigen binding protein of the present invention for use in the treatment of ulcerative colitis.

There is further provided the use of an antigen binding protein of the present invention in the manufacture of a medicament for the treatment of psoriasis, Crohn's disease, rheumatoid arthritis, primary biliary cirrhosis, systemic lupus erythematosus (SLE), Sjögren's syndrome, multiple sclerosis, ulcerative colitis or autoimmune hepatitis.

In a further embodiment, there is provided the use of an antigen binding protein of the present invention in the manufacture of a medicament for the treatment of psoriasis.

In a further embodiment, there is provided the use of an antigen binding protein of the present invention in the manufacture of a medicament for the treatment of Crohn's disease.

In a further embodiment, there is provided the use of an antigen binding protein of the present invention in the manufacture of a medicament for the treatment of ulcerative colitis.

There is further provided a method of treatment of a human or animal subject, which method comprises administering a therapeutically effective amount of an antigen binding protein of the present invention.

There is further provided a method of treatment of a disease associated with the involvement of pathogenic T cells in a human or animal subject comprising administering a therapeutically effective amount of an antigen binding protein of the present invention.

There is further provided a method of treatment of psoriasis, Crohn's disease, rheumatoid arthritis, primary biliary cirrhosis, systemic lupus erythematosus (SLE), Sjögren's syndrome, multiple sclerosis, ulcerative colitis or autoimmune hepatitis, which method comprises administering to a human subject in need thereof, a therapeutically effective amount of an antigen binding protein of the present invention.

In a further embodiment, there is provided a method of treatment of psoriasis, which method comprises administering to a human subject in need thereof, a therapeutically effective amount of an antigen binding protein of the present invention.

In a further embodiment, there is provided a method of treatment of Crohn's disease, which method comprises administering to a human subject in need thereof, a therapeutically effective amount of an antigen binding protein of the present invention.

In a further embodiment, there is provided a method of treatment of ulcerative colitis, which method comprises administering to a human subject in need thereof, a therapeutically effective amount of an antigen binding protein of the present invention.

The phrase "therapeutically effective amount" as used herein is an amount of an antigen binding protein of the present invention required to ameliorate or reduce one or more symptoms of, or to prevent or cure, the disease.

EXAMPLES

The following Examples illustrate but do not limit the invention.

Example 1: Biacore™ SPR Analysis of Purified Anti-LAG-3 Humanised Antibodies A9H12 (IMP731), as disclosed in WO 2008/132601, was humanised by grafting murine CDRs onto two heavy and two light chain human acceptor frameworks. A number of heavy and light chain humanised anti-LAG-3 variants were prepared, containing human to murine back mutations and CDR modifications. Heavy chain variants were numbered H0 to H8, and J0, J7 to J13 and light chain variants were numbered L0 to L10 and M0 to M1. Tissue culture supernatants containing all combinations of heavy and light chain humanised anti_LAG-3 variants were analysed for binding to Fc-tagged recombinant soluble LAG-3 (IMP321). The data was analysed using a 1:1 model inherent to the Biacore™ 4000 software. Antibodies were selected based on calculated affinities and also by visual comparison of binding sensorgrams with the chimeric antibody IMP731. A total of 54 constructs that exhibited equivalent or improved binding for IMP321 were identified for re-analysis using a Biacore™ 3000. Data was fitted to both the 1:1 and bivalent models, inherent to the BiaCore 3000 analysis software, and binding data was compared by normalising the binding curves at maximal association and comparing off-rates against IMP731 visually. This enabled antibodies that demonstrated improved off-rates in comparison to IMP731 to be discerned. A total of 18 humanised anti-LAG-3 antibodies were selected for further analysis on the basis of either equivalent or improved binding kinetics to recombinant sLAG-3 in comparison to IMP731. These 18 humanised antibodies were re-expressed and analysed as follows:

Anti-LAG-3 humanised antibodies were expressed in HEK 293 6E cells and purified by affinity chromatography as follows:

100 ml Scale HEK 293 6E Expression

Expression plasmids encoding heavy and light chains of the humanised antibodies identified in Table 3 were transiently co-transfected into HEK 293 6E cells and expressed at 100 ml scale to produce antibody.

Purification of Humanised Antibodies

The expressed antibody molecules were purified by affinity chromatography. Protein A sepharose beads (GE Healthcare Cat No 17-5280-04), were added to the cell culture supernatants and mixed at room temperature for 30-60 minutes. The protein A sepharose beads were then centrifuged and washed in PBS. The mixture was then added into a 10 ml disposable column (Pierce Cat No: 29924) and the PBS allowed to drain. The column was washed 3 times with 10 ml PBS before elution of the antibody with IgG Elution buffer (Pierce Cat No: 21009). The antibody eluted was immediately neutralized using 1M Trizma® hydrochloride buffer (T2819) and was then buffer exchanged into PBS with a Vivaspin 6 mwco 5000 column (Cat. No.: FDP-875-105D). The yield was determined by measurement of absorbance at 280 nm. The level of aggregated protein in the purified sample was determined by size exclusion chromatography.

Binding Kinetics

The binding kinetics of the purified antibodies for a sLAG-3 molecule were assessed by SPR using a Biacore™ 3000. A goat anti-human kappa antibody (Southern Biotech, Catalogue No. 2060-01) was immobilised on a CM5 chip by primary amine coupling. Humanised anti-LAG3 antibodies were captured on this surface and the LAG3-Ig molecule IMP321 (Chrystelle Brignone, Caroline Grygar, Manon Marcu, Knut Schakel, Frederic Triebel, The Journal of Immunology, 2007, 179: 4202-4211) used as the analyte at 64 nM with a buffer injection (i.e. 0 nM) used to double reference the binding curves. Regeneration was with 10 mM Glycine, pH1.5. The run was carried out on the Biacore™ 3000, using HBS-EP as running buffer and at 25° C. Sensorgrams were normalised for binding at maximal association and off-rates compared against IMP731 by visual inspection of the sensorgram profiles.

The results show that the purified humanised anti-LAG-3 antibodies can be categorised into 3 groups; group 1 with humanised variants that appear to be better at binding to IMP321 than the chimeric IMP731, group 2 with variants that appear to bind in a very similar manner to IMP731 and group 3 with variants that demonstrate worse binding than IMP731.

10 humanised variants fall within group 1 and demonstrate improved (i.e. reduced) off-rates when compared to IMP731 by visual inspection of the Biacore™ sensorgrams. All of these molecules contained the L7 light chain, which contains a glycine to proline substitution at position 27e in light chain CDR1. This data indicates that proline at position 27e improves the off-rate for IMP321 of the humanised anti-LAG-3 antibodies when paired with numerous humanised heavy chains.

Of the remaining antibodies tested, 4 molecules fall within group 2 and had similar off-rates to the chimeric IMP731 antibody, while 4 other molecules fall within group 3 and exhibit worse off-rates than IMP731. Table 3 provides an approximate ranking of those molecules in comparison to IMP731. H5L7 exhibits the best off-rate (i.e. lowest) in this experiment by visual inspection of the Biacore™ sensorgrams.

TABLE 3

| Comparison of off-rates with IMP731 | | |
|---|---|---|
| Humanised Variant | Off-rate comparison with IMP731 | Rank order of off-rates |
| H5L7 | better | 1 |
| H1L7 | better | 2 |
| J7L7 | better | 3 |
| H4L7 | better | 4 |
| J11L7 | better | 5 |
| H2L7 | better | 6 |
| J13L7 | better | 7 |
| H7L7 | better | 8 |
| J0L7 | better | 9 |
| H0L7 | better | 10 |
| H1L1 | same | |
| H5L1 | same | |
| J7L1 | same | |
| J11L1 | same | |
| J13L1 | worse | |
| H7L1 | worse | |
| J0L1 | worse | |
| H0L1 | worse | |

Example 2: Binding Analysis of Wild Type Fucosylated and Afucosylated Humanised Anti-LAG-3 Antibodies for Binding to Recombinant Human LAG-3-His Using the Biacore™ T100

Afucosylated antibody H5L7BW was generated by expression of plasmids encoding H5L7 in the BioWa POTELLIGENT® (FUT8 knock-out CHO) cell line. Afucosylated antibodies produced using POTELLIGENT® technology have been shown to exhibit increased antibody dependent cell-mediated cytotoxicity (ADCC) compared to equivalent highly-fucosylated conventional antibodies through increased affinity to FcγRIIIa (CD16).

Wild type fucosylated and afucosylated antibodies were compared for their ability to bind to recombinant human LAG-3 ECD with a C-terminal His6 (SEQ ID NO:51) using the Biacore™ T100 (GE Healthcare™). Protein A was immobilised on a CM5 chip by primary amine coupling. This surface was then used to capture the humanised antibodies. Recombinant human LAG-3 ECD-His6 was then passed over the captured antibodies at 32, 8, 2, 0.5 and 0.125 nM and regeneration was carried out using 50 mM NaOH. The binding curves were double referenced with buffer injection (i.e. 0 nM) and the data was fitted to the T100 analysis software using the 1:1 model. The run was carried out at 25° C., using HBS-EP as the running buffer.

In order to investigate the statistical significance of this kinetic data, this experiment was repeated 3 times with the same batch of the four antibodies and the chimeric control. KD, ka and kd parameters were each log (base 10) transformed prior to separate statistical analyses. For each parameter, a mixed model analysis of variance ('Anova') was performed on transformed data, including terms for Run (random block effect) and Antibody.

From the Anova, geometric means were predicted for each antibody, along with statistically plausible ranges (95% confidence intervals) for each mean. Planned comparisons of antibodies were performed within the Anova. Comparisons are presented as ratios of the two antibodies compared, again with 95% confidence intervals and p values. The ratios may also be interpreted as a fold change, e.g. a ratio of 0.1 corresponds to a 90% decrease.

Geometric means were derived for each of the humanised antibodies and the chimeric control IMP731 for the binding affinity (KD), shown in Table 4. The mean KD for H5L7 was 0.2075 nM, a significant decrease of 92% (i.e. 10 fold decrease) with $p<0.0001$ when compared with IMP731. IMP731 exhibited a mean KD of 2.76 nM. Afucosylated H5L7BW exhibits equivalent binding as fucosylated H5L7, with a geometric KD of 0.2179 nM, with no significant difference ($p=0.1790$).

The improvement in affinity observed for H5L7 in comparison to IMP731 is predominantly driven by differences in the off-rates of the antibodies for LAG-3-ECD-His6, shown in Table 5. There is an approximate 85% decrease (i.e. almost 10 fold decrease) in kd for H5L7 in comparison IMP731 which is highly statistically significant. There is no significant difference between afucosylated H5L7BW and H5L7 ($p=0.4408$).

TABLE 4

Statistical evaluation for the KD of fucosylated and afucosylated anti-LAG-3 variants binding to recombinant human LAG-3-His

| Geometric Means for KD (nM) | | | | |
|---|---|---|---|---|
| Antibody | Batch No | Geometric mean | Lower 95% CI | Upper 95% CI |
| H5L7 | GRITS42382 | 2.08E−10 | 1.89E−10 | 2.28E−10 |
| H5L7BW | GRITS42760 | 2.18E−10 | 1.98E−10 | 2.40E−10 |
| IMP731 | 020909 | 2.76E−09 | 2.51E−09 | 3.04E−09 |
| **Comparisons of KD** | | | | |
| KD comparison | Ratio | Lower 95% CI | Upper 95% CI | P value |
| H5L7BW-H5L7 | 1.0502 | 0.97268 | 1.13389 | 0.179 |
| H5L7-IMP731 | 0.07736 | 0.0715 | 0.0837 | <.0001 |

TABLE 5

Statistical evaluation for the kd of fucosylated and afucosylated anti-LAG-3 variants binding to recombinant human LAG-3-His

| Geometric Means for kd (1/s) | | | | |
|---|---|---|---|---|
| Antibody | Batch No | Geometric mean | Lower 95% CI | Upper 95% CI |
| H5L7 | GRITS42382 | 3.95E−03 | 3.16E−03 | 4.94E−03 |
| H5L7BW | GRITS42760 | 4.41E−03 | 3.53E−03 | 5.51E−03 |
| IMP731 | 020909 | 2.75E−02 | 2.20E−02 | 3.44E−02 |
| **Comparisons of kd** | | | | |
| KD comparison | Ratio | Lower 95% CI | Upper 95% CI | P value |
| H5L7BW-H5L7 | 1.11715 | 0.81531 | 1.53073 | 0.4408 |
| H5L7-IMP731 | 0.15478 | 0.11157 | 0.21471 | <.0001 |

Example 3: Evaluation of the LAG-3-His Binding Epitope of Anti-LAG-3 Humanised Variants in Comparison with Chimeric Antibody IMP731 Using the ProteOn™

An epitope binning experiment was performed with H5L7 to evaluate whether the LAG-3 epitope within which IMP731 binds was conserved upon humanisation. Furthermore, the binding epitope of fucosylated and afucosylated humanised variants was also compared.

Epitope binding was evaluated using the ProteOn™ XPR36 (BioRad™) biosensor machine, by assessing whether anti-LAG-3 antibodies were able to simultaneously bind to LAG-3-His in complex with antibody captured on the ProteOn™ chip surface. IMP731 and non-competitive murine antibody 17B4 were utilised as controls in this assay.

The antibodies to be tested were biotinylated using Ez-Link-sulfo-NHS biotinylation kit. Each biotinylated antibody was captured on a separate flow cell on a neutravidin NLC chip using a vertical injection. After antibody capture, the surface was blocked with biocytin at 2.5 mg/ml. Using the co-inject facility inherent to the ProteOn run software, LAG-3 ECD-His6 was injected over the coupled antibodies at 100 nM, followed by the un-biotinylated antibodies at 100 nM with both injections being horizontal so that the LAG-3-His and the antibodies cross all 6 neutravidin captured antibodies. The assay was run at 25° C. and in HBS-EP on the ProteOn XPR36 Protein Interaction Array System.

Data analysis was carried out using report points taken after the LAG-3-His injection and report points taken after the un-biotinylated antibody analyte injection. The overall response was calculated by subtracting the response seen with the antibody binding from the response seen with LAG-3 ECD-His6 binding. A positive resonance unit (RU) value meant that antibody analyte injection had bound to LAG-3 ECD-His6 complexed with the biotinylated antibody on the neutravidin capture surface, indicative of binding at non-competitive epitopes. No response or a negative response meant that antibody analyte injection had not bound to LAG-3 ECD-His6 complexed with the biotinylated antibody on the neutravidin capture surface, indicating antibodies bind at competitive epitopes.

Anti-LAG-3 humanised variants (fucosylated and afucosylated) are unable to bind to human LAG-3 ECD-His6 in complex with IMP731, indicative that the epitope for LAG-3 ECD-His6 is shared and thus conserved. Murine antibody 17B4 is able to bind to human LAG-3 ECD-His6 in complex with IMP731 substantiating that this antibody is non-competitive for LAG-3 ECD-His6 binding with IMP731. Conversely, the humanised antibodies are able to bind to human LAG-3 ECD-His6 in complex with 17B4.

The results confirm that there has been no alteration in epitope between the chimeric IMP731 and the humanised variant of IMP731 tested in this experiment. The experiment also shows that there is no difference between fucosylated and afucosylated antibodies for binding.

Example 4: Binding Analysis of Anti-LAG-3 Humanised Antibodies to Recombinant Cynomolgus Macaque and Baboon LAG-3 ECD-His6 Using the Biacore™ T100

The binding cross reactivity of anti-LAG-3 humanised antibodies for both cynomolgus macaque (cyno) and baboon recombinant LAG-3 ECD-His6 (SEQ ID NOs 52 and 53, respectively) was assessed using the Biacore™ T100 (GE Healthcare).

Protein A was immobilised on a CM5 chip by primary amine coupling. This surface was then used to capture the humanised antibodies. In-house generated recombinant cynomolgus macaque and baboon LAG-3 ECD-His6 were then passed over the captured antibodies and regeneration was carried out using 50 mM NaOH. LAG-3 ECD-His6 was passed over at 16, 4, 1, 0.25 and 0.0625 nM. The binding curves were double referenced with buffer injection (i.e. 0 nM) and the data was fitted to the T100 analysis software using the 1:1 model. The run was carried out at 37° C. using HBS-EP as the running buffer.

H5L7, H5L7BW and IMP731 bind with comparable affinity to both cynomolgus macaque and baboon recombinant LAG-3 ECD-His6. Data was generated from separate experiments, however chimeric antibody IMP731 was utilised as a control between experiments.

This data indicates that both non-human primate recombinant LAG-3 orthologues bind to the H5L7 derived antibodies with a 10 fold improvement in affinity in comparison with human recombinant LAG-3 ECD-His6 (SEQ ID NO: 51) (H5L7: human LAG-3 0.208 nM, cyno LAG-3 0.017 nM and baboon LAG-3 0.022 nM; H5L7BW human LAG-3 0.218 nM, cyno LAG-3 0.021 nM and baboon LAG-3 0.024 nM). Whilst both non-human primate recombinant LAG-3 orthologues bind to IMP731 derived antibodies with an improvement in affinity of approximately 100 fold in comparison with human recombinant LAG-3 ECD-His6 (SEQ ID NO: 51) (IMP731: human LAG-3 2.76 nM, cyno LAG-3 0.021 nM and baboon LAG-3 0.019 nM).

Example 5: Binding Profiles of H5L7BW, H5L7 and IMP731 to Human LAG-3 Expressing EL4 Cells, and Human Primary Activated CD3+ T Cells Human LAG-3 expressing EL4 cells were incubated with either IMP731, H5L7 or H5L7BW Alexa647-conjugated antibodies at varying concentrations of up to 50 μg/ml for 30 minutes at room temperature. Cells were washed with FACS buffer (PBS+0.5% BSA) to remove unbound antibody.

$CD3^+$ T cells were prepared from PBMCs by negative selection using Untouched Human T cell Dynal beads. $CD3^+$ T cells were activated by incubation with immobilised anti-CD3 and anti-CD28 and soluble recombinant human IL-12 for 3 days at 37° C. Activated cells were incubated with Alexa 647-conjugated antibodies of varying concentrations up to 3 μg/ml for 30 minutes at room temperature. Cells were washed with FACS buffer (PBS+0.5% BSA).

EL4 cells and $CD3^+$ T cells were analysed by FACS using a Beckman Coulter FC 500 flow cytometer. FACS raw data were analysed using CXP Analysis software (Beckman Coulter). The data was initially plotted on a forward-scatter versus side-scatter plot and the population of cells of interest were gated. This gated population was then plotted as a histogram displaying fluorescence intensity and the mean fluorescence intensity (MFI) calculated. MFI values were then plotted in GraphPad Prism 5 software to generate dose response curves.

Binding profiles of H5L7BW, H5L7 and IMP731 to human LAG-3 expressing EL4 cells, and human primary activated CD3+ T cells are shown in FIG. 1. The three antibodies exhibited similar binding characteristics to human LAG-3 expressing EL4 cells (FIG. 1A) and activated human CD3+ T cells (FIG. 1B).

Example 6: Assessment of the Depleting Activity of H5L7BW and H5L7 by Antibody Dependent Cellular Cytotoxicity (ADCC) in Primary Human T Cells The donors used in these experiments were screened for re-call responses to the CD4 antigens present in Revaxis, (Diphtheria, Tetanus and Poliomyelitis) and to either a CMVpp65 peptide pool or to a CD8 peptide pool, which contained peptide epitopes to CMV, EBV and Influenza. The antigen used to perform initial studies was the CMVpp65 peptide pool. However, due to the limited number of donors that demonstrated a re-call response to this antigen, Revaxis and the CD8 peptide pool were the antigens used to generate the majority of the potency data for the anti-LAG3 antibodies.

Peripheral blood was collected from healthy human volunteers on day 0 (25 mL) and day 5 (75 mL) of the experiment and was used to prepare mononuclear cells by ficollplaque density gradient centrifugation. The PBMCs prepared on day 0 were labeled using the CellTrace™ Violet Cell Proliferation Kit, in accordance with the manufacturer's instructions, after which they were washed, seeded in 24-well flat bottomed tissue culture plates at a density of 2×106/mL in medium and stimulated with antigen (Revaxis and the CD8 peptide pool were used at a dilution of 1 in 1000; the CMVpp65 peptide was used at a dilution of 1 in 100). The PBMCs were incubated for 5 days at 37° C. in a 5% CO2 humidified incubator.

Autologous donor NK cells were purified from the PBMCs prepared on day 5 of the experiment by negative selection using kits from either Invitrogen or Miltenyi Biotec in accordance with the specific instructions of each manufacturer. The purified NK cells were counted and diluted to a density of 1.3×106/mL in medium.

The cells that had been stimulated with antigen for 5 days were washed, counted and diluted to a density of 2×106/ viable cells/mL in medium.

Autologous donor NK cells (80 μL) and antigen activated cells (100 μL) were pipetted into round-bottomed 5 mL polystyrene FACS tubes with test antibody or medium (20 μL). The final concentrations of the anti LAG-3 antibodies tested ranged from 1000 to 0.015 ng/mL. The samples were incubated for 18 h at 37° C. in a 5% CO2 humidified incubator. After 18 h the ADCC assay samples were analysed for the presence of antigen specific LAG-3 positive T cells using flow cytometry. Briefly, the samples were washed in FACS buffer, blocked with human IgG (3 μg/tube), and incubated with mouse anti-human CD4, CD8, CD337, CD25 and LAG-3 flurochrome conjugated antibodies for 30 minutes in the dark at room temperature. After a further wash step in PBS the cells were incubated in the presence of a fixable green dead cell for 30 minutes in the dark at room temperature. The samples were finally washed with PBS, fixed and analysed by flow cytometry using a 60 second acquisition time at a flow rate of 1 μL per second.

All sample data were acquired using the BD FACSCanto II Flow Cytometer with FACS Diva software version 6.1.3 (BD BioSciences). The Live/Dead fixable green dead cell stain was used as a dead cell exclusion marker and appropriate isotype and FMO-1 controls were used to define negative populations. Briefly dead cells were omitted from the analysis using a plot of forward scatter (FSC-A) against fluorescence in FL1 (Green dead cell stain). Doublets were then excluded from the analysis by using a plot of FSC-W against FSC-H. Viable single lymphocytes were subsequently identified and gated using a plot of forward scatter (FSC-A) against side scatter (SSC-A). CD4 antigen specific T cells were identified from this gated population of cells using plots of CD4 fluorescence against SSC-A and Violet Dye fluorescence against CD4 fluorescence respectively. Antigen specific CD4 T cells were identified by a reduction of Violet Dye fluorescence. A further plot of CD25 fluorescence against LAG-3 fluorescence was drawn to confirm the activation state of this population of cells and that they expressed LAG-3. Similar plots were drawn to identify antigen specific CD8 T cells.

The percentages of antigen specific CD4 and CD8 T cells present in each sample (as a percentage of the viable lymphocyte population) were recorded. Nonlinear variable slope curve-fits of these data were plotted and EC50 values were generated using GraphPad Prism software (v5.03).

To calculate the maximum level of depletion observed in an assay, at the highest concentration of antibody tested, the following formula was used: (1−(% Antigen specific T cells remaining after antibody treatment)/(% Antigen specific T cells remaining in the absence of antibody))*100.

Potency data for the depletion of LAG3 positive antigen specific CD8 and CD4 T cells by H5L7BW and H5L7 was generated using the in vitro assay system detailed above. H5L7BW induced depletion of LAG3 positive antigen specific CD4 and CD8 T cells by ADCC in six of the seven donors studied for disappearance of the respective cell types. The potency of H5L7BW in antigen specific CD4 T cells, as quantified by EC50 values, ranged from 14 μg/mL to 3.4 ng/mL with maximum levels of depletion ranging from 44 to 78%. The potency of this antibody in antigen specific LAG-3 positive CD8 T cells ranged from 122 μg/mL to 17.5 ng/mL, with maximum levels of depletion ranging from 39 to 87%. H5L7 mediated low levels of depletion, or was inactive, in the donors studied.

Example 7: Assessment of the Depleting Activity of H5L7BW and H5L7 in an In-Vivo Human PBMC/Mouse SCID Xenograft Model This assay describes the use of a human PBMC/mouse SCID xenograft model to assess in vivo depletion efficacy of the monoclonal, fully humanised, afucosylated LAG-3 depleting antibody H5L7BW on activated human T cells. Healthy volunteer peripheral blood mononuclear cells (PBMCs) were isolated and stimulated overnight (anti-CD3, IL-12) to induce LAG-3 expression prior to injection into the peritoneum of immuno-compromised SCID mice. LAG-3 depleting or control antibodies were either co-administered into the peritoneum or injected intravenously.

Depletion of LAG-3 positive cells was assessed by flow cytometry in peritoneal lavage samples 5 or 24 hours after cell injection.

Mice were injected with activated huPBMCs (4×106-2×107 cells in 0.4 ml of PBS) by the intraperitoneal route. Depending on the particular study route, LAG-3 antibodies or huIgG1 BioWa controls were either co-administered i.p. with the huPBMCs or mice were pre-treated intravenously 18 h prior to huPBMC injection. 5 or 24 hours post-cell injection, mice were euthanized, a peritoneal lavage was performed and the cellular content of the lavage buffer analysed by flow cytometry. Briefly, peritoneal lavage involved 3×5 ml washes of the intact peritoneal cavity using cold PBS containing 3 mM EDTA.

All sample data were acquired using the BD FACSCanto II Flow Cytometer with FACS Diva software version 6.1.3 (BD BioSciences). Approximately 1×106 cells (where possible) were added per FACS tube, the cell suspensions centrifuged at 1500 rpm for 10 minutes, and the pellet then re-suspended in 3 ml PBS. The supernatants were then carefully decanted and the cell pellets re-suspended in 100 μl cold FACS wash buffer. 15 μl FcR Blocking Reagent was then added per tube and the cells incubated for 10 minutes at room temperature. 5 μl of each staining antibody (10 μl of 1:100 pre-diluted anti-LAG-3 blocking/detection antibody 17B4-PE) or isotype control were then added respectively and incubated for 20 minutes at room temperature protected from light. The cells were subsequently washed by addition of 4 ml FACS buffer per tube and centrifugation at 1500 rpm for 5 minutes after which the supernatant was carefully decanted. This washing step was repeated. Finally the cells were re-suspended in 300 μl FACS buffer and analysed by flow cytometry. In addition to LAG-3 detection by use of the fluorescently labeled LAG-3 blocking antibody 17B4-PE, the following T cell and activation markers were used for T cell phenotyping: CD45, CD4, CD8, and CD25. Percentages of CD4 and CD8 T cells were expressed as percentage of CD45 positive cells. LAG-3 positive T cell populations were expressed as percentages of their parent populations CD4 and CD8.

FACS Diva software version 6.1.3 was used to generate batch analyses of individual cell counts/events and cell population percentages. Data were analysed with SAS version 9.2.2 software using a generalized linear model for binomial data. This analysis directly models the cell count as a proportion of the parent population. In this way, the size of the parent population is taken into account during the analysis. Means were calculated for proportions of target cell type for each treatment, along with 95% confidence intervals. These were expressed as percentages.

Planned comparisons of treatments versus Control were made using odds ratios. This expresses the odds of having a target cell type in one treatment as a ratio to the odds of having the target cell type on control treatment. An odds ratio <1 would indicate a reduced odds of having the cell type in the treatment of interest compared to the control. An odds ratio <1 would indicate a reduced odds of having the cell type in the treatment of interest compared to the control.

All experiments were performed using PBMCs from individual healthy blood donors and due to the large blood volumes required per experiment, no donor was used more than once. LAG-3 expression levels after overnight stimulation varied greatly between donors (ranging from 2-73% cell surface expression) but these differences in expression levels had no effect on the highly significant depletion efficacy of the tested antibodies.

Figure 2:
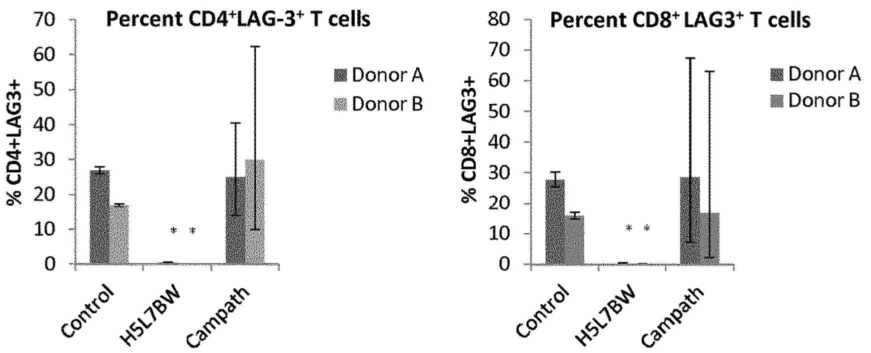
FIG. 2: Effect of afucosylated antibody H5L7BW administered intra-peritoneally on co-administered, activated human PBMCs retrieved from the peritoneal cavity 24 hours post-injection. A) Quantification of human $CD4^+LAG\text{-}3^+$ and $CD8^+LAG\text{-}3^+$ T cells 24 hours after co-administration of $1\times10^7$ activated human PBMCs and 5 mg/kg Control antibody, H5L7BW or Campath™ (Donor A: Control n=2; H5L7BW n=2, MabCampath n=1; Donor B: Control n=2; H5L7BW n=3, Campath™ n=2). B) Quantification of total $CD4^+$ and $CD8^+$ T cells. (*p<0.001).
Figure 2:
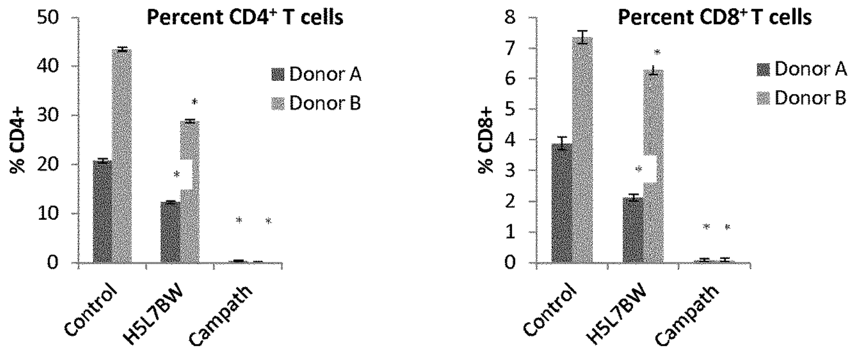

The human PBMC/mouse SCID in vivo model was successfully used to show depletion of activated human, LAG-3 expressing T cells in the peritoneum of immunocompromised SCID mice. Depending on donor, route of administration and time point of analysis, between 84.22-99.71% of LAG-3 positive human CD4 T cells and between 84.64-99.62% of LAG-3 positive human CD8 T cells were depleted. As shown in FIG. 2, co-administration of 5 mg/kg H5L7BW to activated human PBMCs in the peritoneum of SCID mice led to highly significant depletion of LAG-3 positive CD4 and CD8 positive T cells 24 hours after injection compared to Control IgG injected animals.

Figure 3:
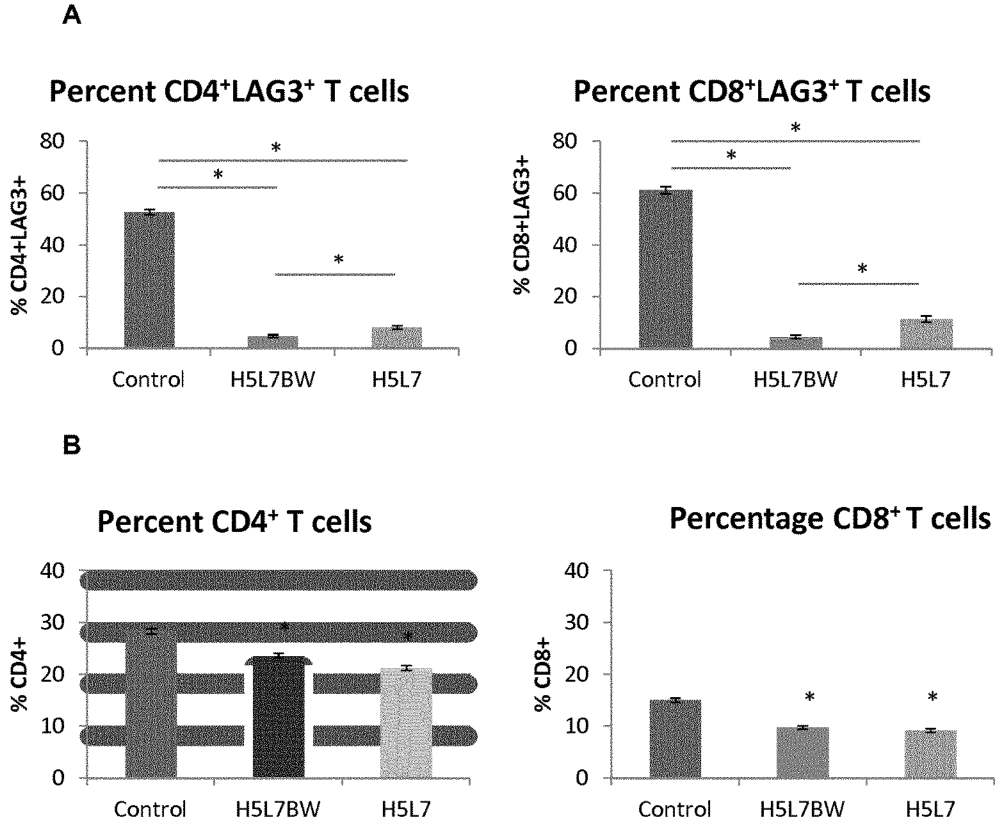
FIG. 3: Effect of afucosylated antibody H5L7BW and its non-ADCC enhanced variant H5L7 on activated human PBMCs co-administered intra-peritoneally and retrieved from the peritoneal cavity 5 hours post-injection. A) Quantification of human $CD4^+LAG\text{-}3^+$ and $CD8^+LAG\text{-}3^+$ T cells 5 hours after co-administration of $1\times10^7$ activated human PBMCs and 5 mg/kg Control antibody, H5L7BW or H5L7 (n=3 per group). B) Quantification of total $CD4^+$ and $CD8^+$ T cells. (*p<0.001).

FIG. 3 highlights the comparison between 5 mg/kg H5L7BW and H5L7 5 hours after co-i.p. administration to activated human PBMCs as described before. Both antibodies induced highly significant depletion of LAG-3 positive CD4 and CD8 T cells (FIG. 3A).

Figure 4:
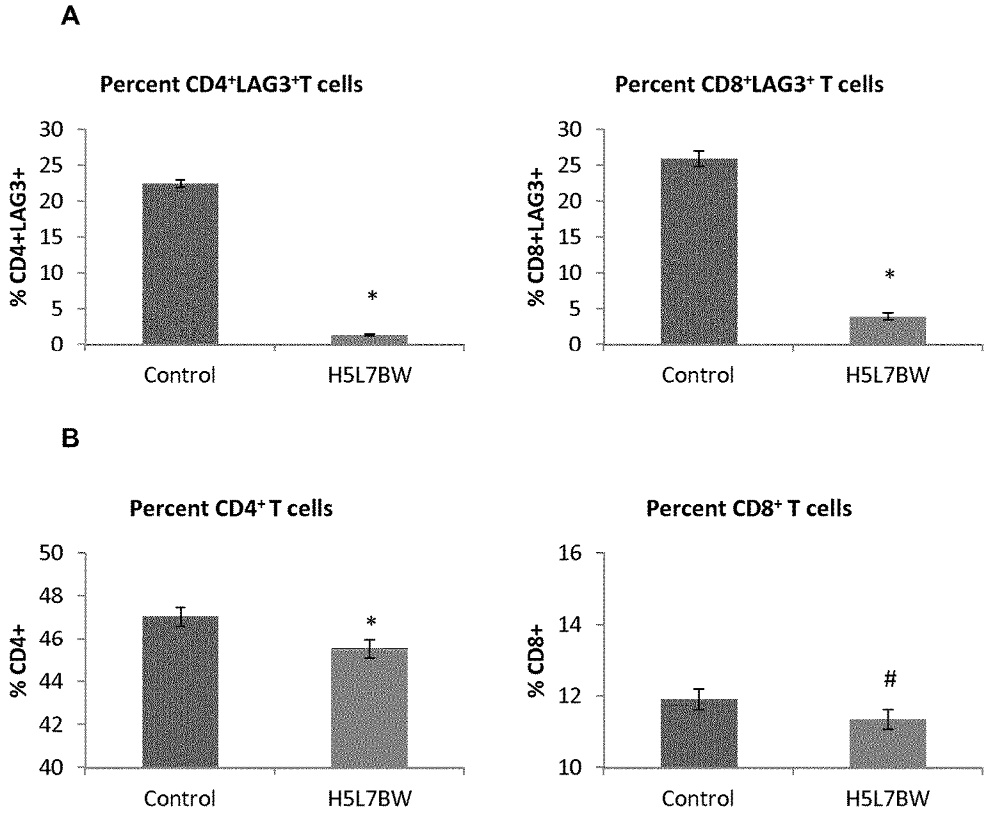
FIG. 4: Effect of afucosylated antibody H5L7BW administered intravenously 18 hours pre-administration of human activated PBMCs into the peritoneum of SCID mice. A) Quantification of human $CD4^+LAG\text{-}3^+$ and $CD8^+LAG\text{-}3^+$ T cells 5 hours after i.p. injection of $5\times10^6$ (n=1 per group) or $1\times10^7$ O/N (n=4 per group) activated human PBMCs. B) Quantification of total $CD4^+$ and $CD8^+$ T cells. 5 mg/kg H5L7BW or control antibody was injected intravenously 18 hours pre-injection of activated human PBMCs. (*p<0.001, # p=0.0052).
Figure 5:
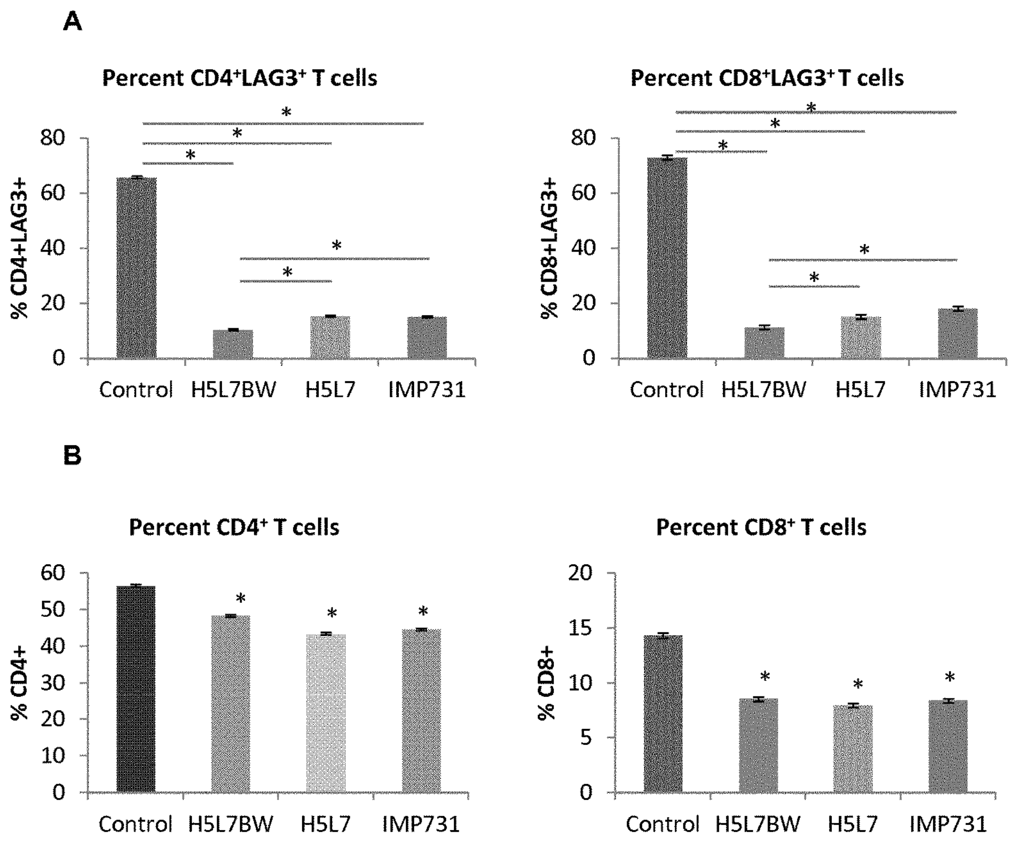
FIG. 5: Effect of H5L7BW, H5L7 or IMP731 (5 mg/kg) administered intravenously 18 hours pre-administration of activated human PBMCs into the peritoneum of SCID mice. A) Quantification of human $CD4^+LAG\text{-}3^+$ and $CD8^+LAG\text{-}3^+$ T cells 5 hours after i.p. injection of $1\times10^7$ (n=4 per group) activated human PBMCs. 5 mg/kg H5L7BW, H5L7, IMP731 or control antibody were injected intravenously 18 hours pre injection of human PBMCs. B) Quantification of total $CD4^+$ and $CD8^+$ T cells. 5 mg/kg LAG-3 depleting antibodies or control antibody were injected intravenously 18 hours pre-injection of activated human PBMCs. (*p<0.001).

As shown in FIG. 4, administration of 5 mg/kg H5L7BW via the intra-venous route resulted in a highly statistically significant depletion of LAG-3 positive T cells after 5 hours (FIG. 4A), similar to what was observed in the experiments with i.p. co-administered LAG-3 depletion antibodies. The comparison between i.v. administered H5L7BW, H5L7 and IMP731 (all at 5 mg/kg) 5 hours after i.p. administration of activated human PBMCs revealed very similar depletion efficacies between the 3 molecules compared to control treated animals (FIG. 5). Each of the 3 tested LAG-3 depleting antibodies caused highly significant reduction in the number of LAG-3 positive CD4 and CD8 T cells (FIG. 5A) with H5L7BW demonstrating greater depletion capacity compared to H5L7 or IMP731.

Example 8: Binding Analysis of Anti-LAG-3 Humanised Antibodies to Recombinant Soluble Human Fc Gamma Receptors Using the ProteOn™

Human FcγRIIIa binding was investigated in order to assess the ability of H5L7 and H5L7BW to induce antibody dependent cell-mediated cytotoxicity (ADCC). H5L7 and H5L7BW anti-LAG-3 antibodies were assessed for binding to recombinant soluble human FcγRIIIa in addition to FcγRI and FcγRII receptors using the ProteOn™ XPR36 (Bio-Rad™) biosensor machine, and were compared against chimeric antibody IMP731.

A goat anti-poly-histidine IgG was immobilised on a GLM biosensor chip by primary amine coupling. This surface was used as a capture surface for the poly-histidine tagged human Fc gamma receptors. Antibodies to be tested were used as the analyte and passed over at 2048 nM, 512 nM, 128 nM, 32 nM and 8 nM with an injection of 0 nM (i.e. buffer alone) used to double reference the binding curves. The goat anti-poly-histidine IgG surface was regenerated with 100 mM phosphoric acid between interactions. The run was carried out on the ProteOn XPR36 Protein Array Interaction System at 25° C. and using HBS-EP as running buffer. Data was analysed for each receptor separately, setting a global R-max and using the Equilibrium Model inherent to the ProteOn's analysis software. Control molecules were run at the beginning and the end of the set of samples to be tested to ensure comparability of results. Data was compared from two experiments and hybrid control antibodies used as controls between experiments.

The results show that H5L7BW bound both polymorphisms of FcγRIIIa (valine V158 and phenylalanine F158) with an improved affinity of approximately 10 fold in comparison to H5L7 (see Table 6). Fucosylated antibody H5L7 bound to FcγRIIIa with a similar affinity as chimeric antibody IMP731.

No significant changes were observed between the binding of the humanised fucosylated and afucosylated anti-LAG-3 antibodies for the FcγRI or FcγRIIa receptors.

TABLE 6

Binding of H5L7 and H5L7BW to human Fc gamma receptors

| Antibody | FcγRI (nM) | FcγRIIa R131 (nM) | FcγRIIa H131 (nM) | FcγRIIIa V158 (nM) | FcγRIIIa F158 (nM) |
|---|---|---|---|---|---|
| IMP731 | 39.0 | 2620.0 | 1280.0 | 406.0 | 1750.0 |
| H5L7 | 26.3 | 792.0 | 638.0 | 236.0 | 752.0 |
| H5L7BW | 26.4 | 1490.0 | 1430.0 | 21.8 | 81.1 |

Sequences

TABLE 7

Sequence Summary

| Sequence | Sequence Identifier (SEQ ID No.) Amino acid Sequence | Polynucleotide Sequence |
|---|---|---|
| H5L7, CDRL1 (Kabat defined) | 1 | 57 |
| H5L7, CDRL2 (Kabat defined) | 2 | 58 |
| H5L7, CDRL3 (Kabat defined) | 3 | 59 |

TABLE 7-continued

Sequence Summary

| Sequence | Sequence Identifier (SEQ ID No.) Amino acid Sequence | Polynucleotide Sequence |
|---|---|---|
| H5L7, VL | 4 | 60 |
| H5L7, light chain humanised construct | 5 | 61 |
| H5L7, CDRH1 (Kabat defined) | 6 | 62 |
| H5L7, CDRH2 (Kabat defined) | 7 | 63 |
| H5L7, CDRH3 (Kabat defined) | 8 | 64 |
| H5L7, VH | 9 | 65 |
| H5L7, heavy chain humanised construct | 10 | 66 |
| H1L7, light chain humanised construct | 11 | 67 |
| H1L7, heavy chain humanised construct | 12 | 68 |
| J7L7, light chain humanised construct | 13 | 69 |
| J7L7, heavy chain humanised construct | 14 | 70 |
| H4L7, light chain humanised construct | 15 | 71 |
| H4L7, heavy chain humanised construct | 16 | 72 |
| J11L7, light chain humanised construct | 17 | 73 |
| J11L7, heavy chain humanised construct | 18 | 74 |
| H2L7, light chain humanised construct | 19 | 75 |
| H2L7, heavy chain humanised construct | 20 | 76 |
| J13L7, light chain humanised construct | 21 | 77 |
| J13L7, heavy chain humanised construct | 22 | 78 |
| H7L7, light chain humanised construct | 23 | 79 |
| H7L7, heavy chain humanised construct | 24 | 80 |
| J0L7, light chain humanised construct | 25 | 81 |
| J0L7, heavy chain humanised construct | 26 | 82 |
| H0L7, light chain humanised construct | 27 | 83 |
| H0L7, heavy chain humanised construct | 28 | 84 |
| H1L1, light chain humanised construct | 29 | 85 |
| H1L1, heavy chain humanised construct | 30 | 86 |
| H5L1, light chain humanised construct | 31 | 87 |
| H5L1, heavy chain humanised construct | 32 | 88 |
| J7L1, light chain humanised construct | 33 | 89 |
| J7L1, heavy chain humanised construct | 34 | 90 |
| J11L1, light chain humanised construct | 35 | 91 |
| J11L1, heavy chain humanised construct | 36 | 92 |
| J13L1, light chain humanised construct | 37 | 93 |
| J13L1, heavy chain humanised construct | 38 | 94 |
| H7L1, light chain humanised construct | 39 | 95 |
| H7L1, heavy chain humanised construct | 40 | 96 |
| J0L1, light chain humanised construct | 41 | 97 |
| J0L1, heavy chain humanised construct | 42 | 98 |
| H0L1, light chain humanised construct | 43 | 99 |
| H0L1, heavy chain humanised construct | 44 | 100 |
| Human kappa chain constant region | 45 | 101 |
| Human IgG1 constant region | 46 | 102 |
| IMP731, VH | 47 | 103 |
| IMP731, VL | 48 | 104 |
| IMP731, heavy chain sequence | 49 | 105 |
| IMP731, light chain sequence | 50 | 106 |
| Recombinant human LAG-3-ECD-His6 | 51 | 107 |
| Recombinant cynomolgus macaque LAG-3 ECD-His6 | 52 | 108 |
| Recombinant baboon LAG-3 ECD-His6 | 53 | 109 |
| Leader sequence used for humanised variant heavy and light chain constructs | 54 | 110 |
| IMP731 Leader sequence | 55 | 111 |
| Leader sequence used for soluble LAG-3 constructs | 56 | 112 |

SEQ ID NO. 1

KSSQSLLNPSNQKNYLA

SEQ ID NO. 2

FASTRDS

SEQ ID NO. 3

LQHFGTPPT

SEQ ID NO. 4

DIQMTQSPSSLSASVGDRVTITCKSSQSLLNPSNQKNYLAWYQQKPGKAPKLLVYFASTRDSGVPSRFSGSGSG

TDFTLTISSLQPEDFATYYCLQHFGTPPTFGQGTKLEIKR

-continued

SEQ ID NO. 5
DIQMTQSPSSLSASVGDRVTITCKSSQSLLNPSNQKNYLAWYQQKPGKAPKLLVYFASTRDSGVPSRFSGSGSG
TDFTLTISSLQPEDFATYYCLQHFGTPPTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGEC

SEQ ID NO. 6
AYGVN

SEQ ID NO. 7
MIWDDGSTDYDSALKS

SEQ ID NO. 8
EGDVAFDY

SEQ ID NO. 9
QVQLQESGPGLVKPSETLSLTCTVSGFSLTAYGVNWIRQPPGKGLEWIGMIWDDGSTDYDSALKSRVTISVDTS
KNQFSLKLSSVTAADTAVYYCAREGDVAFDYWGQGTLVTVSS

SEQ ID NO. 10
QVQLQESGPGLVKPSETLSLTCTVSGFSLTAYGVNWIRQPPGKGLEWIGMIWDDGSTDYDSALKSRVTISVDTS
KNQFSLKLSSVTAADTAVYYCAREGDVAFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALHNHYTQKSLSLSP
GK

SEQ ID NO. 11
DIQMTQSPSSLSASVGDRVTITCKSSQSLLNPSNQKNYLAWYQQKPGKAPKLLVYFASTRDSGVPSRFSGSGSG
TDFTLTISSLQPEDFATYYCLQHFGTPPTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGEC

SEQ ID NO. 12
QVQLQESGPGLVKPSETLSLTCTVSGFSLTAYGVNWIRQPPGKGLEWIGMIWDDGSTDYNSALKSRVTISVDTS
KNQFSLKLSSVTAADTAVYYCAREGDVAFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALHNHYTQKSLSLSP
GK

SEQ ID NO. 13
DIQMTQSPSSLSASVGDRVTITCKSSQSLLNPSNQKNYLAWYQQKPGKAPKLLVYFASTRDSGVPSRFSGSGSG
TDFTLTISSLQPEDFATYYCLQHFGTPPTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGEC

SEQ ID NO. 14
QVQLVQSGAEVKKPGSSVKVSCKASGFSLTAYGVNWVRQAPGQGLEWMGMIWDDGSTDYNSALKSRVTITADKS
TSTAYMELSSLRSEDTAVYYCAREGDVAFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALHNHYTQKSLSLSP
GK

-continued

SEQ ID NO. 15
DIQMTQSPSSLSASVGDRVTITCKSSQSLLNPSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 16
QVQLQESGPGLVKPSETLSLTCTVSGFSLTAYGVNWIRQPPGKGLEWLGMIWDDGSTDYNSALKSRLTISKDNS

KNQVSLKLSSVTAADTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 17
DIQMTQSPSSLSASVGDRVTITCKSSQSLLNPSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 18
QVQLVQSGAEVKKPGSSVKVSCKASGFSLTAYGVNWVRQAPGQGLEWMGMIWDDGSTDYDSALKSRVTITADKS

TSTAYMELSSLRSEDTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 19
DIQMTQSPSSLSASVGDRVTITCKSSQSLLNPSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 20
QVQLQESGPGLVKPSETLSLTCTVSGFSLTAYGVNWIRQPPGKGLEWIGMIWDDGSTDYNSALKSRVTISKDNS

KNQVSLKLSSVTAADTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 21
DIQMTQSPSSLSASVGDRVTITCKSSQSLLNPSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 22
QVQLVQSGAEVKKPGSSVKVSCKASGGTFSAYGVNWVRQAPGQGLEWMGMIWDDGSTDYDSALKSRVTITADKS

TSTAYMELSSLRSEDTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

-continued

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 23
DIQMTQSPSSLSASVGDRVTITCKSSQSLLNPSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 24
QVQLQESGPGLVKPSETLSLTCTVSGGSISAYGVNWIRQPPGKGLEWIGMIWDDGSTDYDSALKSRVTISVDTS

KNQFSLKLSSVTAADTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 25
DIQMTQSPSSLSASVGDRVTITCKSSQSLLNPSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 26
QVQLVQSGAEVKKPGSSVKVSCKASGGTFSAYGVNWVRQAPGQGLEWMGMIWDDGSTDYNSALKSRVTITADKS

TSTAYMELSSLRSEDTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTIPPVLDSDGSFFLYSKLIVDKSRWQQGNVFSCSVMHEALHNHYTQKSLSLSP

GK

SEQ ID NO. 27
DIQMIQSPSSLSASVGDRVTITCKSSQSLLNPSNQKNYLAWYQQKPGKAPKLLVYFASTRDSGVPSRFSGSGSG

TDFILTISSLQPEDFATYYCLQHFGIPPTFGQGTKLEIKRIVAAPSVFIFPPSDEQLKSGTASVVCLLNNTYPR

EAKVQWKVDNALQSGNSQESVIEQDSKDSTYSLSSILTLSKADYEKHKVYACEVTHQGLSSPVIKSFNRGEC

SEQ ID NO. 28
QVQLQESGPGLVKPSETLSLICTVSGGSISAYGVNWIRQPPGKGLEWIGMIWDDGSTDYNSALKSRVTISVDTS

KNQFSLKLSSVTAADTAVYYCAREGDVAFDYWGQGTLVIVSSASTKGPSVFPLAPSSKSTSGGTAALGCLVKDY

FPEPVIVSWNSGALTSGVHTFPAVLQSSGLYSLSSVVIVPSSSLGTQTYICNVNHKPSNIKVDKKVEPKSCDKT

HTCPPCPAPELLGGPSVFLFPPKPKDILMISRIPEVICVVVDVSHEDPEVKFNWYVDGVEVHNAKTKPREEQYN

STYRVVSVLIVLHQDWLNGKEYKCKVSNKALPAPIEKTISKAKGQPREPQVYTLPPSRDELTKNQVSLICLVKG

FYPSDIAVEWESNGQPENNYKTIPPVLDSDGSFFLYSKLIVDKSRWQQGNVFSCSVMHEALHNHYTQKSLSLSP

GK

SEQ ID NO. 29
DIQMIQSPSSLSASVGDRVTITCKSSQSLLNGSNQKNYLAWYQQKPGKAPKLLVYFASTRDSGVPSRFSGSGSG

TDFILTISSLQPEDFATYYCLQHFGIPPTFGQGTKLEIKRIVAAPSVFIFPPSDEQLKSGTASVVCLLNNTYPR

EAKVQWKVDNALQSGNSQESVIEQDSKDSTYSLSSILTLSKADYEKHKVYACEVTHQGLSSPVIKSFNRGEC

-continued

SEQ ID NO. 30

QVQLQESGPGLVKPSETLSLICTVSGFSLTAYGVNWIRQPPGKGLEWIGMIWDDGSTDYNSALKSRVTISVDTS

KNQFSLKLSSVTAADTAVYYCAREGDVAFDYWGQGTLVIVSSASTKGPSVFPLAPSSKSTSGGTAALGCLVKDY

FPEPVIVSWNSGALTSGVHTFPAVLQSSGLYSLSSVVIVPSSSLGTQTYICNVNHKPSNIKVDKKVEPKSCDKT

HTCPPCPAPELLGGPSVFLFPPKPKDILMISRIPEVICVVVDVSHEDPEVKFNWYVDGVEVHNAKTKPREEQYN

STYRVVSVLIVLHQDWLNGKEYKCKVSNKALPAPIEKTISKAKGQPREPQVYTLPPSRDELTKNQVSLICLVKG

FYPSDIAVEWESNGQPENNYKTIPPVLDSDGSFFLYSKLIVDKSRWQQGNVFSCSVMHEALHNHYTQKSLSLSP

GK

SEQ ID NO. 31

DIQMIQSPSSLSASVGDRVTITCKSSQSLLNGSNQKNYLAWYQQKPGKAPKLLVYFASTRDSGVPSRFSGSGSG

TDFILTISSLQPEDFATYYCLQHFGIPPTFGQGTKLEIKRIVAAPSVFIFPPSDEQLKSGTASVVCLLNNTYPR

EAKVQWKVDNALQSGNSQESVIEQDSKDSTYSLSSILTLSKADYEKHKVYACEVTHQGLSSPVIKSFNRGEC

SEQ ID NO. 32

QVQLQESGPGLVKPSETLSLTCTVSGFSLTAYGVNWIRQPPGKGLEWIGMIWDDGSTDYDSALKSRVTISVDTS

KNQFSLKLSSVTAADTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 33

DIQMTQSPSSLSASVGDRVTITCKSSQSLLNGSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 34

QVQLVQSGAEVKKPGSSVKVSCKASGFSLTAYGVNWVRQAPGQGLEWMGMIWDDGSTDYNSALKSRVTITADKS

TSTAYMELSSLRSEDTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 35

DIQMTQSPSSLSASVGDRVTITCKSSQSLLNGSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 36

QVQLVQSGAEVKKPGSSVKVSCKASGFSLTAYGVNWVRQAPGQGLEWMGMIWDDGSTDYDSALKSRVTITADKS

TSTAYMELSSLRSEDTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

-continued

SEQ ID NO. 37

DIQMTQSPSSLSASVGDRVTITCKSSQSLLNGSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 38

QVQLVQSGAEVKKPGSSVKVSCKASGGTFSAYGVNWVRQAPGQGLEWMGMIWDDGSTDYDSALKSRVTITADKS

TSTAYMELSSLRSEDTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 39

DIQMTQSPSSLSASVGDRVTITCKSSQSLLNGSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 40

QVQLQESGPGLVKPSETLSLTCTVSGGSISAYGVNWIRQPPGKGLEWIGMIWDDGSTDYDSALKSRVTISVDTS

KNQFSLKLSSVTAADTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 41

DIQMTQSPSSLSASVGDRVTITCKSSQSLLNGSNQKNYLAWYQQKPGKAPKLLVYFASTRDSGVPSRFSGSGSG

TDFTLTISSLQPEDFATYYCLQHFGTPPTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 42

QVQLVQSGAEVKKPGSSVKVSCKASGGTFSAYGVNWVRQAPGQGLEWMGMIWDDGSTDYNSALKSRVTITADKS

TSTAYMELSSLRSEDTAVYYCAREGDVAFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTIPPVLDSDGSFFLYSKLIVDKSRWQQGNVFSCSVMHEALHNHYTQKSLSLSP

GK

SEQ ID NO. 43

DIQMIQSPSSLSASVGDRVTITCKSSQSLLNGSNQKNYLAWYQQKPGKAPKLLVYFASTRDSGVPSRFSGSGSG

TDFILTISSLQPEDFATYYCLQHFGIPPTFGQGTKLEIKRIVAAPSVFIFPPSDEQLKSGTASVVCLLNNFYPR

EAKVQWKVDNALQSGNSQESVIEQDSKDSTYSLSSILTLSKADYEKHKVYACEVTHQGLSSPVIKSFNRGEC

SEQ ID NO. 44

QVQLQESGPGLVKPSETLSLICTVSGGSISAYGVNWIRQPPGKGLEWIGMIWDDGSTDYNSALKSRVTISVDTS

KNQFSLKLSSVTAADTAVYYCAREGDVAFDYWGQGTLVIVSSASTKGPSVFPLAPSSKSTSGGTAALGCLVKDY

FPEPVIVSWNSGALTSGVHTFPAVLQSSGLYSLSSVVIVPSSSLGTQTYICNVNHKPSNIKVDKKVEPKSCDKT

-continued

HTCPPCPAPELLGGPSVFLFPPKPKDILMISRIPEVICVVVDVSHEDPEVKFNWYVDGVEVHNAKTKPREEQYN

STYRVVSVLIVLHQDWLNGKEYKCKVSNKALPAPIEKTISKAKGQPREPQVYTLPPSRDELTKNQVSLICLVKG

FYPSDIAVEWESNGQPENNYKTIPPVLDSDGSFFLYSKLIVDKSRWQQGNVFSCSVMHEALHNHYTQKSLSLSP

GK

SEQ ID NO. 45

TVAAPSVFIFPPSDEQLKSGTASVVCLLNNFYPREAKVQWKVDNALQSGNSQESVIEQDSKDSTYSLSSILTLS

KADYEKHKVYACEVTHQGLSSPVIKSFNRGEC

SEQ ID NO. 46

ASTKGPSVFPLAPSSKSTSGGTAALGCLVKDYFPEPVIVSWNSGALTSGVHTFPAVLQSSGLYSLSSVVIVPSS

SLGTQTYICNVNHKPSNIKVDKKVEPKSCDKIHTCPPCPAPELLGGPSVFLFPPKPKDILMISRIPEVICVVVD

VSHEDPEVKFNWYVDGVEVHNAKTKPREEQYNSTYRVVSVLIVLHQDWLNGKEYKCKVSNKALPAPIEKTISKA

KGQPREPQVYTLPPSRDELTKNQVSLICLVKGFYPSDIAVEWESNGQPENNYKTIPPVLDSDGSFFLYSKLIVD

KSRWQQGNVFSCSVMHEALHNHYTQKSLSLSPGK

SEQ ID NO. 47

QVQLKESGPGLVAPSQSLSITCTVSGFSLTAYGVNWVRQPPGKGLEWLGMIWDDGSTDYNSALKSRLSISKDNS

KSQVFLKMNSLQTDDTARYYCAREGDVAFDYWGQGTTLTVSS

SEQ ID NO. 48

DIVMTQSPSSLAVSVGQKVIMSCKSSQSLLNGSNQKNYLAWYQQKPGQSPKLLVYFASTRDSGVPDRFIGSGSG

TDFILTISSVQAEDLADYFCLQHFGIPPTFGGGIKLEIKR (Note different leader sequence used for chimeric antibodies)

SEQ ID NO. 49

QVQLKESGPGLVAPSQSLSITCTVSGFSLTAYGVNWVRQPPGKGLEWLGMIWDDGSTDYNSALKSRLSISKDNS

KSQVFLKMNSLQTDDTARYYCAREGDVAFDYWGQGTTLTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSP

GK

SEQ ID NO. 50

DIVMTQSPSSLAVSVGQKVTMSCKSSQSLLNGSNQKNYLAWYQQKPGQSPKLLVYFASTRDSGVPDRFIGSGSG

TDFTLTISSVQAEDLADYFCLQHFGTPPTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

SEQ ID NO. 51

LQPGAEVPVVWAQEGAPAQLPCSPTIPLQDLSLLRRAGVTWQHQPDSGPPAAAPGHPLAPGPHPAAPSSWGPRP

RRYTVLSVGPGGLRSGRLPLQPRVQLDERGRQRGDFSLWLRPARRADAGEYRAAVHLRDRALSCRLRLRLGQAS

MTASPPGSLRASDWVILNCSFSRPDRPASVHWFRNRGQGRVPVRESPHHHLAESFLFLPQVSPMDSGPWGCILT

YRDGFNVSIMYNLTVLGLEPPTPLTVYAGAGSRVGLPCRLPAGVGTRSFLTAKWTPPGGGPDLLVTGDNGDFTL

RLEDVSQAQAGTYTCHIHLQEQQLNATVTLAIITVTPKSFGSPGSLGKLLCEVTPVSGQERFVWSSLDTPSQRS

FSGPWLEAQEAQLLSQPWQCQLYQGERLLGAAVYFTELSSPHHHHHH

SEQ ID NO. 52

PQPGAEISVVWAQEGAPAQLPCSPTIPLQDLSLLRRAGVTWQHQPDSGPPAPAPGHPPAPGHRPAAPYSWGPRP

RRYTVLSVGPGGLRSGRLPLQPRVQLDERGRQRGDFSLWLRPARRADAGEYRATVHLRDRALSCRLRLRVGQAS

MTASPPGSLRTSDWVILNCSFSRPDRPASVHWFRSRGQGRVPVQGSPHHHLAESFLFLPHVGPMDSGLWGCILT

YRDGFNVSIMYNLTVLGLEPATPLTVYAGAGSRVELPCRLPPAVGTQSFLTAKWAPPGGGPDLLVAGDNGDFTL

-continued

RLEDVSQAQAGTYICHIRLQGQQLNATVTLAIITVTPKSFGSPGSLGKLLCEVTPASGQEHFVWSPLNTPSQRS

FSGPWLEAQEAQLLSQPWQCQLHQGERLLGAAVYFTELSSPHHHHHH

SEQ ID NO. 53
PQPGAEISVVWAQEGAPAQLPCSPTIPLQDLSLLRRAGVTWQHQPDSGPPAPAPGHPPAPGHRPAAPYSWGPRP

RRYTVLSVGPGGLRSGRLPLQPRVQLDERGRQRGDFSLWLRPARRADAGEYRATVHLRDRALSCRLRLRVGQAS

MTASPPGSLRTSDWVILNCSFSRPDRPASVHWFRSRGQGQVPVQESPHHHLAESFLFLPHVGPMDSGLWGCILT

YRDGFNVSIMYNLTVLGLEPTTPLTVYAGAGSRVELPCRLPPAVGTQSFLTAKWAPPGGGPDLLVVGDNGNFTL

RLEDVSQAQAGTYICHIRLQGQQLNATVTLAIITVTPKSFGSPGSLGKLLCEVTPASGQERFVWSPLNTPSQRS

FSGPWLEAQEAQLLSQPWQCQLHQGERLLGAAVYFTELSSPHHHHHH

SEQ ID NO. 54
MGWSCIILFLVATATGVHS

SEQ ID NO. 55
MESQTQVLMFLLLWVSGACA

SEQ ID NO. 56
MPLLLLLPLL WAGALA

SEQ ID NO. 57
AAGAGCAGCCAGAGCCTGCTGAACCCCAGCAACCAGAAGAACTACCTGGCC

SEQ ID NO. 58
TTCGCCTCTACCAGGGATTCC

SEQ ID NO. 59
CTGCAGCACTTCGGCACCCCTCCCACT

SEQ ID NO. 60
GACATCCAGATGACCCAGAGCCCCTCTAGCCTCAGCGCCAGCGTGGGCGACAGGGTGACCATCACCTGCAAGAG

CAGCCAGAGCCTGCTGAACCCCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGT

SEQ ID NO. 61
GACATCCAGATGACCCAGAGCCCCTCTAGCCTCAGCGCCAGCGTGGGCGACAGGGTGACCATCACCTGCAAGAG

CAGCCAGAGCCTGCTGAACCCCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 62
GCCTACGGCGTCAAC

SEQ ID NO. 63
ATGATCTGGGACGACGGCAGCACCGACTACGACAGCGCCCTGAAGAGC

SEQ ID NO. 64
GAGGGCGACGTGGCCTTCGATTAC

SEQ ID NO. 65
CAGGTGCAGCTCCAGGAGAGCGGCCCCGGCCTGGTGAAGCCTAGCGAGACCCTGAGCCTGACCTGCACCGTGAG

CGGCTTCTCCCTGACCGCCTACGGCGTCAACTGGATCAGGCAGCCCCCCGGCAAAGGCCTGGAGTGGATTGGGA

TGATCTGGGACGACGGCAGCACCGACTACGACAGCGCCCTGAAGAGCAGGGTGACCATCAGCGTGGACACCAGC

-continued

AAGAACCAGTTCAGCCTGAAGCTGAGCAGCGTGACTGCCGCCGACACCGCCGTCTATTACTGCGCCAGGGAGGG

CGACGTGGCCTTCGATTACTGGGGCCAGGGCACACTAGTGACCGTGTCCAGC

SEQ ID NO. 66

CAGGTGCAGCTCCAGGAGAGCGGCCCCGGCCTGGTGAAGCCTAGCGAGACCCTGAGCCTGACCTGCACCGTGAG

CGGCTTCTCCCTGACCGCCTACGGCGTCAACTGGATCAGGCAGCCCCCCGGCAAAGGCCTGGAGTGGATTGGGA

TGATCTGGGACGACGGCAGCACCGACTACGACAGCGCCCTGAAGAGCAGGGTGACCATCAGCGTGGACACCAGC

AAGAACCAGTTCAGCCTGAAGCTGAGCAGCGTGACTGCCGCCGACACCGCCGTCTATTACTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 67

GACATCCAGATGACCCAGAGCCCCTCTAGCCTCAGCGCCAGCGTGGGCGACAGGGTGACCATCACCTGCAAGAG

CAGCCAGAGCCTGCTGAACCCCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 68

CAGGTGCAGCTCCAGGAGAGCGGCCCCGGCCTGGTGAAGCCTAGCGAGACCCTGAGCCTGACCTGCACCGTGAG

CGGCTTCTCCCTGACCGCCTACGGCGTCAACTGGATCAGGCAGCCCCCCGGCAAAGGCCTGGAGTGGATTGGGA

TGATCTGGGACGACGGCAGCACCGACTACAACAGCGCCCTGAAGAGCAGGGTGACCATCAGCGTGGACACCAGC

AAGAACCAGTTCAGCCTGAAGCTGAGCAGCGTGACTGCCGCCGACACCGCCGTCTATTACTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

-continued

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 69

GACATCCAGATGACCCAGAGCCCCTCTAGCCTCAGCGCCAGCGTGGGCGACAGGGTGACCATCACCTGCAAGAG

CAGCCAGAGCCTGCTGAACCCCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 70

CAGGTGCAGCTCGTGCAGAGCGGGGCCGAAGTCAAGAAACCCGGCAGCTCCGTGAAGGTGAGCTGCAAGGCCAG

CGGCTTCTCTCTCACTGCCTACGGCGTGAACTGGGTGAGGCAGGCTCCCGGCCAGGGCCTGGAGTGGATGGGCA

TGATCTGGGACGACGGCAGCACCGACTACAACAGCGCCCTGAAGAGCAGGGTGACCATCACCGCCGACAAGAGC

ACCAGCACCGCCTACATGGAACTGAGCAGCCTGAGGAGCGAGGACACCGCCGTGTACTATTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

-continued

SEQ ID NO. 71

GACATCCAGATGACCCAGAGCCCCTCTAGCCTCAGCGCCAGCGTGGGCGACAGGGTGACCATCACCTGCAAGAG
CAGCCAGAGCCTGCTGAACCCCAGCAACCAGAAGAACTACCTGGCCTGGTACCAGCAGAAACCCGGCAAGGCCC
CCAAGCTGCTGGTCTACTTCGCCTCTACCAGGGATTCCGGCGTCCCCAGCAGGTTCAGCGGCAGCGGCAGCGGC
ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCGAGTGC

SEQ ID NO. 72

CAGGTGCAGCTCCAGGAGAGCGGCCCCGGCCTGGTGAAGCCTAGCGAGACCCTGAGCCTGACCTGCACCGTGAG
CGGCTTCTCCCTGACCGCCTACGGCGTCAACTGGATCAGGCAGCCCCCCGGCAAAGGCCTGGAGTGGCTGGGGA
TGATCTGGGACGACGGCAGCACCGACTACAACAGCGCCCTGAAGAGCAGGCTGACCATCAGCAAGGACAACAGC
AAGAACCAGGTGAGCCTGAAGCTGAGCAGCGTGACTGCCGCCGACACCGCCGTCTATTACTGCGCCAGGGAGGG
CGACGTGGCCTTCGATTACTGGGGCCAGGGCACACTAGTGACCGTGTCCAGCGCCAGCACCAAGGGCCCCAGCG
TGTTCCCCCTGGCCCCCAGCAGCAAGAGCACCAGCGGCGGCACAGCCGCCCTGGGCTGCCTGGTGAAGGACTAC
TTCCCCGAACCGGTGACCGTGTCCTGGAACAGCGGAGCCCTGACCAGCGGCGTGCACACCTTCCCCGCCGTGCT
GCAGAGCAGCGGCCTGTACAGCCTGAGCAGCGTGGTGACCGTGCCCAGCAGCAGCCTGGGCACCCAGACCTACA
TCTGTAACGTGAACCACAAGCCCAGCAACACCAAGGTGGACAAGAAGGTGGAGCCCAAGAGCTGTGACAAGACC
CACACCTGCCCCCCCTGCCCTGCCCCCGAGCTGCTGGGAGGCCCCAGCGTGTTCCTGTTCCCCCCCAAGCCTAA
GGACACCCTGATGATCAGCAGAACCCCCGAGGTGACCTGTGTGGTGGTGGATGTGAGCCACGAGGACCCTGAGG
TGAAGTTCAACTGGTACGTGGACGGCGTGGAGGTGCACAATGCCAAGACCAAGCCCAGGGAGGAGCAGTACAAC
AGCACCTACCGGGTGGTGTCCGTGCTGACCGTGCTGCACCAGGATTGGCTGAACGGCAAGGAGTACAAGTGTAA
GGTGTCCAACAAGGCCCTGCCTGCCCCTATCGAGAAAACCATCAGCAAGGCCAAGGGCCAGCCCAGAGAGCCCC
AGGTGTACACCCTGCCCCCTAGCAGAGATGAGCTGACCAAGAACCAGGTGTCCCTGACCTGCCTGGTGAAGGGC
TTCTACCCCAGCGACATCGCCGTGGAGTGGGAGAGCAACGGCCAGCCCGAGAACAACTACAAGACCACCCCCCC
TGTGCTGGACAGCGATGGCAGCTTCTTCCTGTACAGCAAGCTGACCGTGGACAAGAGCAGATGGCAGCAGGGCA
ACGTGTTCAGCTGCTCCGTGATGCACGAGGCCCTGCACAATCACTACACCCAGAAGAGCCTGAGCCTGTCCCCT
GGCAAG

SEQ ID NO. 73

GACATCCAGATGACCCAGAGCCCCTCTAGCCTCAGCGCCAGCGTGGGCGACAGGGTGACCATCACCTGCAAGAG
CAGCCAGAGCCTGCTGAACCCCAGCAACCAGAAGAACTACCTGGCCTGGTACCAGCAGAAACCCGGCAAGGCCC
CCAAGCTGCTGGTCTACTTCGCCTCTACCAGGGATTCCGGCGTCCCCAGCAGGTTCAGCGGCAGCGGCAGCGGC
ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCGAGTGC

-continued

SEQ ID NO. 74
CAGGTGCAGCTCGTGCAGAGCGGGGCCGAAGTCAAGAAACCCGGCAGCTCCGTGAAGGTGAGCTGCAAGGCCAG
CGGCTTCTCTCTCACTGCCTACGGCGTGAACTGGGTGAGGCAGGCTCCCGGCCAGGGCCTGGAGTGGATGGGCA
TGATCTGGGACGACGGCAGCACCGACTACGACAGCGCCCTGAAGAGCAGGGTGACCATCACCGCCGACAAGAGC
ACCAGCACCGCCTACATGGAACTGAGCAGCCTGAGGAGCGAGGACACCGCCGTGTACTATTGCGCCAGGGAGGG
CGACGTGGCCTTCGATTACTGGGGCCAGGGCACACTAGTGACCGTGTCCAGCGCCAGCACCAAGGGCCCCAGCG
TGTTCCCCCTGGCCCCCAGCAGCAAGAGCACCAGCGGCGGCACAGCCGCCCTGGGCTGCCTGGTGAAGGACTAC
TTCCCCGAACCGGTGACCGTGTCCTGGAACAGCGGAGCCCTGACCAGCGGCGTGCACACCTTCCCCGCCGTGCT
GCAGAGCAGCGGCCTGTACAGCCTGAGCAGCGTGGTGACCGTGCCCAGCAGCAGCCTGGGCACCCAGACCTACA
TCTGTAACGTGAACCACAAGCCCAGCAACACCAAGGTGGACAAGAAGGTGGAGCCCAAGAGCTGTGACAAGACC
CACACCTGCCCCCCCTGCCCTGCCCCCGAGCTGCTGGGAGGCCCCAGCGTGTTCCTGTTCCCCCCCAAGCCTAA
GGACACCCTGATGATCAGCAGAACCCCCGAGGTGACCTGTGTGGTGGTGGATGTGAGCCACGAGGACCCTGAGG
TGAAGTTCAACTGGTACGTGGACGGCGTGGAGGTGCACAATGCCAAGACCAAGCCCAGGGAGGAGCAGTACAAC
AGCACCTACCGGGTGGTGTCCGTGCTGACCGTGCTGCACCAGGATTGGCTGAACGGCAAGGAGTACAAGTGTAA
GGTGTCCAACAAGGCCCTGCCTGCCCCTATCGAGAAAACCATCAGCAAGGCCAAGGGCCAGCCCAGAGAGCCCC
AGGTGTACACCCTGCCCCCTAGCAGAGATGAGCTGACCAAGAACCAGGTGTCCCTGACCTGCCTGGTGAAGGGC
TTCTACCCCAGCGACATCGCCGTGGAGTGGGAGAGCAACGGCCAGCCCGAGAACAACTACAAGACCACCCCCCC
TGTGCTGGACAGCGATGGCAGCTTCTTCCTGTACAGCAAGCTGACCGTGGACAAGAGCAGATGGCAGCAGGGCA
ACGTGTTCAGCTGCTCCGTGATGCACGAGGCCCTGCACAATCACTACACCCAGAAGAGCCTGAGCCTGTCCCCT
GGCAAG

SEQ ID NO. 75
GACATCCAGATGACCCAGAGCCCCTCTAGCCTCAGCGCCAGCGTGGGCGACAGGGTGACCATCACCTGCAAGAG
CAGCCAGAGCCTGCTGAACCCCAGCAACCAGAAGAACTACCTGGCCTGGTACCAGCAGAAACCCGGCAAGGCCC
CCAAGCTGCTGGTCTACTTCGCCTCTACCAGGGATTCCGGCGTCCCCAGCAGGTTCAGCGGCAGCGGCAGCGGC
ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCGAGTGC

SEQ ID NO. 76
CAGGTGCAGCTCCAGGAGAGCGGCCCCGGCCTGGTGAAGCCTAGCGAGACCCTGAGCCTGACCTGCACCGTGAG
CGGCTTCTCCCTGACCGCCTACGGCGTCAACTGGATCAGGCAGCCCCCCGGCAAAGGCCTGGAGTGGATTGGGA
TGATCTGGGACGACGGCAGCACCGACTACAACAGCGCCCTGAAGAGCAGGGTGACCATCAGCAAGGACAACAGC
AAGAACCAGGTGAGCCTGAAGCTGAGCAGCGTGACTGCCGCCGACACCGCCGTCTATTACTGCGCCAGGGAGGG
CGACGTGGCCTTCGATTACTGGGGCCAGGGCACACTAGTGACCGTGTCCAGCGCCAGCACCAAGGGCCCCAGCG
TGTTCCCCCTGGCCCCCAGCAGCAAGAGCACCAGCGGCGGCACAGCCGCCCTGGGCTGCCTGGTGAAGGACTAC
TTCCCCGAACCGGTGACCGTGTCCTGGAACAGCGGAGCCCTGACCAGCGGCGTGCACACCTTCCCCGCCGTGCT
GCAGAGCAGCGGCCTGTACAGCCTGAGCAGCGTGGTGACCGTGCCCAGCAGCAGCCTGGGCACCCAGACCTACA
TCTGTAACGTGAACCACAAGCCCAGCAACACCAAGGTGGACAAGAAGGTGGAGCCCAAGAGCTGTGACAAGACC
CACACCTGCCCCCCCTGCCCTGCCCCCGAGCTGCTGGGAGGCCCCAGCGTGTTCCTGTTCCCCCCCAAGCCTAA
GGACACCCTGATGATCAGCAGAACCCCCGAGGTGACCTGTGTGGTGGTGGATGTGAGCCACGAGGACCCTGAGG

-continued

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 77

GACATCCAGATGACCCAGAGCCCCTCTAGCCTCAGCGCCAGCGTGGGCGACAGGGTGACCATCACCTGCAAGAG

CAGCCAGAGCCTGCTGAACCCCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 78

CAGGTGCAGCTCGTGCAGAGCGGGGCCGAAGTCAAGAAACCCGGCAGCTCCGTGAAGGTGAGCTGCAAGGCCAG

CGGCGGCACCTTCAGCGCCTACGGCGTGAACTGGGTGAGGCAGGCTCCCGGCCAGGGCCTGGAGTGGATGGGCA

TGATCTGGGACGACGGCAGCACCGACTACGACAGCGCCCTGAAGAGCAGGGTGACCATCACCGCCGACAAGAGC

ACCAGCACCGCCTACATGGAACTGAGCAGCCTGAGGAGCGAGGACACCGCCGTGTACTATTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 79

GACATCCAGATGACCCAGAGCCCCTCTAGCCTCAGCGCCAGCGTGGGCGACAGGGTGACCATCACCTGCAAGAG

CAGCCAGAGCCTGCTGAACCCCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

-continued

ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCGAGTGC

SEQ ID NO. 80
CAGGTGCAGCTCCAGGAGAGCGGCCCCGGCCTGGTGAAGCCTAGCGAGACCCTGAGCCTGACCTGCACCGTGAG
CGGCGGCTCCATCAGCGCCTACGGCGTCAACTGGATCAGGCAGCCCCCCGGCAAAGGCCTGGAGTGGATTGGGA
TGATCTGGGACGACGGCAGCACCGACTACGACAGCGCCCTGAAGAGCAGGGTGACCATCAGCGTGGACACCAGC
AAGAACCAGTTCAGCCTGAAGCTGAGCAGCGTGACTGCCGCCGACACCGCCGTCTATTACTGCGCCAGGGAGGG
CGACGTGGCCTTCGATTACTGGGGCCAGGGCACACTAGTGACCGTGTCCAGCGCCAGCACCAAGGGCCCCAGCG
TGTTCCCCCTGGCCCCCAGCAGCAAGAGCACCAGCGGCGGCACAGCCGCCCTGGGCTGCCTGGTGAAGGACTAC
TTCCCCGAACCGGTGACCGTGTCCTGGAACAGCGGAGCCCTGACCAGCGGCGTGCACACCTTCCCCGCCGTGCT
GCAGAGCAGCGGCCTGTACAGCCTGAGCAGCGTGGTGACCGTGCCCAGCAGCAGCCTGGGCACCCAGACCTACA
TCTGTAACGTGAACCACAAGCCCAGCAACACCAAGGTGGACAAGAAGGTGGAGCCCAAGAGCTGTGACAAGACC
CACACCTGCCCCCCCTGCCCTGCCCCCGAGCTGCTGGGAGGCCCCAGCGTGTTCCTGTTCCCCCCCAAGCCTAA
GGACACCCTGATGATCAGCAGAACCCCCGAGGTGACCTGTGTGGTGGTGGATGTGAGCCACGAGGACCCTGAGG
TGAAGTTCAACTGGTACGTGGACGGCGTGGAGGTGCACAATGCCAAGACCAAGCCCAGGGAGGAGCAGTACAAC
AGCACCTACCGGGTGGTGTCCGTGCTGACCGTGCTGCACCAGGATTGGCTGAACGGCAAGGAGTACAAGTGTAA
GGTGTCCAACAAGGCCCTGCCTGCCCCTATCGAGAAAACCATCAGCAAGGCCAAGGGCCAGCCCAGAGAGCCCC
AGGTGTACACCCTGCCCCCTAGCAGAGATGAGCTGACCAAGAACCAGGTGTCCCTGACCTGCCTGGTGAAGGGC
TTCTACCCCAGCGACATCGCCGTGGAGTGGGAGAGCAACGGCCAGCCCGAGAACAACTACAAGACCACCCCCCC
TGTGCTGGACAGCGATGGCAGCTTCTTCCTGTACAGCAAGCTGACCGTGGACAAGAGCAGATGGCAGCAGGGCA
ACGTGTTCAGCTGCTCCGTGATGCACGAGGCCCTGCACAATCACTACACCCAGAAGAGCCTGAGCCTGTCCCCT
GGCAAG

SEQ ID NO. 81
GACATCCAGATGACCCAGAGCCCCTCTAGCCTCAGCGCCAGCGTGGGCGACAGGGTGACCATCACCTGCAAGAG
CAGCCAGAGCCTGCTGAACCCCAGCAACCAGAAGAACTACCTGGCCTGGTACCAGCAGAAACCCGGCAAGGCCC
CCAAGCTGCTGGTCTACTTCGCCTCTACCAGGGATTCCGGCGTCCCCAGCAGGTTCAGCGGCAGCGGCAGCGGC
ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCGAGTGC

SEQ ID NO. 82
CAGGTGCAGCTCGTGCAGAGCGGGGCCGAAGTCAAGAAACCCGGCAGCTCCGTGAAGGTGAGCTGCAAGGCCAG
CGGCGGCACCTTCAGCGCCTACGGCGTGAACTGGGTGAGGCAGGCTCCCGGCCAGGGCCTGGAGTGGATGGGCA
TGATCTGGGACGACGGCAGCACCGACTACAACAGCGCCCTGAAGAGCAGGGTGACCATCACCGCCGACAAGAGC
ACCAGCACCGCCTACATGGAACTGAGCAGCCTGAGGAGCGAGGACACCGCCGTGTACTATTGCGCCAGGGAGGG
CGACGTGGCCTTCGATTACTGGGGCCAGGGCACACTAGTGACCGTGTCCAGCGCCAGCACCAAGGGCCCCAGCG

-continued

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 83

GACATCCAGATGACCCAGAGCCCCTCTAGCCTCAGCGCCAGCGTGGGCGACAGGGTGACCATCACCTGCAAGAG

CAGCCAGAGCCTGCTGAACCCCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 84

CAGGTGCAGCTCCAGGAGAGCGGCCCCGGCCTGGTGAAGCCTAGCGAGACCCTGAGCCTGACCTGCACCGTGAG

CGGCGGCTCCATCAGCGCCTACGGCGTCAACTGGATCAGGCAGCCCCCCGGCAAAGGCCTGGAGTGGATTGGGA

TGATCTGGGACGACGGCAGCACCGACTACAACAGCGCCCTGAAGAGCAGGGTGACCATCAGCGTGGACACCAGC

AAGAACCAGTTCAGCCTGAAGCTGAGCAGCGTGACTGCCGCCGACACCGCCGTCTATTACTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

-continued

TGTGCTGGACAGCGATGGCAGCTTCTTCCTGTACAGCAAGCTGACCGTGGACAAGAGCAGATGGCAGCAGGGCA
ACGTGTTCAGCTGCTCCGTGATGCACGAGGCCCTGCACAATCACTACACCCAGAAGAGCCTGAGCCTGTCCCCT
GGCAAG

SEQ ID NO. 85

GACATCCAGATGACCCAGAGCCCCTCTAGCCTCAGCGCCAGCGTGGGCGACAGGGTGACCATCACCTGCAAGAG
CAGCCAGAGCCTGCTGAACGGCAGCAACCAGAAGAACTACCTGGCCTGGTACCAGCAGAAACCCGGCAAGGCCC
CCAAGCTGCTGGTCTACTTCGCCTCTACCAGGGATTCCGGCGTCCCCAGCAGGTTCAGCGGCAGCGGCAGCGGC
ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCGAGTGC

SEQ ID NO. 86

CAGGTGCAGCTCCAGGAGAGCGGCCCCGGCCTGGTGAAGCCTAGCGAGACCCTGAGCCTGACCTGCACCGTGAG
CGGCTTCTCCCTGACCGCCTACGGCGTCAACTGGATCAGGCAGCCCCCCGGCAAAGGCCTGGAGTGGATTGGGA
TGATCTGGGACGACGGCAGCACCGACTACAACAGCGCCCTGAAGAGCAGGGTGACCATCAGCGTGGACACCAGC
AAGAACCAGTTCAGCCTGAAGCTGAGCAGCGTGACTGCCGCCGACACCGCCGTCTATTACTGCGCCAGGGAGGG
CGACGTGGCCTTCGATTACTGGGGCCAGGGCACACTAGTGACCGTGTCCAGCGCCAGCACCAAGGGCCCCAGCG
TGTTCCCCCTGGCCCCCAGCAGCAAGAGCACCAGCGGCGGCACAGCCGCCCTGGGCTGCCTGGTGAAGGACTAC
TTCCCCGAACCGGTGACCGTGTCCTGGAACAGCGGAGCCCTGACCAGCGGCGTGCACACCTTCCCCGCCGTGCT
GCAGAGCAGCGGCCTGTACAGCCTGAGCAGCGTGGTGACCGTGCCCAGCAGCAGCCTGGGCACCCAGACCTACA
TCTGTAACGTGAACCACAAGCCCAGCAACACCAAGGTGGACAAGAAGGTGGAGCCCAAGAGCTGTGACAAGACC
CACACCTGCCCCCCCTGCCCTGCCCCCGAGCTGCTGGGAGGCCCCAGCGTGTTCCTGTTCCCCCCCAAGCCTAA
GGACACCCTGATGATCAGCAGAACCCCCGAGGTGACCTGTGTGGTGGTGGATGTGAGCCACGAGGACCCTGAGG
TGAAGTTCAACTGGTACGTGGACGGCGTGGAGGTGCACAATGCCAAGACCAAGCCCAGGGAGGAGCAGTACAAC
AGCACCTACCGGGTGGTGTCCGTGCTGACCGTGCTGCACCAGGATTGGCTGAACGGCAAGGAGTACAAGTGTAA
GGTGTCCAACAAGGCCCTGCCTGCCCCTATCGAGAAAACCATCAGCAAGGCCAAGGGCCAGCCCAGAGAGCCCC
AGGTGTACACCCTGCCCCCTAGCAGAGATGAGCTGACCAAGAACCAGGTGTCCCTGACCTGCCTGGTGAAGGGC
TTCTACCCCAGCGACATCGCCGTGGAGTGGGAGAGCAACGGCCAGCCCGAGAACAACTACAAGACCACCCCCCC
TGTGCTGGACAGCGATGGCAGCTTCTTCCTGTACAGCAAGCTGACCGTGGACAAGAGCAGATGGCAGCAGGGCA
ACGTGTTCAGCTGCTCCGTGATGCACGAGGCCCTGCACAATCACTACACCCAGAAGAGCCTGAGCCTGTCCCCT
GGCAAG

SEQ ID NO. 87

GACATCCAGATGACCCAGAGCCCCTCTAGCCTCAGCGCCAGCGTGGGCGACAGGGTGACCATCACCTGCAAGAG
CAGCCAGAGCCTGCTGAACGGCAGCAACCAGAAGAACTACCTGGCCTGGTACCAGCAGAAACCCGGCAAGGCCC
CCAAGCTGCTGGTCTACTTCGCCTCTACCAGGGATTCCGGCGTCCCCAGCAGGTTCAGCGGCAGCGGCAGCGGC
ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA

-continued

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 88

CAGGTGCAGCTCCAGGAGAGCGGCCCCGGCCTGGTGAAGCCTAGCGAGACCCTGAGCCTGACCTGCACCGTGAG

CGGCTTCTCCCTGACCGCCTACGGCGTCAACTGGATCAGGCAGCCCCCCGGCAAAGGCCTGGAGTGGATTGGGA

TGATCTGGGACGACGGCAGCACCGACTACGACAGCGCCCTGAAGAGCAGGGTGACCATCAGCGTGGACACCAGC

AAGAACCAGTTCAGCCTGAAGCTGAGCAGCGTGACTGCCGCCGACACCGCCGTCTATTACTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 89

GACATCCAGATGACCCAGAGCCCCTCTAGCCTCAGCGCCAGCGTGGGCGACAGGGTGACCATCACCTGCAAGAG

CAGCCAGAGCCTGCTGAACGGCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 90

CAGGTGCAGCTCGTGCAGAGCGGGGCCGAAGTCAAGAAACCCGGCAGCTCCGTGAAGGTGAGCTGCAAGGCCAG

CGGCTTCTCTCTCACTGCCTACGGCGTGAACTGGGTGAGGCAGGCTCCCGGCCAGGGCCTGGAGTGGATGGGCA

TGATCTGGGACGACGGCAGCACCGACTACAACAGCGCCCTGAAGAGCAGGGTGACCATCACCGCCGACAAGAGC

ACCAGCACCGCCTACATGGAACTGAGCAGCCTGAGGAGCGAGGACACCGCCGTGTACTATTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

-continued

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 91

GACATCCAGATGACCCAGAGCCCCTCTAGCCTCAGCGCCAGCGTGGGCGACAGGGTGACCATCACCTGCAAGAG

CAGCCAGAGCCTGCTGAACGGCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 92

CAGGTGCAGCTCGTGCAGAGCGGGGCCGAAGTCAAGAAACCCGGCAGCTCCGTGAAGGTGAGCTGCAAGGCCAG

CGGCTTCTCTCTCACTGCCTACGGCGTGAACTGGGTGAGGCAGGCTCCCGGCCAGGGCCTGGAGTGGATGGGCA

TGATCTGGGACGACGGCAGCACCGACTACGACAGCGCCCTGAAGAGCAGGGTGACCATCACCGCCGACAAGAGC

ACCAGCACCGCCTACATGGAACTGAGCAGCCTGAGGAGCGAGGACACCGCCGTGTACTATTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

-continued

SEQ ID NO. 93
GACATCCAGATGACCCAGAGCCCCTCTAGCCTCAGCGCCAGCGTGGGCGACAGGGTGACCATCACCTGCAAGAG
CAGCCAGAGCCTGCTGAACGGCAGCAACCAGAAGAACTACCTGGCCTGGTACCAGCAGAAACCCGGCAAGGCCC
CCAAGCTGCTGGTCTACTTCGCCTCTACCAGGGATTCCGGCGTCCCCAGCAGGTTCAGCGGCAGCGGCAGCGGC
ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCGAGTGC

SEQ ID NO. 94
CAGGTGCAGCTCGTGCAGAGCGGGGCCGAAGTCAAGAAACCCGGCAGCTCCGTGAAGGTGAGCTGCAAGGCCAG
CGGCGGCACCTTCAGCGCCTACGGCGTGAACTGGGTGAGGCAGGCTCCCGGCCAGGGCCTGGAGTGGATGGGCA
TGATCTGGGACGACGGCAGCACCGACTACGACAGCGCCCTGAAGAGCAGGGTGACCATCACCGCCGACAAGAGC
ACCAGCACCGCCTACATGGAACTGAGCAGCCTGAGGAGCGAGGACACCGCCGTGTACTATTGCGCCAGGGAGGG
CGACGTGGCCTTCGATTACTGGGGCCAGGGCACACTAGTGACCGTGTCCAGCGCCAGCACCAAGGGCCCCAGCG
TGTTCCCCCTGGCCCCCAGCAGCAAGAGCACCAGCGGCGGCACAGCCGCCCTGGGCTGCCTGGTGAAGGACTAC
TTCCCCGAACCGGTGACCGTGTCCTGGAACAGCGGAGCCCTGACCAGCGGCGTGCACACCTTCCCCGCCGTGCT
GCAGAGCAGCGGCCTGTACAGCCTGAGCAGCGTGGTGACCGTGCCCAGCAGCAGCCTGGGCACCCAGACCTACA
TCTGTAACGTGAACCACAAGCCCAGCAACACCAAGGTGGACAAGAAGGTGGAGCCCAAGAGCTGTGACAAGACC
CACACCTGCCCCCCCTGCCCTGCCCCCGAGCTGCTGGGAGGCCCCAGCGTGTTCCTGTTCCCCCCCAAGCCTAA
GGACACCCTGATGATCAGCAGAACCCCCGAGGTGACCTGTGTGGTGGTGGATGTGAGCCACGAGGACCCTGAGG
TGAAGTTCAACTGGTACGTGGACGGCGTGGAGGTGCACAATGCCAAGACCAAGCCCAGGGAGGAGCAGTACAAC
AGCACCTACCGGGTGGTGTCCGTGCTGACCGTGCTGCACCAGGATTGGCTGAACGGCAAGGAGTACAAGTGTAA
GGTGTCCAACAAGGCCCTGCCTGCCCCTATCGAGAAAACCATCAGCAAGGCCAAGGGCCAGCCCAGAGAGCCCC
AGGTGTACACCCTGCCCCCTAGCAGAGATGAGCTGACCAAGAACCAGGTGTCCCTGACCTGCCTGGTGAAGGGC
TTCTACCCCAGCGACATCGCCGTGGAGTGGGAGAGCAACGGCCAGCCCGAGAACAACTACAAGACCACCCCCCC
TGTGCTGGACAGCGATGGCAGCTTCTTCCTGTACAGCAAGCTGACCGTGGACAAGAGCAGATGGCAGCAGGGCA
ACGTGTTCAGCTGCTCCGTGATGCACGAGGCCCTGCACAATCACTACACCCAGAAGAGCCTGAGCCTGTCCCCT
GGCAAG

SEQ ID NO. 95
GACATCCAGATGACCCAGAGCCCCTCTAGCCTCAGCGCCAGCGTGGGCGACAGGGTGACCATCACCTGCAAGAG
CAGCCAGAGCCTGCTGAACGGCAGCAACCAGAAGAACTACCTGGCCTGGTACCAGCAGAAACCCGGCAAGGCCC
CCAAGCTGCTGGTCTACTTCGCCTCTACCAGGGATTCCGGCGTCCCCAGCAGGTTCAGCGGCAGCGGCAGCGGC
ACCGACTTCACACTGACCATCAGCAGCCTGCAGCCCGAGGACTTCGCCACCTACTACTGCCTGCAGCACTTCGG
CACCCCTCCCACTTTTGGCCAGGGCACCAAGCTGGAGATTAAGCGTACGGTGGCCGCCCCCAGCGTGTTCATCT
TCCCCCCCAGCGATGAGCAGCTGAAGAGCGGCACCGCCAGCGTGGTGTGTCTGCTGAACAACTTCTACCCCCGG
GAGGCCAAGGTGCAGTGGAAGGTGGACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGGCCGACTACGAGAAGCACAAGGTGT
ACGCCTGTGAGGTGACCCACCAGGGCCTGTCCAGCCCCGTGACCAAGAGCTTCAACCGGGGCGAGTGC

-continued

SEQ ID NO. 96
CAGGTGCAGCTCCAGGAGAGCGGCCCCGGCCTGGTGAAGCCTAGCGAGACCCTGAGCCTGACCTGCACCGTGAG

CGGCGGCTCCATCAGCGCCTACGGCGTCAACTGGATCAGGCAGCCCCCCGGCAAAGGCCTGGAGTGGATTGGGA

TGATCTGGGACGACGGCAGCACCGACTACGACAGCGCCCTGAAGAGCAGGGTGACCATCAGCGTGGACACCAGC

AAGAACCAGTTCAGCCTGAAGCTGAGCAGCGTGACTGCCGCCGACACCGCCGTCTATTACTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 97
GACATCCAGATGACCCAGAGCCCCTCTAGCCTCAGCGCCAGCGTGGGCGACAGGGTGACCATCACCTGCAAGAG

CAGCCAGAGCCTGCTGAACGGCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 98
CAGGTGCAGCTCGTGCAGAGCGGGGCCGAAGTCAAGAAACCCGGCAGCTCCGTGAAGGTGAGCTGCAAGGCCAG

CGGCGGCACCTTCAGCGCCTACGGCGTGAACTGGGTGAGGCAGGCTCCCGGCCAGGGCCTGGAGTGGATGGGCA

TGATCTGGGACGACGGCAGCACCGACTACAACAGCGCCCTGAAGAGCAGGGTGACCATCACCGCCGACAAGAGC

ACCAGCACCGCCTACATGGAACTGAGCAGCCTGAGGAGCGAGGACACCGCCGTGTACTATTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

-continued

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 99

GACATCCAGATGACCCAGAGCCCCTCTAGCCTCAGCGCCAGCGTGGGCGACAGGGTGACCATCACCTGCAAGAG

CAGCCAGAGCCTGCTGAACGGCAGCAACCAGAAGAACTACCTGGCCTGGTACCAGCAGAAACCCGGCAAGGCCC

CCAAGCTGCTGGTCTACTTCGCCTCTACCAGGGATTCCGGCGTCCCCAGCAGGTTCAGCGGCAGCGGCAGCGGC

ACCGACTTCACACTGACCATCAGCAGCCTGCAGCCCGAGGACTTCGCCACCTACTACTGCCTGCAGCACTTCGG

CACCCCTCCCACTTTTGGCCAGGGCACCAAGCTGGAGATTAAGCGTACGGTGGCCGCCCCCAGCGTGTTCATCT

TCCCCCCCAGCGATGAGCAGCTGAAGAGCGGCACCGCCAGCGTGGTGTGTCTGCTGAACAACTTCTACCCCCGG

GAGGCCAAGGTGCAGTGGAAGGTGGACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGGCCGACTACGAGAAGCACAAGGTGT

ACGCCTGTGAGGTGACCCACCAGGGCCTGTCCAGCCCCGTGACCAAGAGCTTCAACCGGGGCGAGTGC

SEQ ID NO. 100

CAGGTGCAGCTCCAGGAGAGCGGCCCCGGCCTGGTGAAGCCTAGCGAGACCCTGAGCCTGACCTGCACCGTGAG

CGGCGGCTCCATCAGCGCCTACGGCGTCAACTGGATCAGGCAGCCCCCCGGCAAAGGCCTGGAGTGGATTGGGA

TGATCTGGGACGACGGCAGCACCGACTACAACAGCGCCCTGAAGAGCAGGGTGACCATCAGCGTGGACACCAGC

AAGAACCAGTTCAGCCTGAAGCTGAGCAGCGTGACTGCCGCCGACACCGCCGTCTATTACTGCGCCAGGGAGGG

CGACGTGGCCTTCGATTACTGGGGCCAGGGCACACTAGTGACCGTGTCCAGCGCCAGCACCAAGGGCCCCAGCG

TGTTCCCCCTGGCCCCCAGCAGCAAGAGCACCAGCGGCGGCACAGCCGCCCTGGGCTGCCTGGTGAAGGACTAC

TTCCCCGAACCGGTGACCGTGTCCTGGAACAGCGGAGCCCTGACCAGCGGCGTGCACACCTTCCCCGCCGTGCT

GCAGAGCAGCGGCCTGTACAGCCTGAGCAGCGTGGTGACCGTGCCCAGCAGCAGCCTGGGCACCCAGACCTACA

TCTGTAACGTGAACCACAAGCCCAGCAACACCAAGGTGGACAAGAAGGTGGAGCCCAAGAGCTGTGACAAGACC

CACACCTGCCCCCCCTGCCCTGCCCCCGAGCTGCTGGGAGGCCCCAGCGTGTTCCTGTTCCCCCCCAAGCCTAA

GGACACCCTGATGATCAGCAGAACCCCCGAGGTGACCTGTGTGGTGGTGGATGTGAGCCACGAGGACCCTGAGG

TGAAGTTCAACTGGTACGTGGACGGCGTGGAGGTGCACAATGCCAAGACCAAGCCCAGGGAGGAGCAGTACAAC

AGCACCTACCGGGTGGTGTCCGTGCTGACCGTGCTGCACCAGGATTGGCTGAACGGCAAGGAGTACAAGTGTAA

GGTGTCCAACAAGGCCCTGCCTGCCCCTATCGAGAAAACCATCAGCAAGGCCAAGGGCCAGCCCAGAGAGCCCC

AGGTGTACACCCTGCCCCCTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAACTACAAGACCACCCCCCC

TGTGCTGGACAGCGATGGCAGCTTCTTCCTGTACAGCAAGCTGACCGTGGACAAGAGCAGATGGCAGCAGGGCA

ACGTGTTCAGCTGCTCCGTGATGCACGAGGCCCTGCACAATCACTACACCCAGAAGAGCCTGAGCCTGTCCCCT

GGCAAG

SEQ ID NO. 101

ACGGTGGCCGCCCCCAGCGTGTTCATCTTCCCCCCCAGCGATGAGCAGCTGAAGAGCGGCACCGCCAGCGTGGT

GTGTCTGCTGAACAACTTCTACCCCCGGGAGGCCAAGGTGCAGTGGAAGGTGGACAATGCCCTGCAGAGCGGCA

ACAGCCAGGAGAGCGTGACCGAGCAGGACAGCAAGGACTCCACCTACAGCCTGAGCAGCACCCTGACCCTGAGC

-continued

AAGGCCGACTACGAGAAGCACAAGGTGTACGCCTGTGAGGTGACCCACCAGGGCCTGTCCAGCCCCGTGACCAA

GAGCTTCAACCGGGGCGAGTGC

SEQ ID NO. 102

GCCAGCACCAAGGGCCCCAGCGTGTTCCCCCTGGCCCCCAGCAGCAAGAGCACCAGCGGCGGCACAGCCGCCCT

GGGCTGCCTGGTGAAGGACTACTTCCCCGAACCGGTGACCGTGTCCTGGAACAGCGGAGCCCTGACCAGCGGCG

TGCACACCTTCCCCGCCGTGCTGCAGAGCAGCGGCCTGTACAGCCTGAGCAGCGTGGTGACCGTGCCCAGCAGC

AGCCTGGGCACCCAGACCTACATCTGTAACGTGAACCACAAGCCCAGCAACACCAAGGTGGACAAGAAGGTGGA

GCCCAAGAGCTGTGACAAGACCCACACCTGCCCCCCCTGCCCTGCCCCCGAGCTGCTGGGAGGCCCCAGCGTGT

TCCTGTTCCCCCCCAAGCCTAAGGACACCCTGATGATCAGCAGAACCCCCGAGGTGACCTGTGTGGTGGTGGAT

GTGAGCCACGAGGACCCTGAGGTGAAGTTCAACTGGTACGTGGACGGCGTGGAGGTGCACAATGCCAAGACCAA

GCCCAGGGAGGAGCAGTACAACAGCACCTACCGGGTGGTGTCCGTGCTGACCGTGCTGCACCAGGATTGGCTGA

ACGGCAAGGAGTACAAGTGTAAGGTGTCCAACAAGGCCCTGCCTGCCCCTATCGAGAAAACCATCAGCAAGGCC

AAGGGCCAGCCCAGAGAGCCCCAGGTGTACACCCTGCCCCCTAGCAGAGATGAGCTGACCAAGAACCAGGTGTC

CCTGACCTGCCTGGTGAAGGGCTTCTACCCCAGCGACATCGCCGTGGAGTGGGAGAGCAACGGCCAGCCCGAGA

ACAACTACAAGACCACCCCCCCTGTGCTGGACAGCGATGGCAGCTTCTTCCTGTACAGCAAGCTGACCGTGGAC

AAGAGCAGATGGCAGCAGGGCAACGTGTTCAGCTGCTCCGTGATGCACGAGGCCCTGCACAATCACTACACCCA

GAAGAGCCTGAGCCTGTCCCCTGGCAAG

SEQ ID NO. 103

CAGGTGCAGCTGAAGGAGTCAGGTCCTGGCCTGGTGGCGCCCTCACAGAGCCTGTCCATCACATGCACCGTCTC

AGGGTTCTCATTAACCGCCTATGGTGTAAACTGGGTTCGCCAGCCTCCAGGAAAGGGTCTGGAGTGGCTGGGAA

TGATATGGGATGATGGAAGCACAGACTATAATTCAGCTCTCAAATCCAGACTGAGCATCAGTAAGGACAACTCC

AAGAGCCAAGTTTTCTTAAAAATGAACAGTCTGCAAACTGATGACACAGCCAGGTACTACTGTGCCAGAGAAGG

GGACGTAGCCTTTGACTACTGGGGCCAAGGCACCACTCTCACAGTCTCCTCA

SEQ ID NO. 104

GACATTGTGATGACACAGTCTCCCTCCTCCCTGGCTGTGTCAGTAGGACAGAAGGTCACTATGAGCTGCAAGTC

CAGTCAGAGCCTTTTAAATGGTAGCAATCAAAAGAACTACTTGGCCTGGTACCAGCAGAAACCAGGACAGTCTC

CTAAACTTCTGGTATACTTTGCATCCACTAGGGATTCTGGGGTCCCTGATCGCTTCATAGGCAGTGGATCTGGG

ACAGATTTCACTCTTACCATCAGCAGTGTGCAGGCTGAAGACCTGGCAGATTACTTCTGTCTGCAACATTTTGG

CACTCCTCCGACGTTCGGTGGAGGCACCAAACTGGAAATCAAACGG

SEQ ID NO. 105

CAGGTGCAGCTGAAGGAGTCAGGTCCTGGCCTGGTGGCGCCCTCACAGAGCCTGTCCATCACATGCACCGTCTC

AGGGTTCTCATTAACCGCCTATGGTGTAAACTGGGTTCGCCAGCCTCCAGGAAAGGGTCTGGAGTGGCTGGGAA

TGATATGGGATGATGGAAGCACAGACTATAATTCAGCTCTCAAATCCAGACTGAGCATCAGTAAGGACAACTCC

AAGAGCCAAGTTTTCTTAAAAATGAACAGTCTGCAAACTGATGACACAGCCAGGTACTACTGTGCCAGAGAAGG

GGACGTAGCCTTTGACTACTGGGGCCAAGGCACCACTCTCACAGTCTCCTCAGCTAGCACCAAGGGCCCATCGG

TCTTCCCCCTGGCACCCTCCTCCAAGAGCACCTCTGGGGGCACAGCGGCCCTGGGCTGCCTGGTCAAGGACTAC

TTCCCCGAACCGGTGACGGTGTCGTGGAACTCAGGCGCCCTGACCAGCGGCGTGCACACCTTCCCGGCTGTCCT

ACAGTCCTCAGGACTCTACTCCCTCAGCAGCGTGGTGACCGTGCCCTCCAGCAGCTTGGGCACCCAGACCTACA

TCTGCAACGTGAATCACAAGCCCAGCAACACCAAGGTGGACAAGAAAGTTGAGCCCAAATCTTGTGACAAAACT

CACACATGCCCACCGTGCCCAGCACCTGAACTCCTGGGGGGACCGTCAGTCTTCCTCTTCCCCCCAAAACCCAA

GGACACCCTCATGATCTCCCGGACCCCTGAGGTCACATGCGTGGTGGTGGACGTGAGCCACGAAGACCCTGAGG

TCAAGTTCAACTGGTACGTGGACGGCGTGGAGGTGCATAATGCCAAGACAAAGCCGCGGGAGGAGCAGTACAAC

-continued

AGCACGTACCGTGTGGTCAGCGTCCTCACCGTCCTGCACCAGGACTGGCTGAATGGCAAGGAGTACAAGTGCAA

GGTCTCCAACAAAGCCCTCCCAGCCCCCATCGAGAAAACCATCTCCAAAGCCAAAGGGCAGCCCCGAGAACCAC

AGGTGTACACCCTGCCCCCATCCCGGGATGAGCTGACCAAGAACCAGGTCAGCCTGACCTGCCTGGTCAAAGGC

TTCTATCCCAGCGACATCGCCGTGGAGTGGGAGAGCAATGGGCAGCCGGAGAACAACTACAAGACCACGCCTCC

CGTGCTGGACTCCGACGGCTCCTTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAGAAGAGCCTCTCCCTGTCTCCG

GGTAAA

SEQ ID NO. 106

GACATTGTGATGACACAGTCTCCCTCCTCCCTGGCTGTGTCAGTAGGACAGAAGGTCACTATGAGCTGCAAGTC

CAGTCAGAGCCTTTTAAATGGTAGCAATCAAAAGAACTACTTGGCCTGGTACCAGCAGAAACCAGGACAGTCTC

CTAAACTTCTGGTATACTTTGCATCCACTAGGGATTCTGGGGTCCCTGATCGCTTCATAGGCAGTGGATCTGGG

ACAGATTTCACTCTTACCATCAGCAGTGTGCAGGCTGAAGACCTGGCAGATTACTTCTGTCTGCAACATTTTGG

CACTCCTCCGACGTTCGGTGGAGGCACCAAACTGGAAATCAAACGGACCGTGGCTGCACCATCTGTCTTCATCT

TCCCGCCATCTGATGAGCAGTTGAAATCTGGAACTGCCTCTGTTGTGTGCCTGCTGAATAACTTCTATCCCAGA

GAGGCCAAAGTACAGTGGAAGGTGGATAACGCCCTCCAATCGGGTAACTCCCAGGAGAGTGTCACAGAGCAGGA

CAGCAAGGACAGCACCTACAGCCTCAGCAGCACCCTGACGCTGAGCAAAGCAGACTACGAGAAACACAAAGTCT

ACGCCTGCGAAGTCACCCATCAGGGCCTGAGTTCGCCCGTCACAAAGAGCTTCAACAGGGGAGAGTGT

SEQ ID NO. 107

CTCCAGCCAGGGGCTGAGGTCCCGGTGGTGTGGGCCCAGGAGGGGGCTCCTGCCCAGCTCCCCTGCAGCCCCAC

AATCCCCCTCCAGGATCTCAGCCTTCTGCGAAGAGCAGGGGTCACTTGGCAGCATCAGCCAGACAGTGGCCCGC

CCGCTGCCGCCCCCGGCCATCCCCTGGCCCCCGGCCCTCACCCGGCGGCGCCCTCCTCCTGGGGGCCCAGGCCC

CGCCGCTACACGGTGCTGAGCGTGGGTCCCGGAGGCCTGCGCAGCGGGAGGCTGCCCCTGCAGCCCCGCGTCCA

GCTGGATGAGCGCGGCCGGCAGCGCGGGGACTTCTCGCTATGGCTGCGCCCAGCCCGGCGCGCGGACGCCGGCG

AGTACCGCGCCGCGGTGCACCTCAGGGACCGCGCCCTCTCCTGCCGCCTCCGTCTGCGCCTGGGCCAGGCCTCG

ATGACTGCCAGCCCCCCAGGATCTCTCAGAGCCTCCGACTGGGTCATTTTGAACTGCTCCTTCAGCCGCCCTGA

CCGCCCAGCCTCTGTGCATTGGTTCCGGAACCGGGGCCAGGGCCGAGTCCCTGTCCGGGAGTCCCCCCATCACC

ACTTAGCGGAAAGCTTCCTCTTCCTGCCCCAAGTCAGCCCCATGGACTCTGGGCCCTGGGGCTGCATCCTCACC

TACAGAGATGGCTTCAACGTCTCCATCATGTATAACCTCACTGTTCTGGGTCTGGAGCCCCCAACTCCCTTGAC

AGTGTACGCTGGAGCAGGTTCCAGGGTGGGGCTGCCCTGCCGCCTGCCTGCTGGTGTGGGGACCCGGTCTTTCC

TCACTGCCAAGTGGACTCCTCCTGGGGGAGGCCCTGACCTCCTGGTGACTGGAGACAATGGCGACTTTACCCTT

CGACTAGAGGATGTGAGCCAGGCCCAGGCTGGGACCTACACCTGCCATATCCATCTGCAGGAACAGCAGCTCAA

TGCCACTGTCACATTGGCAATCATCACAGTGACTCCCAAATCCTTTGGGTCACCTGGATCCCTGGGGAAGCTGC

TTTGTGAGGTGACTCCAGTATCTGGACAAGAACGCTTTGTGTGGAGCTCTCTGGACACCCCATCCCAGAGGAGT

TTCTCAGGACCTTGGCTGGAGGCACAGGAGGCCCAGCTCCTTTCCCAGCCTTGGCAATGCCAGCTGTACCAGGG

GGAGAGGCTTCTTGGAGCAGCAGTGTACTTCACAGAGCTGTCTAGCCCACACCACCATCATCACCAT

SEQ ID NO. 108

CCCCAGCCAGGGGCTGAGATCTCGGTGGTGTGGGCCCAGGAGGGGGCTCCTGCCCAGCTCCCCTGCAGCCCCAC

AATCCCCCTCCAGGATCTCAGCCTTCTGCGAAGAGCAGGGGTCACTTGGCAGCATCAACCAGACAGTGGCCCGC

CCGCTCCCGCCCCCGGCCACCCCCCGGCCCCCGGCCATCGCCCGGCGGCGCCCTACTCTTGGGGGCCCAGGCCC

CGCCGCTACACAGTGCTGAGCGTGGGTCCTGGAGGCCTGCGCAGCGGGAGGCTGCCCCTGCAGCCCCGCGTCCA

GCTGGATGAGCGCGGCCGGCAGCGCGGGGACTTCTCGCTGTGGCTGCGCCCAGCCCGGCGCGCGGACGCCGGCG

AGTACCGCGCCACGGTGCACCTCAGGGACCGCGCCCTCTCCTGCCGCCTTCGTCTGCGCGTGGGCCAGGCCTCG

-continued

ATGACTGCCAGCCCCCCAGGGTCTCTCAGGACCTCTGACTGGGTCATTTTGAACTGCTCCTTCAGCCGCCCTGA

CCGCCCAGCCTCTGTGCATTGGTTCCGGAGCCGTGGCCAGGGCCGAGTCCCTGTCCAGGGGTCCCCCCATCACC

ACTTAGCGGAAAGCTTCCTCTTCCTGCCCCATGTCGGCCCCATGGACTCTGGGCTCTGGGGCTGCATCCTCACC

TACAGAGATGGCTTCAATGTCTCCATCATGTATAACCTCACTGTTCTGGGTCTGGAGCCCGCAACTCCCTTGAC

AGTGTACGCTGGAGCAGGTTCCAGGGTGGAGCTGCCCTGCCGCCTGCCTCCTGCTGTGGGGACCCAGTCTTTCC

TTACTGCCAAGTGGGCTCCTCCTGGGGGAGGCCCTGACCTCCTGGTGGCTGGAGACAATGGCGACTTTACCCTT

CGACTAGAGGATGTAAGCCAGGCCCAGGCTGGGACCTACATCTGCCATATCCGTCTACAGGGACAGCAGCTCAA

TGCCACTGTCACATTGGCAATCATCACAGTGACTCCCAAATCCTTTGGGTCACCTGGCTCCCTGGGGAAGCTGC

TTTGTGAGGTGACTCCAGCATCTGGACAAGAACACTTTGTGTGGAGCCCCCTGAACACCCCATCCCAGAGGAGT

TTCTCAGGACCATGGCTGGAGGCCCAGGAAGCCCAGCTCCTTTCCCAGCCTTGGCAATGCCAGCTGCACCAGGG

GGAGAGGCTTCTTGGAGCAGCAGTATACTTCACAGAACTGTCTAGCCCACACCACCATCATCACCAT

SEQ ID NO. 109

CCCCAGCCAGGGGCTGAGATCTCGGTGGTGTGGGCCCAGGAGGGGGCTCCTGCCCAGCTCCCCTGCAGCCCCAC

AATCCCCCTCCAGGATCTCAGCCTTCTGCGAAGAGCAGGGGTCACTTGGCAGCATCAACCAGACAGTGGCCCGC

CCGCTCCCGCCCCCGGCCACCCCCGGCCCCCGGCCATCGCCCGGCGGCGCCCTACTCTTGGGGGCCCAGGCCC

CGCCGCTACACAGTGCTGAGCGTGGGTCCTGGAGGCCTGCGCAGCGGGAGGCTGCCCCTGCAGCCCCGCGTCCA

GCTGGATGAGCGCGGCCGGCAGCGCGGGGACTTCTCGCTGTGGCTGCGCCCAGCCCGGCGCGCGGACGCCGGCG

AGTACCGCGCCACGGTGCACCTCAGGGACCGCGCCCTCTCCTGCCGCCTTCGTCTGCGCGTGGGCCAGGCCTCG

ATGACTGCCAGCCCCCCAGGGTCTCTCAGGACCTCTGACTGGGTCATTTTGAACTGCTCCTTCAGCCGCCCTGA

CCGCCCAGCCTCTGTGCATTGGTTCCGGAGCCGTGGCCAGGGCCAAGTCCCTGTCCAGGAGTCCCCCCATCACC

ACTTAGCGGAAAGCTTCCTCTTCCTGCCCCATGTCGGCCCCATGGACTCTGGGCTCTGGGGCTGCATCCTCACC

TACAGAGATGGCTTCAATGTCTCCATCATGTATAACCTCACTGTTCTGGGTCTGGAGCCCACAACTCCCTTGAC

AGTGTACGCTGGAGCAGGTTCCAGGGTGGAGCTGCCCTGCCGCCTGCCTCCTGCTGTGGGGACCCAGTCTTTCC

TTACTGCCAAGTGGGCTCCTCCTGGGGGAGGCCCTGACCTCCTGGTGGTTGGAGACAATGGCAACTTTACCCTT

CGACTAGAGGATGTAAGCCAGGCCCAGGCTGGGACCTACATCTGCCATATCCGTCTACAGGGACAGCAGCTCAA

TGCCACTGTCACATTGGCAATCATCACAGTGACTCCCAAATCCTTTGGGTCACCTGGCTCCCTGGGGAAGCTGC

TTTGTGAGGTGACTCCAGCATCTGGACAAGAACGCTTTGTGTGGAGCCCCCTGAACACCCCATCCCAGAGGAGT

TTCTCAGGACCGTGGCTGGAGGCCCAGGAAGCCCAGCTCCTTTCCCAGCCTTGGCAATGCCAGCTGCACCAGGG

GGAGAGGCTTCTTGGAGCAGCAGTATACTTCACAGAACTGTCTAGCCCACACCACCATCATCACCAT

SEQ ID NO. 110

ATGGGCTGGAGCTGCATCATCCTGTTCCTGGTGGCCACCGCTACCGGAGTGCACAGC

SEQ ID NO. 111

ATGGAATCACAGACCCAGGTCCTCATGTTTCTTCTGCTCTGGGTATCTGGTGCCTGTGCA

SEQ ID NO. 112

ATGCCGCTGC TGCTACTGCT GCCCCTGCTG TGGGCAGGGG CGCTAGCT

---

The invention claimed is:

1. An antigen binding protein which is capable of binding Lymphocyte Activation Gene 3 (LAG-3) and which comprises CDRL1, CDRL2 and CDRL3 from SEQ ID NO:5 and CDRH1, CDRH2 and CDRH3 from SEQ ID NO:10.

2. The antigen binding protein according to claim 1, wherein the antigen binding protein is capable of binding LAG-3 expressed on activated T-cells.

3. The antigen binding protein according to claim 1, wherein the antigen binding protein comprises a human IgG1 constant region and is capable of depleting LAG-3+ activated human T-cells.

4. The antigen binding protein according to claim 1, wherein the antigen binding protein is a humanised antibody.

5. The humanised antibody according to claim 4, wherein the humanised antibody comprises a human IgG1 constant region.

6. The humanised antibody according to claim 5, which is non-fucosylated.

7. A humanised antibody comprising the variable light chain (VL) of SEQ ID NO:4 and the variable heavy chain (VH) of SEQ ID NO:9, wherein the antibody does not comprise fucose on the core carbohydrate structure attached to Asn297.

8. An antigen binding protein as produced by a host cell that comprises an expression vector that comprises a nucleic acid molecule which encodes an antigen binding protein of claim 1.

9. A method of producing an antigen binding protein, comprising a) culturing a host cell that comprises an expression vector that comprises a nucleic acid molecule which encodes an antigen binding protein of claim 1 under conditions suitable to express the antigen binding protein and b) isolating the antigen binding protein.

10. A pharmaceutical composition comprising a) an antigen binding protein according to claim 1, and b) a pharmaceutically acceptable carrier.

11. The antigen binding protein of claim 8, wherein the FUT8 gene encoding alpha-1,6-fucosyltransferase has been inactivated in the host cell.

* * * * *

SEQUENCE LISTING

<160> NUMBER OF SEQ ID NOS: 112

<210> SEQ ID NO 1
<211> LENGTH: 17
<212> TYPE: PRT
<213> ORGANISM: Artificial
<220> FEATURE:
<223> OTHER INFORMATION: H5L7, CDRL1 (Kabat defined)

-continued

<400> SEQUENCE: 1

Lys Ser Ser Gln Ser Leu Leu Asn Pro Ser Asn Gln Lys Asn Tyr Leu
1               5                   10                  15

Ala

<210> SEQ ID NO 2
<211> LENGTH: 7
<212> TYPE: PRT
<213> ORGANISM: Murine

<400> SEQUENCE: 2

Phe Ala Ser Thr Arg Asp Ser
1               5

<210> SEQ ID NO 3
<211> LENGTH: 9
<212> TYPE: PRT
<213> ORGANISM: Murine

<400> SEQUENCE: 3

Leu Gln His Phe Gly Thr Pro Pro Thr
1               5

<210> SEQ ID NO 4
<211> LENGTH: 114
<212> TYPE: PRT
<213> ORGANISM: Artificial
<220> FEATURE:
<223> OTHER INFORMATION: H5L7, VL

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg

<210> SEQ ID NO 5
<211> LENGTH: 220
<212> TYPE: PRT
<213> ORGANISM: Artificial
<220> FEATURE:
<223> OTHER INFORMATION: H5L7, light chain humanised construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys

-continued

```
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 6
<211> LENGTH: 5
<212> TYPE: PRT
<213> ORGANISM: Murine

<400> SEQUENCE: 6

Ala Tyr Gly Val Asn
1               5


<210> SEQ ID NO 7
<211> LENGTH: 16
<212> TYPE: PRT
<213> ORGANISM: Artificial
<220> FEATURE:
<223> OTHER INFORMATION: H5L7, CDRH2 (Kabat defined)

<400> SEQUENCE: 7

Met Ile Trp Asp Asp Gly Ser Thr Asp Tyr Asp Ser Ala Leu Lys Ser
1               5                   10                  15


<210> SEQ ID NO 8
<211> LENGTH: 8
<212> TYPE: PRT
<213> ORGANISM: Murine

<400> SEQUENCE: 8

Glu Gly Asp Val Ala Phe Asp Tyr
1               5


<210> SEQ ID NO 9
<211> LENGTH: 116
<212> TYPE: PRT
<213> ORGANISM: Artificial
<220> FEATURE:
<223> OTHER INFORMATION: H5L7, VH

<400> SEQUENCE: 9
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ala Tyr
            20                  25                  30

Gly Val Asn Trp Ile Arg Gln Pro Pro Gly Lys Gly Leu Glu Trp Ile
        35                  40                  45

Gly Met Ile Trp Asp Asp Gly Ser Thr Asp Tyr Asp Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser
        115


<210> SEQ ID NO 10
<211> LENGTH: 446
<212> TYPE: PRT
<213> ORGANISM: Artificial
<220> FEATURE:
<223> OTHER INFORMATION: H5L7, heavy chain humanised construct

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ala Tyr
            20                  25                  30

Gly Val Asn Trp Ile Arg Gln Pro Pro Gly Lys Gly Leu Glu Trp Ile
        35                  40                  45

Gly Met Ile Trp Asp Asp Gly Ser Thr Asp Tyr Asp Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 11
<211> LENGTH: 220
<212> TYPE: PRT
<213> ORGANISM: Artificial
<220> FEATURE:
<223> OTHER INFORMATION: H1L7, light chain humanised construct

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 12
<211> LENGTH: 446
<212> TYPE: PRT
<213> ORGANISM: Artificial
<220> FEATURE:
<223> OTHER INFORMATION: H1L7, heavy chain humanised construct

<400> SEQUENCE: 12

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Leu Thr Ala Tyr
20 25 30

Gly Val Asn Trp Ile Arg Gln Pro Pro Gly Lys Gly Leu Glu Trp Ile
35 40 45

Gly Met Ile Trp Asp Asp Gly Ser Thr Asp Tyr Asn Ser Ala Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Gly Asp Val Ala Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 13
<211> LENGTH: 220
<212> TYPE: PRT
<213> ORGANISM: Artificial
<220> FEATURE:
<223> OTHER INFORMATION: J7L7, light chain humanised construct

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 14
<211> LENGTH: 446
<212> TYPE: PRT
<213> ORGANISM: Artificial
<220> FEATURE:
<223> OTHER INFORMATION: J7L7, heavy chain humanised construct

<400> SEQUENCE: 14

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Ala Tyr
            20                  25                  30

Gly Val Asn Trp Val Arg Gln Ala Pro Gly Gln Gly Leu Glu Trp Met
        35                  40                  45

Gly Met Ile Trp Asp Asp Gly Ser Thr Asp Tyr Asn Ser Ala Leu Lys
    50                  55                  60

Ser Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

-continued

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 15
<211> LENGTH: 220
<212> TYPE: PRT
<213> ORGANISM: Artificial
<220> FEATURE:
<223> OTHER INFORMATION: H4L7, light chain humanised construct

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 16
<211> LENGTH: 446
<212> TYPE: PRT
<213> ORGANISM: Artificial
<220> FEATURE:
<223> OTHER INFORMATION: H4L7, heavy chain humanised construct

<400> SEQUENCE: 16

Gln Val Gln Leu Gln Glu Ser Gly Pro Gly Leu Val Lys Pro Ser Glu

-continued

```
1               5                   10                  15

Thr Leu Ser Leu Thr Cys Thr Val Ser Gly Phe Ser Leu Thr Ala Tyr
            20                  25                  30

Gly Val Asn Trp Ile Arg Gln Pro Pro Gly Lys Gly Leu Glu Trp Leu
        35                  40                  45

Gly Met Ile Trp Asp Asp Gly Ser Thr Asp Tyr Asn Ser Ala Leu Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly Lys
        435                 440                 445


<210> SEQ ID NO 17
<211> LENGTH: 220
<212> TYPE: PRT
<213> ORGANISM: Artificial
<220> FEATURE:
<223> OTHER INFORMATION: J11L7, light chain humanised construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 18
<211> LENGTH: 446
<212> TYPE: PRT
<213> ORGANISM: Artificial
<220> FEATURE:
<223> OTHER INFORMATION: J11L7, heavy chain humanised construct

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Ala Tyr
            20                  25                  30

Gly Val Asn Trp Val Arg Gln Ala Pro Gly Gln Gly Leu Glu Trp Met
        35                  40                  45

Gly Met Ile Trp Asp Asp Gly Ser Thr Asp Tyr Asp Ser Ala Leu Lys
    50                  55                  60

Ser Arg Val Thr Ile Thr Ala Asp Lys Ser Thr Ser Thr Ala Tyr Met
```

```
65                  70                  75                  80

Glu Leu Ser Ser Leu Arg Ser Glu Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 19
<211> LENGTH: 220
<212> TYPE: PRT
<213> ORGANISM: Artificial
<220> FEATURE:
<223> OTHER INFORMATION: H2L7, light chain humanised construct

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 20
<211> LENGTH: 446
<212> TYPE: PRT
<213> ORGANISM: Artificial
<220> FEATURE:
<223> OTHER INFORMATION: H2L7, heavy chain humanised construct

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ala Tyr
            20                  25                  30

Gly Val Asn Trp Ile Arg Gln Pro Pro Gly Lys Gly Leu Glu Trp Ile
        35                  40                  45

Gly Met Ile Trp Asp Asp Gly Ser Thr Asp Tyr Asn Ser Ala Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu

```
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 21
<211> LENGTH: 220
<212> TYPE: PRT
<213> ORGANISM: Artificial
<220> FEATURE:
<223> OTHER INFORMATION: J13L7, light chain humanised construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
```

```
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 22
<211> LENGTH: 446
<212> TYPE: PRT
<213> ORGANISM: Artificial
<220> FEATURE:
<223> OTHER INFORMATION: J13L7, heavy chain humanised construct

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Gly Val Asn Trp Val Arg Gln Ala Pro Gly Gln Gly Leu Glu Trp Met
        35                  40                  45

Gly Met Ile Trp Asp Asp Gly Ser Thr Asp Tyr Asp Ser Ala Leu Lys
    50                  55                  60

Ser Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 23
<211> LENGTH: 220
<212> TYPE: PRT
<213> ORGANISM: Artificial
<220> FEATURE:
<223> OTHER INFORMATION: H7L7, light chain humanised construct

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
```

```
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 24
<211> LENGTH: 446
<212> TYPE: PRT
<213> ORGANISM: Artificial
<220> FEATURE:
<223> OTHER INFORMATION: H7L7, heavy chain humanised construct

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Tyr
            20                  25                  30

Gly Val Asn Trp Ile Arg Gln Pro Pro Gly Lys Gly Leu Glu Trp Ile
        35                  40                  45

Gly Met Ile Trp Asp Asp Gly Ser Thr Asp Tyr Asp Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 25
<211> LENGTH: 220
<212> TYPE: PRT
<213> ORGANISM: Artificial
<220> FEATURE:
<223> OTHER INFORMATION: J0L7, light chain humanised construct

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
```

```
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 26
<211> LENGTH: 446
<212> TYPE: PRT
<213> ORGANISM: Artificial
<220> FEATURE:
<223> OTHER INFORMATION: J0L7, heavy chain humanised construct

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Gly Val Asn Trp Val Arg Gln Ala Pro Gly Gln Gly Leu Glu Trp Met
        35                  40                  45

Gly Met Ile Trp Asp Asp Gly Ser Thr Asp Tyr Asn Ser Ala Leu Lys
    50                  55                  60

Ser Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 27
<211> LENGTH: 220
<212> TYPE: PRT
<213> ORGANISM: Artificial
<220> FEATURE:
<223> OTHER INFORMATION: H0L7, light chain humanised construct

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Pro
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 28
<211> LENGTH: 446
<212> TYPE: PRT
```

<213> ORGANISM: Artificial
<220> FEATURE:
<223> OTHER INFORMATION: H0L7, heavy chain humanised construct

<400> SEQUENCE: 28

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Tyr
            20                  25                  30

Gly Val Asn Trp Ile Arg Gln Pro Pro Gly Lys Gly Leu Glu Trp Ile
        35                  40                  45

Gly Met Ile Trp Asp Asp Gly Ser Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
```

-continued

```
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 29
<211> LENGTH: 220
<212> TYPE: PRT
<213> ORGANISM: Artificial
<220> FEATURE:
<223> OTHER INFORMATION: H1L1, light chain humanised construct

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Gly
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 30
<211> LENGTH: 446
<212> TYPE: PRT
<213> ORGANISM: Artificial
<220> FEATURE:
<223> OTHER INFORMATION: H1L1, heavy chain humanised construct

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ala Tyr
            20                  25                  30
```

-continued

```
Gly Val Asn Trp Ile Arg Gln Pro Pro Gly Lys Gly Leu Glu Trp Ile
        35                  40                  45

Gly Met Ile Trp Asp Asp Gly Ser Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

-continued

<210> SEQ ID NO 31
<211> LENGTH: 220
<212> TYPE: PRT
<213> ORGANISM: Artificial
<220> FEATURE:
<223> OTHER INFORMATION: H5L1, light chain humanised construct

<400> SEQUENCE: 31

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Asn Gly
20 25 30

Ser Asn Gln Lys Asn Tyr Leu Ala Trp Tyr Gln Gln Lys Pro Gly Lys
35 40 45

Ala Pro Lys Leu Leu Val Tyr Phe Ala Ser Thr Arg Asp Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Leu Gln
85 90 95

His Phe Gly Thr Pro Pro Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 32
<211> LENGTH: 446
<212> TYPE: PRT
<213> ORGANISM: Artificial
<220> FEATURE:
<223> OTHER INFORMATION: H5L1, heavy chain humanised construct

<400> SEQUENCE: 32

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Leu Thr Ala Tyr
20 25 30

Gly Val Asn Trp Ile Arg Gln Pro Pro Gly Lys Gly Leu Glu Trp Ile
35 40 45

Gly Met Ile Trp Asp Asp Gly Ser Thr Asp Tyr Asp Ser Ala Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

-continued

```
Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 33
<211> LENGTH: 220
<212> TYPE: PRT
<213> ORGANISM: Artificial
<220> FEATURE:
<223> OTHER INFORMATION: J7L1, light chain humanised construct

<400> SEQUENCE: 33

Asp Ile Gln Met Thr Gln Ser Pro Ser Ser Leu Ser Ala Ser Val Gly
1               5                   10                  15
```

```
Asp Arg Val Thr Ile Thr Cys Lys Ser Ser Gln Ser Leu Leu Asn Gly
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 34
<211> LENGTH: 446
<212> TYPE: PRT
<213> ORGANISM: Artificial
<220> FEATURE:
<223> OTHER INFORMATION: J7L1, heavy chain humanised construct

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Ala Tyr
            20                  25                  30

Gly Val Asn Trp Val Arg Gln Ala Pro Gly Gln Gly Leu Glu Trp Met
        35                  40                  45

Gly Met Ile Trp Asp Asp Gly Ser Thr Asp Tyr Asn Ser Ala Leu Lys
    50                  55                  60

Ser Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

-continued

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 35
<211> LENGTH: 220
<212> TYPE: PRT
<213> ORGANISM: Artificial
<220> FEATURE:
<223> OTHER INFORMATION: J11L1, light chain humanised construct

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Gly
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80
```

-continued

```
Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 36
<211> LENGTH: 446
<212> TYPE: PRT
<213> ORGANISM: Artificial
<220> FEATURE:
<223> OTHER INFORMATION: J11L1, heavy chain humanised construct

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Ala Tyr
            20                  25                  30

Gly Val Asn Trp Val Arg Gln Ala Pro Gly Gln Gly Leu Glu Trp Met
        35                  40                  45

Gly Met Ile Trp Asp Asp Gly Ser Thr Asp Tyr Asp Ser Ala Leu Lys
    50                  55                  60

Ser Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

-continued

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 37
<211> LENGTH: 220
<212> TYPE: PRT
<213> ORGANISM: Artificial
<220> FEATURE:
<223> OTHER INFORMATION: J13L1, light chain humanised construct

<400> SEQUENCE: 37

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Asn Gly
20 25 30

Ser Asn Gln Lys Asn Tyr Leu Ala Trp Tyr Gln Gln Lys Pro Gly Lys
35 40 45

Ala Pro Lys Leu Leu Val Tyr Phe Ala Ser Thr Arg Asp Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Leu Gln
85 90 95

His Phe Gly Thr Pro Pro Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

-continued

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 38
<211> LENGTH: 446
<212> TYPE: PRT
<213> ORGANISM: Artificial
<220> FEATURE:
<223> OTHER INFORMATION: J13L1, heavy chain humanised construct

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Gly Val Asn Trp Val Arg Gln Ala Pro Gly Gln Gly Leu Glu Trp Met
        35                  40                  45

Gly Met Ile Trp Asp Asp Gly Ser Thr Asp Tyr Asp Ser Ala Leu Lys
    50                  55                  60

Ser Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

```
Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 39
<211> LENGTH: 220
<212> TYPE: PRT
<213> ORGANISM: Artificial
<220> FEATURE:
<223> OTHER INFORMATION: H7L1, light chain humanised construct

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Gly
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205
```

```
Ser Pro Val Thr Lys Ser Phe Asn Arg Gly Glu Cys
    210                 215                 220


<210> SEQ ID NO 40
<211> LENGTH: 446
<212> TYPE: PRT
<213> ORGANISM: Artificial
<220> FEATURE:
<223> OTHER INFORMATION: H7L1, heavy chain humanised construct

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Tyr
            20                  25                  30

Gly Val Asn Trp Ile Arg Gln Pro Pro Gly Lys Gly Leu Glu Trp Ile
        35                  40                  45

Gly Met Ile Trp Asp Asp Gly Ser Thr Asp Tyr Asp Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350
```

```
Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 41
<211> LENGTH: 220
<212> TYPE: PRT
<213> ORGANISM: Artificial
<220> FEATURE:
<223> OTHER INFORMATION: J0L1, light chain humanised construct

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Gly
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 42
<211> LENGTH: 446
<212> TYPE: PRT
<213> ORGANISM: Artificial
<220> FEATURE:
<223> OTHER INFORMATION: J0L1, heavy chain humanised construct

<400> SEQUENCE: 42
```

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Gly Val Asn Trp Val Arg Gln Ala Pro Gly Gln Gly Leu Glu Trp Met
        35                  40                  45

Gly Met Ile Trp Asp Asp Gly Ser Thr Asp Tyr Asn Ser Ala Leu Lys
    50                  55                  60

Ser Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

```
Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 43
<211> LENGTH: 220
<212> TYPE: PRT
<213> ORGANISM: Artificial
<220> FEATURE:
<223> OTHER INFORMATION: H0L1, light chain humanised construct

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Gly
            20                  25                  30

Ser Asn Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Leu Gln
                85                  90                  95

His Phe Gly Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 44
<211> LENGTH: 446
<212> TYPE: PRT
<213> ORGANISM: Artificial
<220> FEATURE:
<223> OTHER INFORMATION: H0L1, heavy chain humanised construct

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Tyr
            20                  25                  30

Gly Val Asn Trp Ile Arg Gln Pro Pro Gly Lys Gly Leu Glu Trp Ile
        35                  40                  45

Gly Met Ile Trp Asp Asp Gly Ser Thr Asp Tyr Asn Ser Ala Leu Lys
    50                  55                  60
```

-continued

```
Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asp Val Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 45
<211> LENGTH: 106
<212> TYPE: PRT
<213> ORGANISM: Human

<400> SEQUENCE: 45

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 46
<211> LENGTH: 330
<212> TYPE: PRT
<213> ORGANISM: Human

<400> SEQUENCE: 46

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 47
<211> LENGTH: 116
<212> TYPE: PRT
<213> ORGANISM: Murine

<400> SEQUENCE: 47

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asn Trp Val Arg Gln Pro Pro Gly Lys Gly Leu Glu Trp Leu
        35                  40                  45

Gly Met Ile Trp Asp Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Glu Gly Asp Val Ala Phe Asp Tyr Trp Gly Gln Gly Thr Thr Leu
            100                 105                 110

Thr Val Ser Ser
        115


<210> SEQ ID NO 48
<211> LENGTH: 114
<212> TYPE: PRT
<213> ORGANISM: Murine

<400> SEQUENCE: 48

Asp Ile Val Met Thr Gln Ser Pro Ser Ser Leu Ala Val Ser Val Gly
1               5                   10                  15

Gln Lys Val Thr Met Ser Cys Lys Ser Ser Gln Ser Leu Leu Asn Gly
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Leu Gln
                85                  90                  95

His Phe Gly Thr Pro Pro Thr Phe Gly Gly Gly Thr Lys Leu Glu Ile
            100                 105                 110

Lys Arg
```

<210> SEQ ID NO 49
<211> LENGTH: 446
<212> TYPE: PRT
<213> ORGANISM: Artificial
<220> FEATURE:
<223> OTHER INFORMATION: IMP731, heavy chain sequence

<400> SEQUENCE: 49

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asn Trp Val Arg Gln Pro Pro Gly Lys Gly Leu Glu Trp Leu
        35                  40                  45

Gly Met Ile Trp Asp Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Glu Gly Asp Val Ala Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 50
<211> LENGTH: 220
<212> TYPE: PRT
<213> ORGANISM: Artificial
<220> FEATURE:
<223> OTHER INFORMATION: IMP731, light chain sequence

<400> SEQUENCE: 50

Asp Ile Val Met Thr Gln Ser Pro Ser Ser Leu Ala Val Ser Val Gly
1               5                   10                  15

Gln Lys Val Thr Met Ser Cys Lys Ser Ser Gln Ser Leu Leu Asn Gly
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Leu Gln
                85                  90                  95

His Phe Gly Thr Pro Pro Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 51
<211> LENGTH: 417
<212> TYPE: PRT
<213> ORGANISM: Artificial
<220> FEATURE:
<223> OTHER INFORMATION: Recombinant human LAG-3-ECD-His6

<400> SEQUENCE: 51

Leu Gln Pro Gly Ala Glu Val Pro Val Val Trp Ala Gln Glu Gly Ala
1               5                   10                  15
```

```
Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro His His His His His
                405                 410                 415

His

<210> SEQ ID NO 52
```

<211> LENGTH: 417
<212> TYPE: PRT
<213> ORGANISM: Artificial
<220> FEATURE:
<223> OTHER INFORMATION: Recombinant cynomolgus macaque LAG-3 ECD-His6

<400> SEQUENCE: 52

Pro Gln Pro Gly Ala Glu Ile Ser Val Val Trp Ala Gln Glu Gly Ala
1 5 10 15

Pro Ala Gln Leu Pro Cys Ser Pro Thr Ile Pro Leu Gln Asp Leu Ser
20 25 30

Leu Leu Arg Arg Ala Gly Val Thr Trp Gln His Gln Pro Asp Ser Gly
35 40 45

Pro Pro Ala Pro Ala Pro Gly His Pro Pro Ala Pro Gly His Arg Pro
50 55 60

Ala Ala Pro Tyr Ser Trp Gly Pro Arg Pro Arg Arg Tyr Thr Val Leu
65 70 75 80

Ser Val Gly Pro Gly Gly Leu Arg Ser Gly Arg Leu Pro Leu Gln Pro
85 90 95

Arg Val Gln Leu Asp Glu Arg Gly Arg Gln Arg Gly Asp Phe Ser Leu
100 105 110

Trp Leu Arg Pro Ala Arg Arg Ala Asp Ala Gly Glu Tyr Arg Ala Thr
115 120 125

Val His Leu Arg Asp Arg Ala Leu Ser Cys Arg Leu Arg Leu Arg Val
130 135 140

Gly Gln Ala Ser Met Thr Ala Ser Pro Pro Gly Ser Leu Arg Thr Ser
145 150 155 160

Asp Trp Val Ile Leu Asn Cys Ser Phe Ser Arg Pro Asp Arg Pro Ala
165 170 175

Ser Val His Trp Phe Arg Ser Arg Gly Gln Gly Arg Val Pro Val Gln
180 185 190

Gly Ser Pro His His His Leu Ala Glu Ser Phe Leu Phe Leu Pro His
195 200 205

Val Gly Pro Met Asp Ser Gly Leu Trp Gly Cys Ile Leu Thr Tyr Arg
210 215 220

Asp Gly Phe Asn Val Ser Ile Met Tyr Asn Leu Thr Val Leu Gly Leu
225 230 235 240

Glu Pro Ala Thr Pro Leu Thr Val Tyr Ala Gly Ala Gly Ser Arg Val
245 250 255

Glu Leu Pro Cys Arg Leu Pro Pro Ala Val Gly Thr Gln Ser Phe Leu
260 265 270

Thr Ala Lys Trp Ala Pro Pro Gly Gly Gly Pro Asp Leu Leu Val Ala
275 280 285

Gly Asp Asn Gly Asp Phe Thr Leu Arg Leu Glu Asp Val Ser Gln Ala
290 295 300

Gln Ala Gly Thr Tyr Ile Cys His Ile Arg Leu Gln Gly Gln Gln Leu
305 310 315 320

Asn Ala Thr Val Thr Leu Ala Ile Ile Thr Val Thr Pro Lys Ser Phe
325 330 335

Gly Ser Pro Gly Ser Leu Gly Lys Leu Leu Cys Glu Val Thr Pro Ala
340 345 350

Ser Gly Gln Glu His Phe Val Trp Ser Pro Leu Asn Thr Pro Ser Gln
355 360 365

Arg Ser Phe Ser Gly Pro Trp Leu Glu Ala Gln Glu Ala Gln Leu Leu
370 375 380

```
Ser Gln Pro Trp Gln Cys Gln Leu His Gln Gly Glu Arg Leu Leu Gly
385                 390                 395                 400

Ala Ala Val Tyr Phe Thr Glu Leu Ser Ser Pro His His His His His
                405                 410                 415

His


<210> SEQ ID NO 53
<211> LENGTH: 417
<212> TYPE: PRT
<213> ORGANISM: Artificial
<220> FEATURE:
<223> OTHER INFORMATION: Recombinant baboon LAG-3 ECD-His6

<400> SEQUENCE: 53

Pro Gln Pro Gly Ala Glu Ile Ser Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Pro Ala Pro Gly His Pro Pro Ala Pro Gly His Arg Pro
    50                  55                  60

Ala Ala Pro Tyr Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Thr
        115                 120                 125

Val His Leu Arg Asp Arg Ala Leu Ser Cys Arg Leu Arg Leu Arg Val
    130                 135                 140

Gly Gln Ala Ser Met Thr Ala Ser Pro Pro Gly Ser Leu Arg Thr Ser
145                 150                 155                 160

Asp Trp Val Ile Leu Asn Cys Ser Phe Ser Arg Pro Asp Arg Pro Ala
                165                 170                 175

Ser Val His Trp Phe Arg Ser Arg Gly Gln Gly Gln Val Pro Val Gln
            180                 185                 190

Glu Ser Pro His His His Leu Ala Glu Ser Phe Leu Phe Leu Pro His
        195                 200                 205

Val Gly Pro Met Asp Ser Gly Leu Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Thr Thr Pro Leu Thr Val Tyr Ala Gly Ala Gly Ser Arg Val
                245                 250                 255

Glu Leu Pro Cys Arg Leu Pro Pro Ala Val Gly Thr Gln Ser Phe Leu
            260                 265                 270

Thr Ala Lys Trp Ala Pro Pro Gly Gly Gly Pro Asp Leu Leu Val Val
        275                 280                 285

Gly Asp Asn Gly Asn Phe Thr Leu Arg Leu Glu Asp Val Ser Gln Ala
    290                 295                 300

Gln Ala Gly Thr Tyr Ile Cys His Ile Arg Leu Gln Gly Gln Gln Leu
305                 310                 315                 320
```

-continued

```
Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Ala
            340                 345                 350

Ser Gly Gln Glu Arg Phe Val Trp Ser Pro Leu Asn Thr Pro Ser Gln
        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu His Gln Gly Glu Arg Leu Leu Gly
385                 390                 395                 400

Ala Ala Val Tyr Phe Thr Glu Leu Ser Ser Pro His His His His His
                405                 410                 415

His


<210> SEQ ID NO 54
<211> LENGTH: 19
<212> TYPE: PRT
<213> ORGANISM: Murine

<400> SEQUENCE: 54

Met Gly Trp Ser Cys Ile Ile Leu Phe Leu Val Ala Thr Ala Thr Gly
1               5                   10                  15

Val His Ser


<210> SEQ ID NO 55
<211> LENGTH: 20
<212> TYPE: PRT
<213> ORGANISM: Murine

<400> SEQUENCE: 55

Met Glu Ser Gln Thr Gln Val Leu Met Phe Leu Leu Leu Trp Val Ser
1               5                   10                  15

Gly Ala Cys Ala
            20


<210> SEQ ID NO 56
<211> LENGTH: 16
<212> TYPE: PRT
<213> ORGANISM: Human

<400> SEQUENCE: 56

Met Pro Leu Leu Leu Leu Leu Pro Leu Leu Trp Ala Gly Ala Leu Ala
1               5                   10                  15


<210> SEQ ID NO 57
<211> LENGTH: 51
<212> TYPE: DNA
<213> ORGANISM: Artificial
<220> FEATURE:
<223> OTHER INFORMATION: H5L7, CDRL1 (Kabat defined)

<400> SEQUENCE: 57

aagagcagcc agagcctgct gaaccccagc aaccagaaga actacctggc c              51


<210> SEQ ID NO 58
<211> LENGTH: 21
<212> TYPE: DNA
<213> ORGANISM: Murine

<400> SEQUENCE: 58

ttcgcctcta ccagggattc c                                               21
```

<210> SEQ ID NO 59
<211> LENGTH: 27
<212> TYPE: DNA
<213> ORGANISM: Murine

<400> SEQUENCE: 59
ctgcagcact tcggcacccc tcccact 27

<210> SEQ ID NO 60
<211> LENGTH: 342
<212> TYPE: DNA
<213> ORGANISM: Artificial
<220> FEATURE:
<223> OTHER INFORMATION: H5L7, VL

<400> SEQUENCE: 60
gacatccaga tgacccagag cccctctagc ctcagcgcca gcgtgggcga cagggtgacc 60
atcacctgca agagcagcca gagcctgctg aaccccagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gt 342

<210> SEQ ID NO 61
<211> LENGTH: 660
<212> TYPE: DNA
<213> ORGANISM: Artificial
<220> FEATURE:
<223> OTHER INFORMATION: H5L7, light chain humanised construct

<400> SEQUENCE: 61
gacatccaga tgacccagag cccctctagc ctcagcgcca gcgtgggcga cagggtgacc 60
atcacctgca agagcagcca gagcctgctg aaccccagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 62
<211> LENGTH: 15
<212> TYPE: DNA
<213> ORGANISM: Murine

<400> SEQUENCE: 62
gcctacggcg tcaac 15

<210> SEQ ID NO 63
<211> LENGTH: 48
<212> TYPE: DNA

<213> ORGANISM: Artificial
<220> FEATURE:
<223> OTHER INFORMATION: H5L7, CDRH2 (Kabat defined)

<400> SEQUENCE: 63
atgatctggg acgacggcag caccgactac gacagcgccc tgaagagc 48

<210> SEQ ID NO 64
<211> LENGTH: 24
<212> TYPE: DNA
<213> ORGANISM: Murine

<400> SEQUENCE: 64
gagggcgacg tggccttcga ttac 24

<210> SEQ ID NO 65
<211> LENGTH: 348
<212> TYPE: DNA
<213> ORGANISM: Artificial
<220> FEATURE:
<223> OTHER INFORMATION: H5L7, VH

<400> SEQUENCE: 65
caggtgcagc tccaggagag cggccccggc ctggtgaagc ctagcgagac cctgagcctg 60
acctgcaccg tgagcggctt ctccctgacc gcctacggcg tcaactggat caggcagccc 120
cccggcaaag gcctggagtg gattgggatg atctgggacg acggcagcac cgactacgac 180
agcgccctga agagcagggt gaccatcagc gtggacacca gcaagaacca gttcagcctg 240
aagctgagca gcgtgactgc cgccgacacc gccgtctatt actgcgccag ggagggcgac 300
gtggccttcg attactgggg ccagggcaca ctagtgaccg tgtccagc 348

<210> SEQ ID NO 66
<211> LENGTH: 1338
<212> TYPE: DNA
<213> ORGANISM: Artificial
<220> FEATURE:
<223> OTHER INFORMATION: H5L7, heavy chain humanised construct

<400> SEQUENCE: 66
caggtgcagc tccaggagag cggccccggc ctggtgaagc ctagcgagac cctgagcctg 60
acctgcaccg tgagcggctt ctccctgacc gcctacggcg tcaactggat caggcagccc 120
cccggcaaag gcctggagtg gattgggatg atctgggacg acggcagcac cgactacgac 180
agcgccctga agagcagggt gaccatcagc gtggacacca gcaagaacca gttcagcctg 240
aagctgagca gcgtgactgc cgccgacacc gccgtctatt actgcgccag ggagggcgac 300
gtggccttcg attactgggg ccagggcaca ctagtgaccg tgtccagcgc cagcaccaag 360
ggccccagcg tgttccccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900

-continued gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg cccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 67
<211> LENGTH: 660
<212> TYPE: DNA
<213> ORGANISM: Artificial
<220> FEATURE:
<223> OTHER INFORMATION: H1L7, light chain humanised construct

<400> SEQUENCE: 67
gacatccaga tgacccagag cccctctagc ctcagcgcca gcgtgggcga cagggtgacc 60
atcacctgca agagcagcca gagcctgctg aaccccagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tcccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 68
<211> LENGTH: 1338
<212> TYPE: DNA
<213> ORGANISM: Artificial
<220> FEATURE:
<223> OTHER INFORMATION: H1L7, heavy chain humanised construct

<400> SEQUENCE: 68
caggtgcagc tccaggagag cggccccggc ctggtgaagc ctagcgagac cctgagcctg 60
acctgcaccg tgagcggctt ctccctgacc gcctacggcg tcaactggat caggcagccc 120
cccggcaaag gcctggagtg gattgggatg atctgggacg acggcagcac cgactacaac 180
agcgccctga agagcagggt gaccatcagc gtggacacca gcaagaacca gttcagcctg 240
aagctgagca gcgtgactgc cgccgacacc gccgtctatt actgcgccag ggagggcgac 300
gtggccttcg attactgggg ccagggcaca ctagtgaccg tgtccagcgc cagcaccaag 360
ggccccagcg tgttcccccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg ccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 69
<211> LENGTH: 660
<212> TYPE: DNA
<213> ORGANISM: Artificial
<220> FEATURE:
<223> OTHER INFORMATION: J7L7, light chain humanised construct

<400> SEQUENCE: 69
gacatccaga tgacccagag cccctctagc ctcagcgcca gcgtgggcga cagggtgacc 60
atcacctgca agagcagcca gagcctgctg aaccccagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tcccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 70
<211> LENGTH: 1338
<212> TYPE: DNA
<213> ORGANISM: Artificial
<220> FEATURE:
<223> OTHER INFORMATION: J7L7, heavy chain humanised construct

<400> SEQUENCE: 70
caggtgcagc tcgtgcagag cggggccgaa gtcaagaaac ccggcagctc cgtgaaggtg 60
agctgcaagg ccagcggctt ctctctcact gcctacggcg tgaactgggt gaggcaggct 120
cccggccagg gcctggagtg gatgggcatg atctgggacg acggcagcac cgactacaac 180
agcgccctga agagcagggt gaccatcacc gccgacaaga gcaccagcac cgcctacatg 240
gaactgagca gcctgaggag cgaggacacc gccgtgtact attgcgccag ggagggcgac 300
gtggccttcg attactgggg ccagggcaca ctagtgaccg tgtccagcgc cagcaccaag 360

-continued

```
ggccccagcg tgttcccct ggcccccagc agcaagagca ccagcggcgg cacagccgcc    420

ctgggctgcc tggtgaagga ctacttcccc gaaccggtga ccgtgtcctg gaacagcgga    480

gccctgacca gcggcgtgca caccttcccc gccgtgctgc agagcagcgg cctgtacagc    540

ctgagcagcg tggtgaccgt gcccagcagc agcctgggca cccagaccta catctgtaac    600

gtgaaccaca agcccagcaa caccaaggtg gacaagaagg tggagcccaa gagctgtgac    660

aagacccaca cctgcccccc ctgccctgcc cccgagctgc tgggaggccc cagcgtgttc    720

ctgttccccc ccaagcctaa ggacaccctg atgatcagca gaacccccga ggtgacctgt    780

gtggtggtgg atgtgagcca cgaggaccct gaggtgaagt tcaactggta cgtggacggc    840

gtggaggtgc acaatgccaa gaccaagccc agggaggagc agtacaacag cacctaccgg    900

gtggtgtccg tgctgaccgt gctgcaccag gattggctga acggcaagga gtacaagtgt    960

aaggtgtcca acaaggccct gcctgcccct atcgagaaaa ccatcagcaa ggccaagggc   1020

cagcccagag agccccaggt gtacaccctg cccccctagca gagatgagct gaccaagaac   1080

caggtgtccc tgacctgcct ggtgaagggc ttctacccca gcgacatcgc cgtggagtgg   1140

gagagcaacg gccagcccga gaacaactac aagaccaccc cccctgtgct ggacagcgat   1200

ggcagcttct tcctgtacag caagctgacc gtggacaaga gcagatggca gcagggcaac   1260

gtgttcagct gctccgtgat gcacgaggcc ctgcacaatc actacaccca gaagagcctg   1320

agcctgtccc ctggcaag                                                 1338
```

<210> SEQ ID NO 71
<211> LENGTH: 660
<212> TYPE: DNA
<213> ORGANISM: Artificial
<220> FEATURE:
<223> OTHER INFORMATION: H4L7, light chain humanised construct

<400> SEQUENCE: 71

```
gacatccaga tgacccagag cccctctagc ctcagcgcca gcgtgggcga cagggtgacc     60

atcacctgca agagcagcca gagcctgctg aaccccagca accagaagaa ctacctggcc    120

tggtaccagc agaaacccgg caaggccccc aagctgctgg tctacttcgc ctctaccagg    180

gattccggcg tccccagcag gttcagcggc agcggcagcg gcaccgactt cacactgacc    240

atcagcagcc tgcagcccga ggacttcgcc acctactact gcctgcagca cttcggcacc    300

cctcccactt ttggccaggg caccaagctg gagattaagc gtacggtggc cgcccccagc    360

gtgttcatct tcccccccag cgatgagcag ctgaagagcg gcaccgccag cgtggtgtgt    420

ctgctgaaca acttctaccc ccgggaggcc aaggtgcagt ggaaggtgga caatgccctg    480

cagagcggca acagccagga gagcgtgacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaaccg gggcgagtgc    660
```

<210> SEQ ID NO 72
<211> LENGTH: 1338
<212> TYPE: DNA
<213> ORGANISM: Artificial
<220> FEATURE:
<223> OTHER INFORMATION: H4L7, heavy chain humanised construct

<400> SEQUENCE: 72

```
caggtgcagc tccaggagag cggccccggc ctggtgaagc ctagcgagac cctgagcctg     60
```

acctgcaccg tgagcggctt ctccctgacc gcctacggcg tcaactggat caggcagccc 120
cccggcaaag gcctggagtg gctggggatg atctgggacg acggcagcac cgactacaac 180
agcgccctga agagcaggct gaccatcagc aaggacaaca gcaagaacca ggtgagcctg 240
aagctgagca gcgtgactgc cgccgacacc gccgtctatt actgcgccag ggagggcgac 300
gtggccttcg attactgggg ccagggcaca ctagtgaccg tgtccagcgc cagcaccaag 360
ggccccagcg tgttcccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg cccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 73
<211> LENGTH: 660
<212> TYPE: DNA
<213> ORGANISM: Artificial
<220> FEATURE:
<223> OTHER INFORMATION: J11L7, light chain humanised construct

<400> SEQUENCE: 73
gacatccaga tgacccagag cccctctagc ctcagcgcca gcgtgggcga cagggtgacc 60
atcacctgca agagcagcca gagcctgctg aaccccagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tcccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 74
<211> LENGTH: 1338

<212> TYPE: DNA
<213> ORGANISM: Artificial
<220> FEATURE:
<223> OTHER INFORMATION: J11L7, heavy chain humanised construct

<400> SEQUENCE: 74
caggtgcagc tcgtgcagag cggggccgaa gtcaagaaac ccggcagctc cgtgaaggtg 60
agctgcaagg ccagcggctt ctctctcact gcctacggcg tgaactgggt gaggcaggct 120
cccggccagg gcctggagtg gatgggcatg atctgggacg acggcagcac cgactacgac 180
agcgccctga agagcagggt gaccatcacc gccgacaaga gcaccagcac cgcctacatg 240
gaactgagca gcctgaggag cgaggacacc gccgtgtact attgcgccag ggagggcgac 300
gtggccttcg attactgggg ccagggcaca ctagtgaccg tgtccagcgc cagcaccaag 360
ggccccagcg tgttccccct ggccccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg ccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 75
<211> LENGTH: 660
<212> TYPE: DNA
<213> ORGANISM: Artificial
<220> FEATURE:
<223> OTHER INFORMATION: H2L7, light chain humanised construct

<400> SEQUENCE: 75
gacatccaga tgacccagag cccctctagc ctcagcgcca gcgtgggcga cagggtgacc 60
atcacctgca agagcagcca gagcctgctg aaccccagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tcccccccag cgatgagcag ctgaagagcg gcaccgccag cgtggtgtgt 420
ctgctgaaca acttctaccc ccgggaggcc aaggtgcagt ggaaggtgga caatgccctg 480

-continued

```
cagagcggca acagccagga gagcgtgacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaaccg gggcgagtgc    660
```

<210> SEQ ID NO 76
<211> LENGTH: 1338
<212> TYPE: DNA
<213> ORGANISM: Artificial
<220> FEATURE:
<223> OTHER INFORMATION: H2L7, heavy chain humanised construct

<400> SEQUENCE: 76

```
caggtgcagc tccaggagag cggccccggc ctggtgaagc ctagcgagac cctgagcctg      60

acctgcaccg tgagcggctt ctccctgacc gcctacggcg tcaactggat caggcagccc    120

cccggcaaag gcctggagtg gattgggatg atctgggacg acggcagcac cgactacaac    180

agcgccctga agagcagggt gaccatcagc aaggacaaca gcaagaacca ggtgagcctg    240

aagctgagca gcgtgactgc cgccgacacc gccgtctatt actgcgccag ggagggcgac    300

gtggccttcg attactgggg ccagggcaca ctagtgaccg tgtccagcgc cagcaccaag    360

ggccccagcg tgttccccct ggcccccagc agcaagagca ccagcggcgg cacagccgcc    420

ctgggctgcc tggtgaagga ctacttcccc gaaccggtga ccgtgtcctg gaacagcgga    480

gccctgacca gcggcgtgca caccttcccc gccgtgctgc agagcagcgg cctgtacagc    540

ctgagcagcg tggtgaccgt gcccagcagc agcctgggca cccagaccta catctgtaac    600

gtgaaccaca agcccagcaa caccaaggtg gacaagaagg tggagcccaa gagctgtgac    660

aagacccaca cctgcccccc ctgccctgcc cccgagctgc tgggaggccc cagcgtgttc    720

ctgttccccc ccaagcctaa ggacaccctg atgatcagca gaacccccga ggtgacctgt    780

gtggtggtgg atgtgagcca cgaggaccct gaggtgaagt tcaactggta cgtggacggc    840

gtggaggtgc acaatgccaa gaccaagccc agggaggagc agtacaacag cacctaccgg    900

gtggtgtccg tgctgaccgt gctgcaccag gattggctga acggcaagga gtacaagtgt    960

aaggtgtcca acaaggccct gcctgcccct atcgagaaaa ccatcagcaa ggccaagggc   1020

cagcccagag agccccaggt gtacaccctg ccccctagca gagatgagct gaccaagaac   1080

caggtgtccc tgacctgcct ggtgaagggc ttctacccca gcgacatcgc cgtggagtgg   1140

gagagcaacg gccagcccga gaacaactac aagaccaccc cccctgtgct ggacagcgat   1200

ggcagcttct tcctgtacag caagctgacc gtggacaaga gcagatggca gcagggcaac   1260

gtgttcagct gctccgtgat gcacgaggcc ctgcacaatc actacaccca gaagagcctg   1320

agcctgtccc ctggcaag                                                 1338
```

<210> SEQ ID NO 77
<211> LENGTH: 660
<212> TYPE: DNA
<213> ORGANISM: Artificial
<220> FEATURE:
<223> OTHER INFORMATION: J13L7, light chain humanised construct

<400> SEQUENCE: 77

```
gacatccaga tgacccagag cccctctagc ctcagcgcca gcgtgggcga cagggtgacc      60

atcacctgca agagcagcca gagcctgctg aaccccagca accagaagaa ctacctggcc    120

tggtaccagc agaaacccgg caaggccccc aagctgctgg tctacttcgc ctctaccagg    180

gattccggcg tccccagcag gttcagcggc agcggcagcg gcaccgactt cacactgacc    240
```

atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 78
<211> LENGTH: 1338
<212> TYPE: DNA
<213> ORGANISM: Artificial
<220> FEATURE:
<223> OTHER INFORMATION: J13L7, heavy chain humanised construct

<400> SEQUENCE: 78
caggtgcagc tcgtgcagag cggggccgaa gtcaagaaac ccggcagctc cgtgaaggtg 60
agctgcaagg ccagcggcgg caccttcagc gcctacggcg tgaactgggt gaggcaggct 120
cccggccagg gcctggagtg gatgggcatg atctgggacg acggcagcac cgactacgac 180
agcgccctga agagcagggt gaccatcacc gccgacaaga gcaccagcac cgcctacatg 240
gaactgagca gcctgaggag cgaggacacc gccgtgtact attgcgccag ggagggcgac 300
gtggccttcg attactgggg ccagggcaca ctagtgaccg tgtccagcgc cagcaccaag 360
ggccccagcg tgttccccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg ccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 79
<211> LENGTH: 660
<212> TYPE: DNA
<213> ORGANISM: Artificial
<220> FEATURE:
<223> OTHER INFORMATION: H7L7, light chain humanised construct -continued

<400> SEQUENCE: 79
gacatccaga tgacccagag cccctctagc ctcagcgcca gcgtgggcga cagggtgacc 60
atcacctgca agagcagcca gagcctgctg aaccccagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 80
<211> LENGTH: 1338
<212> TYPE: DNA
<213> ORGANISM: Artificial
<220> FEATURE:
<223> OTHER INFORMATION: H7L7, heavy chain humanised construct

<400> SEQUENCE: 80
caggtgcagc tccaggagag cggccccggc ctggtgaagc ctagcgagac cctgagcctg 60
acctgcaccg tgagcggcgg ctccatcagc gcctacggcg tcaactggat caggcagccc 120
cccggcaaag gcctggagtg gattgggatg atctgggacg acggcagcac cgactacgac 180
agcgccctga agagcagggt gaccatcagc gtggacacca gcaagaacca gttcagcctg 240
aagctgagca gcgtgactgc cgccgacacc gccgtctatt actgcgccag ggagggcgac 300
gtggccttcg attactgggg ccagggcaca ctagtgaccg tgtccagcgc cagcaccaag 360
ggccccagcg tgttcccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg cccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 81
<211> LENGTH: 660
<212> TYPE: DNA
<213> ORGANISM: Artificial
<220> FEATURE:
<223> OTHER INFORMATION: J0L7, light chain humanised construct

<400> SEQUENCE: 81
gacatccaga tgacccagag cccctctagc ctcagcgcca gcgtgggcga cagggtgacc 60
atcacctgca agagcagcca gagcctgctg aaccccagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tcccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 82
<211> LENGTH: 1338
<212> TYPE: DNA
<213> ORGANISM: Artificial
<220> FEATURE:
<223> OTHER INFORMATION: J0L7, heavy chain humanised construct

<400> SEQUENCE: 82
caggtgcagc tcgtgcagag cggggccgaa gtcaagaaac ccggcagctc cgtgaaggtg 60
agctgcaagg ccagcggcgg caccttcagc gcctacggcg tgaactgggt gaggcaggct 120
cccggccagg gcctggagtg gatgggcatg atctgggacg acggcagcac cgactacaac 180
agcgccctga agagcagggt gaccatcacc gccgacaaga gcaccagcac cgcctacatg 240
gaactgagca gcctgaggag cgaggacacc gccgtgtact attgcgccag ggagggcgac 300
gtggccttcg attactgggg ccagggcaca ctagtgaccg tgtccagcgc cagcaccaag 360
ggccccagcg tgttccccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg ccccctagca gagatgagct gaccaagaac 1080

-continued

```
caggtgtccc tgacctgcct ggtgaagggc ttctacccca gcgacatcgc cgtggagtgg   1140

gagagcaacg gccagcccga gaacaactac aagaccaccc cccctgtgct ggacagcgat   1200

ggcagcttct tcctgtacag caagctgacc gtggacaaga gcagatggca gcagggcaac   1260

gtgttcagct gctccgtgat gcacgaggcc ctgcacaatc actacaccca gaagagcctg   1320

agcctgtccc ctggcaag                                                 1338
```

<210> SEQ ID NO 83
<211> LENGTH: 660
<212> TYPE: DNA
<213> ORGANISM: Artificial
<220> FEATURE:
<223> OTHER INFORMATION: H0L7, light chain humanised construct

<400> SEQUENCE: 83

```
gacatccaga tgacccagag cccctctagc ctcagcgcca gcgtgggcga cagggtgacc     60

atcacctgca agagcagcca gagcctgctg aaccccagca accagaagaa ctacctggcc    120

tggtaccagc agaaacccgg caaggccccc aagctgctgg tctacttcgc ctctaccagg    180

gattccggcg tccccagcag gttcagcggc agcggcagcg gcaccgactt cacactgacc    240

atcagcagcc tgcagcccga ggacttcgcc acctactact gcctgcagca cttcggcacc    300

cctcccactt ttggccaggg caccaagctg gagattaagc gtacggtggc cgcccccagc    360

gtgttcatct tcccccccag cgatgagcag ctgaagagcg gcaccgccag cgtggtgtgt    420

ctgctgaaca acttctaccc ccgggaggcc aaggtgcagt ggaaggtgga caatgccctg    480

cagagcggca acagccagga gagcgtgacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaaccg gggcgagtgc    660
```

<210> SEQ ID NO 84
<211> LENGTH: 1338
<212> TYPE: DNA
<213> ORGANISM: Artificial
<220> FEATURE:
<223> OTHER INFORMATION: H0L7, heavy chain humanised construct

<400> SEQUENCE: 84

```
caggtgcagc tccaggagag cggccccggc ctggtgaagc ctagcgagac cctgagcctg     60

acctgcaccg tgagcggcgg ctccatcagc gcctacggcg tcaactggat caggcagccc    120

cccggcaaag gcctggagtg gattgggatg atctgggacg acggcagcac cgactacaac    180

agcgccctga agagcagggt gaccatcagc gtggacacca gcaagaacca gttcagcctg    240

aagctgagca gcgtgactgc cgccgacacc gccgtctatt actgcgccag ggagggcgac    300

gtggccttcg attactgggg ccagggcaca ctagtgaccg tgtccagcgc cagcaccaag    360

ggccccagcg tgttccccct ggcccccagc agcaagagca ccagcggcgg cacagccgcc    420

ctgggctgcc tggtgaagga ctacttcccc gaaccggtga ccgtgtcctg gaacagcgga    480

gccctgacca gcggcgtgca caccttcccc gccgtgctgc agagcagcgg cctgtacagc    540

ctgagcagcg tggtgaccgt gcccagcagc agcctgggca cccagaccta catctgtaac    600

gtgaaccaca agcccagcaa caccaaggtg gacaagaagg tggagcccaa gagctgtgac    660

aagacccaca cctgcccccc ctgccctgcc cccgagctgc tgggaggccc cagcgtgttc    720

ctgttccccc ccaagcctaa ggacaccctg atgatcagca gaacccccga ggtgacctgt    780

gtggtggtgg atgtgagcca cgaggaccct gaggtgaagt tcaactggta cgtggacggc    840
```

```
gtggaggtgc acaatgccaa gaccaagccc agggaggagc agtacaacag cacctaccgg    900

gtggtgtccg tgctgaccgt gctgcaccag gattggctga acggcaagga gtacaagtgt    960

aaggtgtcca acaaggccct gcctgcccct atcgagaaaa ccatcagcaa ggccaagggc   1020

cagcccagag agccccaggt gtacaccctg ccccctagca gagatgagct gaccaagaac   1080

caggtgtccc tgacctgcct ggtgaagggc ttctacccca gcgacatcgc cgtggagtgg   1140

gagagcaacg gccagcccga gaacaactac aagaccaccc cccctgtgct ggacagcgat   1200

ggcagcttct tcctgtacag caagctgacc gtggacaaga gcagatggca gcagggcaac   1260

gtgttcagct gctccgtgat gcacgaggcc ctgcacaatc actacaccca gaagagcctg   1320

agcctgtccc ctggcaag                                                 1338
```

<210> SEQ ID NO 85
<211> LENGTH: 660
<212> TYPE: DNA
<213> ORGANISM: Artificial
<220> FEATURE:
<223> OTHER INFORMATION: H1L1, light chain humanised construct

<400> SEQUENCE: 85

```
gacatccaga tgacccagag cccctctagc ctcagcgcca gcgtgggcga cagggtgacc     60

atcacctgca agagcagcca gagcctgctg aacggcagca accagaagaa ctacctggcc    120

tggtaccagc agaaacccgg caaggccccc aagctgctgg tctacttcgc ctctaccagg    180

gattccggcg tccccagcag gttcagcggc agcggcagcg gcaccgactt cacactgacc    240

atcagcagcc tgcagcccga ggacttcgcc acctactact gcctgcagca cttcggcacc    300

cctcccactt ttggccaggg caccaagctg gagattaagc gtacggtggc cgcccccagc    360

gtgttcatct tcccccccag cgatgagcag ctgaagagcg gcaccgccag cgtggtgtgt    420

ctgctgaaca acttctaccc ccgggaggcc aaggtgcagt ggaaggtgga caatgccctg    480

cagagcggca acagccagga gagcgtgacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaaccg gggcgagtgc    660
```

<210> SEQ ID NO 86
<211> LENGTH: 1338
<212> TYPE: DNA
<213> ORGANISM: Artificial
<220> FEATURE:
<223> OTHER INFORMATION: H1L1, heavy chain humanised construct

<400> SEQUENCE: 86

```
caggtgcagc tccaggagag cggccccggc ctggtgaagc ctagcgagac cctgagcctg     60

acctgcaccg tgagcggctt ctccctgacc gcctacggcg tcaactggat caggcagccc    120

cccggcaaag gcctggagtg gattgggatg atctgggacg acggcagcac cgactacaac    180

agcgccctga agagcagggt gaccatcagc gtggacacca gcaagaacca gttcagcctg    240

aagctgagca gcgtgactgc cgccgacacc gccgtctatt actgcgccag ggagggcgac    300

gtggccttcg attactgggg ccagggcaca ctagtgaccg tgtccagcgc cagcaccaag    360

ggccccagcg tgttccccct ggcccccagc agcaagagca ccagcggcgg cacagccgcc    420

ctgggctgcc tggtgaagga ctacttcccc gaaccggtga ccgtgtcctg gaacagcgga    480

gccctgacca gcggcgtgca caccttcccc gccgtgctgc agagcagcgg cctgtacagc    540
```

-continued

```
ctgagcagcg tggtgaccgt gcccagcagc agcctgggca cccagaccta catctgtaac    600

gtgaaccaca agcccagcaa caccaaggtg gacaagaagg tggagcccaa gagctgtgac    660

aagacccaca cctgcccccc ctgccctgcc cccgagctgc tgggaggccc cagcgtgttc    720

ctgttccccc ccaagcctaa ggacaccctg atgatcagca gaacccccga ggtgacctgt    780

gtggtggtgg atgtgagcca cgaggaccct gaggtgaagt tcaactggta cgtggacggc    840

gtggaggtgc acaatgccaa gaccaagccc agggaggagc agtacaacag cacctaccgg    900

gtggtgtccg tgctgaccgt gctgcaccag gattggctga acggcaagga gtacaagtgt    960

aaggtgtcca acaaggccct gcctgcccct atcgagaaaa ccatcagcaa ggccaagggc   1020

cagcccagag agccccaggt gtacaccctg ccccctagca gagatgagct gaccaagaac   1080

caggtgtccc tgacctgcct ggtgaagggc ttctacccca gcgacatcgc cgtggagtgg   1140

gagagcaacg gccagcccga gaacaactac aagaccaccc cccctgtgct ggacagcgat   1200

ggcagcttct tcctgtacag caagctgacc gtggacaaga gcagatggca gcagggcaac   1260

gtgttcagct gctccgtgat gcacgaggcc ctgcacaatc actacaccca gaagagcctg   1320

agcctgtccc ctggcaag                                                 1338
```

<210> SEQ ID NO 87
<211> LENGTH: 660
<212> TYPE: DNA
<213> ORGANISM: Artificial
<220> FEATURE:
<223> OTHER INFORMATION: H5L1, light chain humanised construct

<400> SEQUENCE: 87

```
gacatccaga tgacccagag cccctctagc ctcagcgcca gcgtgggcga cagggtgacc     60

atcacctgca agagcagcca gagcctgctg aacggcagca accagaagaa ctacctggcc    120

tggtaccagc agaaacccgg caaggccccc aagctgctgg tctacttcgc ctctaccagg    180

gattccggcg tccccagcag gttcagcggc agcggcagcg gcaccgactt cacactgacc    240

atcagcagcc tgcagcccga ggacttcgcc acctactact gcctgcagca cttcggcacc    300

cctcccactt ttggccaggg caccaagctg gagattaagc gtacggtggc cgcccccagc    360

gtgttcatct tcccccccag cgatgagcag ctgaagagcg gcaccgccag cgtggtgtgt    420

ctgctgaaca acttctaccc ccgggaggcc aaggtgcagt ggaaggtgga caatgccctg    480

cagagcggca acagccagga gagcgtgacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaaccg gggcgagtgc    660
```

<210> SEQ ID NO 88
<211> LENGTH: 1338
<212> TYPE: DNA
<213> ORGANISM: Artificial
<220> FEATURE:
<223> OTHER INFORMATION: H5L1, heavy chain humanised construct

<400> SEQUENCE: 88

```
caggtgcagc tccaggagag cggccccggc ctggtgaagc ctagcgagac cctgagcctg     60

acctgcaccg tgagcggctt ctccctgacc gcctacggcg tcaactggat caggcagccc    120

cccggcaaag gcctggagtg gattgggatg atctgggacg acggcagcac cgactacgac    180

agcgccctga agagcagggt gaccatcagc gtggacacca gcaagaacca gttcagcctg    240

aagctgagca gcgtgactgc cgccgacacc gccgtctatt actgcgccag ggagggcgac    300
```

-continued

```
gtggccttcg attactgggg ccagggcaca ctagtgaccg tgtccagcgc cagcaccaag    360

ggccccagcg tgttcccct ggccccagc agcaagagca ccagcggcgg cacagccgcc    420

ctgggctgcc tggtgaagga ctacttcccc gaaccggtga ccgtgtcctg gaacagcgga    480

gccctgacca gcggcgtgca caccttcccc gccgtgctgc agagcagcgg cctgtacagc    540

ctgagcagcg tggtgaccgt gcccagcagc agcctgggca cccagaccta catctgtaac    600

gtgaaccaca agcccagcaa caccaaggtg gacaagaagg tggagcccaa gagctgtgac    660

aagacccaca cctgccccc ctgccctgcc cccgagctgc tgggaggccc cagcgtgttc    720

ctgttccccc ccaagcctaa ggacaccctg atgatcagca gaacccccga ggtgacctgt    780

gtggtggtgg atgtgagcca cgaggaccct gaggtgaagt tcaactggta cgtggacggc    840

gtggaggtgc acaatgccaa gaccaagccc agggaggagc agtacaacag cacctaccgg    900

gtggtgtccg tgctgaccgt gctgcaccag gattggctga acggcaagga gtacaagtgt    960

aaggtgtcca acaaggccct gcctgcccct atcgagaaaa ccatcagcaa ggccaagggc   1020

cagcccagag agccccaggt gtacaccctg cccctagca gagatgagct gaccaagaac   1080

caggtgtccc tgacctgcct ggtgaagggc ttctacccca gcgacatcgc cgtggagtgg   1140

gagagcaacg gccagcccga gaacaactac aagaccaccc cccctgtgct ggacagcgat   1200

ggcagcttct tcctgtacag caagctgacc gtggacaaga gcagatggca gcagggcaac   1260

gtgttcagct gctccgtgat gcacgaggcc ctgcacaatc actacaccca gaagagcctg   1320

agcctgtccc ctggcaag                                                 1338
```

```
<210> SEQ ID NO 89
<211> LENGTH: 660
<212> TYPE: DNA
<213> ORGANISM: Artificial
<220> FEATURE:
<223> OTHER INFORMATION: J7L1, light chain humanised construct

<400> SEQUENCE: 89

gacatccaga tgacccagag cccctctagc ctcagcgcca gcgtgggcga cagggtgacc     60

atcacctgca agagcagcca gagcctgctg aacggcagca accagaagaa ctacctggcc    120

tggtaccagc agaaacccgg caaggccccc aagctgctgg tctacttcgc ctctaccagg    180

gattccggcg tccccagcag gttcagcggc agcggcagcg gcaccgactt cacactgacc    240

atcagcagcc tgcagcccga ggacttcgcc acctactact gcctgcagca cttcggcacc    300

cctcccactt ttggccaggg caccaagctg gagattaagc gtacggtggc cgcccccagc    360

gtgttcatct tcccccccag cgatgagcag ctgaagagcg gcaccgccag cgtggtgtgt    420

ctgctgaaca acttctaccc ccgggaggcc aaggtgcagt ggaaggtgga caatgccctg    480

cagagcggca acagccagga gagcgtgacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaaccg gggcgagtgc    660
```

```
<210> SEQ ID NO 90
<211> LENGTH: 1338
<212> TYPE: DNA
<213> ORGANISM: Artificial
<220> FEATURE:
<223> OTHER INFORMATION: J7L1, heavy chain humanised construct

<400> SEQUENCE: 90
```

```
caggtgcagc tcgtgcagag cggggccgaa gtcaagaaac ccggcagctc cgtgaaggtg     60

agctgcaagg ccagcggctt ctctctcact gcctacggcg tgaactgggt gaggcaggct    120

cccggccagg gcctggagtg gatgggcatg atctgggacg acggcagcac cgactacaac    180

agcgccctga agagcagggt gaccatcacc gccgacaaga gcaccagcac cgcctacatg    240

gaactgagca gcctgaggag cgaggacacc gccgtgtact attgcgccag ggagggcgac    300

gtggccttcg attactgggg ccagggcaca ctagtgaccg tgtccagcgc cagcaccaag    360

ggccccagcg tgttcccctg ggcccccagc agcaagagca ccagcggcgg cacagccgcc    420

ctgggctgcc tggtgaagga ctacttcccc gaaccggtga ccgtgtcctg gaacagcgga    480

gccctgacca gcggcgtgca caccttcccc gccgtgctgc agagcagcgg cctgtacagc    540

ctgagcagcg tggtgaccgt gcccagcagc agcctgggca cccagaccta catctgtaac    600

gtgaaccaca agcccagcaa caccaaggtg gacaagaagg tggagcccaa gagctgtgac    660

aagacccaca cctgcccccc ctgccctgcc cccgagctgc tgggaggccc cagcgtgttc    720

ctgttccccc ccaagcctaa ggacaccctg atgatcagca gaacccccga ggtgacctgt    780

gtggtggtgg atgtgagcca cgaggaccct gaggtgaagt tcaactggta cgtggacggc    840

gtggaggtgc acaatgccaa gaccaagccc agggaggagc agtacaacag cacctaccgg    900

gtggtgtccg tgctgaccgt gctgcaccag gattggctga acggcaagga gtacaagtgt    960

aaggtgtcca acaaggccct gcctgcccct atcgagaaaa ccatcagcaa ggccaagggc   1020

cagcccagag agccccaggt gtacaccctg cccccctagca gagatgagct gaccaagaac   1080

caggtgtccc tgacctgcct ggtgaagggc ttctacccca gcgacatcgc cgtggagtgg   1140

gagagcaacg gccagcccga gaacaactac aagaccaccc cccctgtgct ggacagcgat   1200

ggcagcttct tcctgtacag caagctgacc gtggacaaga gcagatggca gcagggcaac   1260

gtgttcagct gctccgtgat gcacgaggcc ctgcacaatc actacaccca gaagagcctg   1320

agcctgtccc ctggcaag                                                 1338
```

<210> SEQ ID NO 91
<211> LENGTH: 660
<212> TYPE: DNA
<213> ORGANISM: Artificial
<220> FEATURE:
<223> OTHER INFORMATION: J11L1, light chain humanised construct

<400> SEQUENCE: 91

```
gacatccaga tgacccagag cccctctagc ctcagcgcca gcgtgggcga cagggtgacc     60

atcacctgca agagcagcca gagcctgctg aacggcagca accagaagaa ctacctggcc    120

tggtaccagc agaaacccgg caaggccccc aagctgctgg tctacttcgc ctctaccagg    180

gattccggcg tccccagcag gttcagcggc agcggcagcg gcaccgactt cacactgacc    240

atcagcagcc tgcagcccga ggacttcgcc acctactact gcctgcagca cttcggcacc    300

cctcccactt ttggccaggg caccaagctg gagattaagc gtacggtggc cgcccccagc    360

gtgttcatct tcccccccag cgatgagcag ctgaagagcg gcaccgccag cgtggtgtgt    420

ctgctgaaca acttctaccc ccgggaggcc aaggtgcagt ggaaggtgga caatgccctg    480

cagagcggca acagccagga gagcgtgacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaaccg gggcgagtgc    660
```

<210> SEQ ID NO 92
<211> LENGTH: 1338
<212> TYPE: DNA
<213> ORGANISM: Artificial
<220> FEATURE:
<223> OTHER INFORMATION: J11L1, heavy chain humanised construct

<400> SEQUENCE: 92
caggtgcagc tcgtgcagag cggggccgaa gtcaagaaac ccggcagctc cgtgaaggtg 60
agctgcaagg ccagcggctt ctctctcact gcctacggcg tgaactgggt gaggcaggct 120
cccggccagg gcctggagtg gatgggcatg atctgggacg acggcagcac cgactacgac 180
agcgccctga agagcagggt gaccatcacc gccgacaaga gcaccagcac cgcctacatg 240
gaactgagca gcctgaggag cgaggacacc gccgtgtact attgcgccag ggagggcgac 300
gtggccttcg attactgggg ccagggcaca ctagtgaccg tgtccagcgc cagcaccaag 360
ggccccagcg tgttccccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg ccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 93
<211> LENGTH: 660
<212> TYPE: DNA
<213> ORGANISM: Artificial
<220> FEATURE:
<223> OTHER INFORMATION: J13L1, light chain humanised construct

<400> SEQUENCE: 93
gacatccaga tgacccagag cccctctagc ctcagcgcca gcgtgggcga cagggtgacc 60
atcacctgca agagcagcca gagcctgctg aacggcagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tcccccccag cgatgagcag ctgaagagcg gcaccgccag cgtggtgtgt 420

-continued ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 94
<211> LENGTH: 1338
<212> TYPE: DNA
<213> ORGANISM: Artificial
<220> FEATURE:
<223> OTHER INFORMATION: J13L1, heavy chain humanised construct

<400> SEQUENCE: 94
caggtgcagc tcgtgcagag cggggccgaa gtcaagaaac ccggcagctc cgtgaaggtg 60
agctgcaagg ccagcggcgg caccttcagc gcctacggcg tgaactgggt gaggcaggct 120
cccggccagg gcctggagtg gatgggcatg atctgggacg acggcagcac cgactacgac 180
agcgccctga agagcagggt gaccatcacc gccgacaaga gcaccagcac cgcctacatg 240
gaactgagca gcctgaggag cgaggacacc gccgtgtact attgcgccag ggagggcgac 300
gtggccttcg attactgggg ccagggcaca ctagtgaccg tgtccagcgc cagcaccaag 360
ggccccagcg tgttccccct ggccccca gc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg ccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 95
<211> LENGTH: 660
<212> TYPE: DNA
<213> ORGANISM: Artificial
<220> FEATURE:
<223> OTHER INFORMATION: H7L1, light chain humanised construct

<400> SEQUENCE: 95
gacatccaga tgacccagag cccctctagc ctcagcgcca gcgtgggcga cagggtgacc 60
atcacctgca agagcagcca gagcctgctg aacggcagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 96
<211> LENGTH: 1338
<212> TYPE: DNA
<213> ORGANISM: Artificial
<220> FEATURE:
<223> OTHER INFORMATION: H7L1, heavy chain humanised construct

<400> SEQUENCE: 96
caggtgcagc tccaggagag cggccccggc ctggtgaagc ctagcgagac cctgagcctg 60
acctgcaccg tgagcggcgg ctccatcagc gcctacggcg tcaactggat caggcagccc 120
cccggcaaag gcctggagtg gattgggatg atctgggacg acggcagcac cgactacgac 180
agcgccctga agagcagggt gaccatcagc gtggacacca gcaagaacca gttcagcctg 240
aagctgagca gcgtgactgc cgccgacacc gccgtctatt actgcgccag ggagggcgac 300
gtggccttcg attactgggg ccagggcaca ctagtgaccg tgtccagcgc cagcaccaag 360
ggccccagcg tgttcccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg ccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 97
<211> LENGTH: 660
<212> TYPE: DNA
<213> ORGANISM: Artificial
<220> FEATURE:

<223> OTHER INFORMATION: J0L1, light chain humanised construct

<400> SEQUENCE: 97
gacatccaga tgacccagag cccctctagc ctcagcgcca gcgtgggcga cagggtgacc 60
atcacctgca agagcagcca gagcctgctg aacggcagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 98
<211> LENGTH: 1338
<212> TYPE: DNA
<213> ORGANISM: Artificial
<220> FEATURE:
<223> OTHER INFORMATION: J0L1, heavy chain humanised construct

<400> SEQUENCE: 98
caggtgcagc tcgtgcagag cggggccgaa gtcaagaaac ccggcagctc cgtgaaggtg 60
agctgcaagg ccagcggcgg caccttcagc gcctacggcg tgaactgggt gaggcaggct 120
cccggccagg gcctggagtg gatgggcatg atctgggacg acggcagcac cgactacaac 180
agcgccctga agagcagggt gaccatcacc gccgacaaga gcaccagcac cgcctacatg 240
gaactgagca gcctgaggag cgaggacacc gccgtgtact attgcgccag ggagggcgac 300
gtggccttcg attactgggg ccagggcaca ctagtgaccg tgtccagcgc cagcaccaag 360
ggccccagcg tgttccccct ggccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020
cagcccagag agccccaggt gtacaccctg cccccctagca gagatgagct gaccaagaac 1080
caggtgtccc tgacctgcct ggtgaagggc ttctacccca gcgacatcgc cgtggagtgg 1140
gagagcaacg gccagcccga gaacaactac aagaccaccc cccctgtgct ggacagcgat 1200
ggcagcttct tcctgtacag caagctgacc gtggacaaga gcagatggca gcagggcaac 1260
gtgttcagct gctccgtgat gcacgaggcc ctgcacaatc actacaccca gaagagcctg 1320
agcctgtccc ctggcaag 1338

<210> SEQ ID NO 99
<211> LENGTH: 660
<212> TYPE: DNA
<213> ORGANISM: Artificial
<220> FEATURE:
<223> OTHER INFORMATION: H0L1, light chain humanised construct

<400> SEQUENCE: 99
gacatccaga tgacccagag cccctctagc ctcagcgcca gcgtgggcga cagggtgacc 60
atcacctgca agagcagcca gagcctgctg aacggcagca accagaagaa ctacctggcc 120
tggtaccagc agaaacccgg caaggccccc aagctgctgg tctacttcgc ctctaccagg 180
gattccggcg tccccagcag gttcagcggc agcggcagcg gcaccgactt cacactgacc 240
atcagcagcc tgcagcccga ggacttcgcc acctactact gcctgcagca cttcggcacc 300
cctcccactt ttggccaggg caccaagctg gagattaagc gtacggtggc cgcccccagc 360
gtgttcatct tccccccag cgatgagcag ctgaagagcg gcaccgccag cgtggtgtgt 420
ctgctgaaca acttctaccc ccgggaggcc aaggtgcagt ggaaggtgga caatgccctg 480
cagagcggca acagccagga gagcgtgacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaaccg gggcgagtgc 660

<210> SEQ ID NO 100
<211> LENGTH: 1338
<212> TYPE: DNA
<213> ORGANISM: Artificial
<220> FEATURE:
<223> OTHER INFORMATION: H0L1, heavy chain humanised construct

<400> SEQUENCE: 100
caggtgcagc tccaggagag cggccccggc ctggtgaagc ctagcgagac cctgagcctg 60
acctgcaccg tgagcggcgg ctccatcagc gcctacggcg tcaactggat caggcagccc 120
cccggcaaag gcctggagtg gattgggatg atctgggacg acggcagcac cgactacaac 180
agcgccctga agagcagggt gaccatcagc gtggacacca gcaagaacca gttcagcctg 240
aagctgagca gcgtgactgc cgccgacacc gccgtctatt actgcgccag ggagggcgac 300
gtggccttcg attactgggg ccagggcaca ctagtgaccg tgtccagcgc cagcaccaag 360
ggccccagcg tgttccccct ggcccccagc agcaagagca ccagcggcgg cacagccgcc 420
ctgggctgcc tggtgaagga ctacttcccc gaaccggtga ccgtgtcctg gaacagcgga 480
gccctgacca gcggcgtgca caccttcccc gccgtgctgc agagcagcgg cctgtacagc 540
ctgagcagcg tggtgaccgt gcccagcagc agcctgggca cccagaccta catctgtaac 600
gtgaaccaca agcccagcaa caccaaggtg gacaagaagg tggagcccaa gagctgtgac 660
aagacccaca cctgcccccc ctgccctgcc cccgagctgc tgggaggccc cagcgtgttc 720
ctgttccccc ccaagcctaa ggacaccctg atgatcagca gaacccccga ggtgacctgt 780
gtggtggtgg atgtgagcca cgaggaccct gaggtgaagt tcaactggta cgtggacggc 840
gtggaggtgc acaatgccaa gaccaagccc agggaggagc agtacaacag cacctaccgg 900
gtggtgtccg tgctgaccgt gctgcaccag gattggctga acggcaagga gtacaagtgt 960
aaggtgtcca acaaggccct gcctgcccct atcgagaaaa ccatcagcaa ggccaagggc 1020

```
cagcccagag agccccaggt gtacaccctg cccccctagca gagatgagct gaccaagaac   1080

caggtgtccc tgacctgcct ggtgaagggc ttctacccca gcgacatcgc cgtggagtgg   1140

gagagcaacg gccagcccga gaacaactac aagaccaccc cccctgtgct ggacagcgat   1200

ggcagcttct tcctgtacag caagctgacc gtggacaaga gcagatggca gcagggcaac   1260

gtgttcagct gctccgtgat gcacgaggcc ctgcacaatc actacaccca gaagagcctg   1320

agcctgtccc ctggcaag                                                 1338
```

<210> SEQ ID NO 101
<211> LENGTH: 318
<212> TYPE: DNA
<213> ORGANISM: Human

<400> SEQUENCE: 101

```
acggtggccg cccccagcgt gttcatcttc ccccccagcg atgagcagct gaagagcggc     60

accgccagcg tggtgtgtct gctgaacaac ttctaccccc gggaggccaa ggtgcagtgg    120

aaggtggaca atgccctgca gagcggcaac agccaggaga gcgtgaccga gcaggacagc    180

aaggactcca cctacagcct gagcagcacc ctgaccctga gcaaggccga ctacgagaag    240

cacaaggtgt acgcctgtga ggtgacccac cagggcctgt ccagccccgt gaccaagagc    300

ttcaaccggg gcgagtgc                                                  318
```

<210> SEQ ID NO 102
<211> LENGTH: 990
<212> TYPE: DNA
<213> ORGANISM: Human

<400> SEQUENCE: 102

```
gccagcacca agggccccag cgtgttcccc ctggccccca gcagcaagag caccagcggc     60

ggcacagccg ccctgggctg cctggtgaag gactacttcc ccgaaccggt gaccgtgtcc    120

tggaacagcg gagccctgac cagcggcgtg cacaccttcc ccgccgtgct gcagagcagc    180

ggcctgtaca gcctgagcag cgtggtgacc gtgcccagca gcagcctggg cacccagacc    240

tacatctgta acgtgaacca caagcccagc aacaccaagg tggacaagaa ggtggagccc    300

aagagctgtg acaagaccca cacctgcccc ccctgccctg cccccgagct gctgggaggc    360

cccagcgtgt tcctgttccc ccccaagcct aaggacaccc tgatgatcag cagaaccccc    420

gaggtgacct gtgtggtggt ggatgtgagc cacgaggacc ctgaggtgaa gttcaactgg    480

tacgtggacg gcgtggaggt gcacaatgcc aagaccaagc ccagggagga gcagtacaac    540

agcacctacc gggtggtgtc cgtgctgacc gtgctgcacc aggattggct gaacggcaag    600

gagtacaagt gtaaggtgtc caacaaggcc ctgcctgccc ctatcgagaa aaccatcagc    660

aaggccaagg gccagcccag agagccccag gtgtacaccc tgccccctag cagagatgag    720

ctgaccaaga accaggtgtc cctgacctgc ctggtgaagg gcttctaccc cagcgacatc    780

gccgtggagt gggagagcaa cggccagccc gagaacaact acaagaccac ccccccctgtg    840

ctggacagcg atggcagctt cttcctgtac agcaagctga ccgtggacaa gagcagatgg    900

cagcagggca acgtgttcag ctgctccgtg atgcacgagg ccctgcacaa tcactacacc    960

cagaagagcc tgagcctgtc ccctggcaag                                     990
```

<210> SEQ ID NO 103
<211> LENGTH: 348
<212> TYPE: DNA
<213> ORGANISM: Murine

<400> SEQUENCE: 103
caggtgcagc tgaaggagtc aggtcctggc ctggtggcgc cctcacagag cctgtccatc 60
acatgcaccg tctcagggtt ctcattaacc gcctatggtg taaactgggt tcgccagcct 120
ccaggaaagg gtctggagtg gctgggaatg atatgggatg atggaagcac agactataat 180
tcagctctca aatccagact gagcatcagt aaggacaact ccaagagcca agttttctta 240
aaaatgaaca gtctgcaaac tgatgacaca gccaggtact actgtgccag agaaggggac 300
gtagcctttg actactgggg ccaaggcacc actctcacag tctcctca 348

<210> SEQ ID NO 104
<211> LENGTH: 342
<212> TYPE: DNA
<213> ORGANISM: Murine

<400> SEQUENCE: 104
gacattgtga tgacacagtc tccctcctcc ctggctgtgt cagtaggaca gaaggtcact 60
atgagctgca agtccagtca gagcctttta aatggtagca atcaaaagaa ctacttggcc 120
tggtaccagc agaaaccagg acagtctcct aaacttctgg tatactttgc atccactagg 180
gattctgggg tccctgatcg cttcataggc agtggatctg ggacagattt cactcttacc 240
atcagcagtg tgcaggctga agacctggca gattacttct gtctgcaaca ttttggcact 300
cctccgacgt tcggtggagg caccaaactg gaaatcaaac gg 342

<210> SEQ ID NO 105
<211> LENGTH: 1338
<212> TYPE: DNA
<213> ORGANISM: Artificial
<220> FEATURE:
<223> OTHER INFORMATION: IMP731, heavy chain sequence

<400> SEQUENCE: 105
caggtgcagc tgaaggagtc aggtcctggc ctggtggcgc cctcacagag cctgtccatc 60
acatgcaccg tctcagggtt ctcattaacc gcctatggtg taaactgggt tcgccagcct 120
ccaggaaagg gtctggagtg gctgggaatg atatgggatg atggaagcac agactataat 180
tcagctctca aatccagact gagcatcagt aaggacaact ccaagagcca agttttctta 240
aaaatgaaca gtctgcaaac tgatgacaca gccaggtact actgtgccag agaaggggac 300
gtagcctttg actactgggg ccaaggcacc actctcacag tctcctcagc tagcaccaag 360
ggcccatcgg tcttccccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgaccgt gccctccagc agcttgggca cccagaccta catctgcaac 600
gtgaatcaca agcccagcaa caccaaggtg gacaagaaag ttgagcccaa atcttgtgac 660
aaaactcaca catgcccacc gtgcccagca cctgaactcc tggggggacc gtcagtcttc 720
ctcttccccc caaaacccaa ggacaccctc atgatctccc ggacccctga ggtcacatgc 780
gtggtggtgg acgtgagcca cgaagaccct gaggtcaagt tcaactggta cgtggacggc 840
gtggaggtgc ataatgccaa gacaaagccg cgggaggagc agtacaacag cacgtaccgt 900
gtggtcagcg tcctcaccgt cctgcaccag gactggctga atggcaagga gtacaagtgc 960
aaggtctcca acaaagccct cccagccccc atcgagaaaa ccatctccaa agccaaaggg 1020

```
cagccccgag aaccacaggt gtacaccctg cccccatccc gggatgagct gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctacag caagctcacc gtggacaaga gcaggtggca gcaggggaac   1260

gtcttctcat gctccgtgat gcatgaggct ctgcacaacc actacacgca gaagagcctc   1320

tccctgtctc cgggtaaa                                                  1338
```

<210> SEQ ID NO 106
<211> LENGTH: 660
<212> TYPE: DNA
<213> ORGANISM: Artificial
<220> FEATURE:
<223> OTHER INFORMATION: IMP731, light chain sequence

<400> SEQUENCE: 106

```
gacattgtga tgacacagtc tccctcctcc ctggctgtgt cagtaggaca gaaggtcact     60

atgagctgca agtccagtca gagcctttta aatggtagca atcaaaagaa ctacttggcc    120

tggtaccagc agaaaccagg acagtctcct aaacttctgg tatactttgc atccactagg    180

gattctgggg tccctgatcg cttcataggc agtggatctg ggacagattt cactcttacc    240

atcagcagtg tgcaggctga agacctggca gattacttct gtctgcaaca ttttggcact    300

cctccgacgt tcggtggagg caccaaactg gaaatcaaac ggaccgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagttcgccc gtcacaaaga gcttcaacag gggagagtgt    660
```

<210> SEQ ID NO 107
<211> LENGTH: 1251
<212> TYPE: DNA
<213> ORGANISM: Artificial
<220> FEATURE:
<223> OTHER INFORMATION: Recombinant human LAG-3-ECD-His6

<400> SEQUENCE: 107

```
ctccagccag ggctgaggt cccggtggtg tgggcccagg agggggctcc tgcccagctc     60

ccctgcagcc ccacaatccc cctccaggat ctcagccttc tgcgaagagc aggggtcact    120

tggcagcatc agccagacag tggcccgccc gctgccgccc ccggccatcc cctggccccc    180

ggccctcacc cggcggcgcc ctcctcctgg gggcccaggc cccgccgcta cacggtgctg    240

agcgtgggtc ccggaggcct gcgcagcggg aggctgcccc tgcagccccg cgtccagctg    300

gatgagcgcg gccggcagcg cggggacttc tcgctatggc tgcgcccagc ccggcgcgcg    360

gacgccggcg agtaccgcgc cgcggtgcac ctcagggacc gcgccctctc ctgccgcctc    420

cgtctgcgcc tgggccaggc ctcgatgact gccagccccc caggatctct cagagcctcc    480

gactgggtca ttttgaactg ctccttcagc cgccctgacc gcccagcctc tgtgcattgg    540

ttccggaacc ggggccaggg ccgagtccct gtccgggagt ccccccatca ccacttagcg    600

gaaagcttcc tcttcctgcc ccaagtcagc cccatggact ctgggccctg gggctgcatc    660

ctcacctaca gagatggctt caacgtctcc atcatgtata acctcactgt tctgggtctg    720

gagcccccaa ctcccttgac agtgtacgct ggagcaggtt ccagggtggg gctgccctgc    780
```

cgcctgcctg ctggtgtggg gacccggtct ttcctcactg ccaagtggac tcctcctggg 840
ggaggccctg acctcctggt gactggagac aatggcgact ttacccttcg actagaggat 900
gtgagccagg cccaggctgg gacctacacc tgccatatcc atctgcagga acagcagctc 960
aatgccactg tcacattggc aatcatcaca gtgactccca aatcctttgg gtcacctgga 1020
tccctgggga agctgctttg tgaggtgact ccagtatctg gacaagaacg ctttgtgtgg 1080
agctctctgg acaccccatc ccagaggagt ttctcaggac cttggctgga ggcacaggag 1140
gcccagctcc tttcccagcc ttggcaatgc cagctgtacc agggggagag gcttcttgga 1200
gcagcagtgt acttcacaga gctgtctagc ccacaccacc atcatcacca t 1251

<210> SEQ ID NO 108
<211> LENGTH: 1251
<212> TYPE: DNA
<213> ORGANISM: Artificial
<220> FEATURE:
<223> OTHER INFORMATION: Recombinant cynomolgus macaque LAG-3 ECD-His6

<400> SEQUENCE: 108
ccccagccag gggctgagat ctcggtggtg tgggcccagg agggggctcc tgcccagctc 60
ccctgcagcc ccacaatccc cctccaggat ctcagccttc tgcgaagagc aggggtcact 120
tggcagcatc aaccagacag tggcccgccc gctcccgccc ccggccaccc cccggccccc 180
ggccatcgcc cggcggcgcc ctactcttgg gggcccaggc cccgccgcta cacagtgctg 240
agcgtgggtc ctggaggcct gcgcagcggg aggctgcccc tgcagccccg cgtccagctg 300
gatgagcgcg gccggcagcg cggggacttc tcgctgtggc tgcgcccagc ccggcgcgcg 360
gacgccggcg agtaccgcgc cacggtgcac ctcagggacc gcgccctctc ctgccgcctt 420
cgtctgcgcg tgggccaggc ctcgatgact gccagccccc cagggtctct caggacctct 480
gactgggtca ttttgaactg ctccttcagc cgccctgacc gcccagcctc tgtgcattgg 540
ttccggagcc gtggccaggg ccgagtccct gtccaggggt ccccccatca ccacttagcg 600
gaaagcttcc tcttcctgcc ccatgtcggc cccatggact ctgggctctg ggctgcatc 660 ctcacctaca gagatggctt caatgtctcc atcatgtata acctcactgt tctgggtctg 720
gagcccgcaa ctcccttgac agtgtacgct ggagcaggtt ccagggtgga gctgccctgc 780
cgcctgcctc ctgctgtggg gacccagtct ttccttactg ccaagtgggc tcctcctggg 840
ggaggccctg acctcctggt ggctggagac aatggcgact ttacccttcg actagaggat 900
gtaagccagg cccaggctgg gacctacatc tgccatatcc gtctacaggg acagcagctc 960
aatgccactg tcacattggc aatcatcaca gtgactccca aatcctttgg gtcacctggc 1020
tccctgggga agctgctttg tgaggtgact ccagcatctg gacaagaaca ctttgtgtgg 1080
agccccctga acaccccatc ccagaggagt ttctcaggac catggctgga ggcccaggaa 1140
gcccagctcc tttcccagcc ttggcaatgc cagctgcacc agggggagag gcttcttgga 1200
gcagcagtat acttcacaga actgtctagc ccacaccacc atcatcacca t 1251

<210> SEQ ID NO 109
<211> LENGTH: 1251
<212> TYPE: DNA
<213> ORGANISM: Artificial
<220> FEATURE:
<223> OTHER INFORMATION: Recombinant baboon LAG-3 ECD-His6

<400> SEQUENCE: 109

-continued

```
ccccagccag gggctgagat ctcggtggtg tgggcccagg agggggctcc tgcccagctc      60

ccctgcagcc ccacaatccc cctccaggat ctcagccttc tgcgaagagc aggggtcact     120

tggcagcatc aaccagacag tggcccgccc gctcccgccc ccggccaccc cccggccccc     180

ggccatcgcc cggcggcgcc ctactcttgg gggcccaggc cccgccgcta cacagtgctg     240

agcgtgggtc ctggaggcct gcgcagcggg aggctgcccc tgcagccccg cgtccagctg     300

gatgagcgcg gccggcagcg cggggacttc tcgctgtggc tgcgcccagc ccggcgcgcg     360

gacgccggcg agtaccgcgc cacggtgcac ctcagggacc gcgccctctc ctgccgcctt     420

cgtctgcgcg tgggccaggc ctcgatgact gccagccccc cagggtctct caggacctct     480

gactgggtca ttttgaactg ctccttcagc cgccctgacc gcccagcctc tgtgcattgg     540

ttccggagcc gtggccaggg ccaagtccct gtccaggagt ccccccatca ccacttagcg     600

gaaagcttcc tcttcctgcc ccatgtcggc cccatggact ctgggctctg gggctgcatc     660

ctcacctaca gagatggctt caatgtctcc atcatgtata acctcactgt tctgggtctg     720

gagcccacaa ctcccttgac agtgtacgct ggagcaggtt ccagggtgga gctgccctgc     780

cgcctgcctc ctgctgtggg gacccagtct ttccttactg ccaagtgggc tcctcctggg     840

ggaggccctg acctcctggt ggttggagac aatggcaact ttacccttcg actagaggat     900

gtaagccagg cccaggctgg gacctacatc tgccatatcc gtctacaggg acagcagctc     960

aatgccactg tcacattggc aatcatcaca gtgactccca aatcctttgg gtcacctggc    1020

tccctgggga agctgctttg tgaggtgact ccagcatctg gacaagaacg ctttgtgtgg    1080

agccccctga acaccccatc ccagaggagt ttctcaggac cgtggctgga ggcccaggaa    1140

gcccagctcc tttcccagcc ttggcaatgc cagctgcacc agggggagag gcttcttgga    1200

gcagcagtat acttcacaga actgtctagc ccacaccacc atcatcacca t             1251
```

<210> SEQ ID NO 110
<211> LENGTH: 57
<212> TYPE: DNA
<213> ORGANISM: Murine

<400> SEQUENCE: 110

```
atgggctgga gctgcatcat cctgttcctg gtggccaccg ctaccggagt gcacagc        57
```

<210> SEQ ID NO 111
<211> LENGTH: 60
<212> TYPE: DNA
<213> ORGANISM: Murine

<400> SEQUENCE: 111

```
atggaatcac agacccaggt cctcatgttt cttctgctct gggtatctgg tgcctgtgca      60
```

<210> SEQ ID NO 112
<211> LENGTH: 48
<212> TYPE: DNA
<213> ORGANISM: Human

<400> SEQUENCE: 112

```
atgccgctgc tgctactgct gcccctgctg tgggcagggg cgctagct                   48
```